United States Patent
Berkessel et al.

(10) Patent No.: US 10,793,509 B2
(45) Date of Patent: Oct. 6, 2020

(54) COMPOUNDS USEFUL IN THE TREATMENT OF NEOPLASTIC DISEASES

(71) Applicant: UNIVERSITÄT ZU KÖLN, Cologne (DE)

(72) Inventors: Albrecht Berkessel, Erftstadt (DE); Mark Krüger, Hürth (DE); Karl-Anton Kreuzer, Bonn (DE); Simon Poll-Wolbeck, Cologne (DE)

(73) Assignee: UNIVERSITÄT ZU KOLN, Cologne (DE)

( * ) Notice: Subject to any disclaimer, the term of this patent is extended or adjusted under 35 U.S.C. 154(b) by 0 days.

(21) Appl. No.: 15/024,175

(22) PCT Filed: Sep. 24, 2014

(86) PCT No.: PCT/EP2014/070328
§ 371 (c)(1),
(2) Date: Mar. 23, 2016

(87) PCT Pub. No.: WO2015/044177
PCT Pub. Date: Apr. 2, 2015

(65) Prior Publication Data
US 2016/0237023 A1    Aug. 18, 2016

(30) Foreign Application Priority Data
Sep. 24, 2013   (EP) ................... 13185801

(51) Int. Cl.
C07C 203/04   (2006.01)
C07F 7/18   (2006.01)
C07C 309/76   (2006.01)
C07C 247/10   (2006.01)
C07C 69/78   (2006.01)
C07C 69/76   (2006.01)
A61K 31/621   (2006.01)
C07C 69/86   (2006.01)
C07C 69/75   (2006.01)
A61K 31/215   (2006.01)
A61K 31/24   (2006.01)
A61K 31/235   (2006.01)
C07F 7/08   (2006.01)

(52) U.S. Cl.
CPC .......... *C07C 203/04* (2013.01); *A61K 31/215* (2013.01); *A61K 31/235* (2013.01); *A61K 31/24* (2013.01); *A61K 31/621* (2013.01); *C07C 69/75* (2013.01); *C07C 69/76* (2013.01); *C07C 69/78* (2013.01); *C07C 69/86* (2013.01); *C07C 247/10* (2013.01); *C07C 309/76* (2013.01); *C07F 7/081* (2013.01); *C07F 7/1804* (2013.01); *C07C 2601/14* (2017.05)

(58) Field of Classification Search
CPC . C07C 203/04; C07C 2101/14; C07C 247/10; C07C 309/76; C07C 69/75; C07C 69/76; C07C 69/78; C07C 69/86; C07C 2601/14; C07F 7/0818; C07F 7/1852; C07F 7/081; C07F 7/1804; A61K 31/215; A61K 31/235; A61K 31/24; A61K 31/621; A61P 35/00; A61P 35/02
USPC ........................................................ 514/151
See application file for complete search history.

(56) References Cited

U.S. PATENT DOCUMENTS

| | | | |
|---|---|---|---|
| 5,288,871 A | 2/1994 | Santilli et al. | |
| 2009/0005436 A1* | 1/2009 | Carotti | C07D 311/16 514/457 |
| 2010/0009934 A1* | 1/2010 | Rickles | A61K 31/00 514/64 |
| 2010/0160272 A1* | 6/2010 | Gant | C07D 313/12 514/171 |

(Continued)

FOREIGN PATENT DOCUMENTS

| | | | |
|---|---|---|---|
| JP | H10-25294 A | 1/1998 | |
| JP | 2002-003370 A | 1/2002 | |

(Continued)

OTHER PUBLICATIONS

Gehrke, Iris et al. (AN 2012:74531 HCAPLUS, DN 157:537049, Title: The antineoplastic effect of nitric oxide-donating acetylsalicylic acid (NO-ASA) in chronic lymphocytic leukemia (CLL) cells is highly dependent on its positional isomerism; abstract of Therapeutic Advances in Hematology (2011), 2(5), 279-289, 892 reference).*

(Continued)

*Primary Examiner* — Sabiha N Qazi
(74) *Attorney, Agent, or Firm* — Knobbe, Martens, Olson & Bear LLP

(57) ABSTRACT

Compounds and pharmaceutically acceptable salts of the compounds are useful in the treatment of neoplastic diseases or proliferative disorders. The compounds are formulated into pharmaceutical compositions, which can be used in methods of treating neoplastic diseases or proliferative disorders The compounds are useful to treat cancers such as prostate, pancreatic, lung, skin, breast, bladder, colon, and blood cancers. The compounds are represented by the following formula:

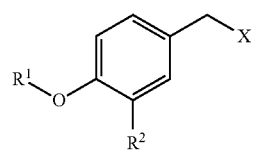

3 Claims, 13 Drawing Sheets

(56) References Cited

U.S. PATENT DOCUMENTS

| | | | | |
|---|---|---|---|---|
| 2011/0319416 | A1* | 12/2011 | Traynelis | C07D 209/08 514/237.5 |
| 2012/0276153 | A1* | 11/2012 | Loutit | A61K 9/0078 424/400 |

FOREIGN PATENT DOCUMENTS

| | | |
|---|---|---|
| JP | 2004-244398 A | 9/2004 |
| JP | 2010-535817 A | 11/2010 |
| RU | 2361 592 C2 | 9/2008 |
| WO | WO 01/04082 A1 | 1/2001 |
| WO | WO 01/21577 A2 | 3/2001 |
| WO | WO 2005/065361 A2 | 7/2005 |
| WO | WO 2009/023631 A1 | 2/2009 |

OTHER PUBLICATIONS

Rubio-Viqueira et al. (Clinical Pharmacology & Therapeutics, col. 85, No. 2m Feb. 2009).*

Rubinstein et al. (JNCI: Journal of the National Cancer Institute, vol. 82, Issue 13, Jul. 4, 1990, pp. 1113-1117, https://doi.org/10.1093/jnci/82.13.1113).*

Matsuda, Akira et al. (ZCAPLUS, AN 1998:79439 DN 128:180423, Original Reference No. 128:35611a, (Abstract of JP 10025294).*

Tromp, Reynier et al. (AN 2004:581046 ZCAPLUS, DN 141:260980, Abstract of Bioorganic and Medicinal Chemistry Letters (2004), 14(16), 4273-4276).*

M. Abdel-Tawab, et al., "Nonsteroidal Anti-Inflammatory Drugs: A Critical Review on Current Concepts Applied to Reduce Gastrointestinal Toxicity," Current Medicinal Chemistry, 2009, vol. 16, No. 16, pp. 2042-2063.

B. C. Ranu, et al., "Use of Zinc Borohydride for Efficient Reduction of Carboxylic Ester to Alcohol. Selective Reduction of Aliphatic Ester in Presence of Aromatic Ester Under Sonication," Tetrahedron Letters, vol. 32, No. 27, 1991, pp. 3243-3246.

J.A. Baron, "Epidemiology of Non-Steroidal Anti-Inflammatory Drugs and Cancer," Prog Exp Tum Res. Basel, Karger, 2003, vol. 37, pp. 1-24.

C. Li, et al., "The Dual Roles of Oxodiperoxovanadate Both as a Nucleophile and an Oxidant in the Green Oxidation of Benzyl Alcohols or Benzyl Halides to Aldehydes and Ketones," Angew. Chem. Int. Ed. 2003, vol. 42, pp. 5063-5066.

I. Gehrke, et al., "The Antineoplastic Effect of Nitric Oxide-donating Acetylsalicylic Acid (NO-ASA) in Chronic Lymphocytic Leukemia (CLL) Cells is Highly Dependent on its Positional Isomerism," Therapeutic Advance in Hematology, 2011, vol. 2, No. 5, pp. 279-289.

J.L. Burgaud, et al., "Nitric-Oxide Releasing Molecules: A New Class of Drugs with Several Major Indications," Current Pharmaceutical Design, 2002, vol. 8, pp. 201-213.

N. Hulsman, et al., "Chemical Insights in the Concept of Hybrid Drugs: The Antitumor Effect of Nitric Oxide-Donating Aspirin Involves a Quinone Methide but Not Nitric Oxide nor Aspirin," Journal of Medicinal Chemistry, 2007, vol. 50, pp. 2424-2431 [P-002633469].

N. Wei, et al., "Synthesis and antifungal activity of 1-(1H-1, 2, 4-triazole-1-yl)-2-(2, 4-difluorophenyl)-3-(N-isopropyl-N-substituted amino)-2-propanols," Yaoxue Shijian Zazhi, 2009, vol. 27, No. 5, pp. 324-328 [XP-002720980].

S.C. Ng, et al., "NSAID-induced gastrointestinal and cardiovascular injury," Current Opinion in Gastroenterology, 2010, vol. 26, pp. 611-617.

P. Cramer, et al., "Prognostic Factors in Chronic lymphocytic leukemia—What Do We Need to Know?" 2011, Nature Reviews Clinical Oncology, 8, pp. 38-47.

R. Razavi, et al., "Nitric Oxide-Donating Acetylsalicylic Acid Induces Apoptosis in Chronic Lymphocytic Leukemia Cells and Shows Strong Antitumor Efficacy In Vivo," Clinical Cancer Research, 2011, vol. 17, pp. 286-293.

S.J. Shiff, et al., "Aspirin for Cancer," Nature Medicine, Dec. 1999, vol. 5, No. 12, pp. 1348-1349.

T. Dunlap, et al., "Quinone-Induced Activation of Keap1/Nrf2 Signaling by Aspirin Prodrugs Masquerading as Nitric Oxide," Chemical Research in Toxicology, 2012, vol. 25(12), pp. 2725-2736.

T. Höfler, et al., "Photo-Fries Rearrangement in Polymeric Media: An Investigation on Fully Aromatic Esters Containing the Naphthyl Chromophore," Macromolecular Chemistry and Physics, 2008, vol. 209, pp. 488-498.

M.J. Thun, et al., "Nonsteroidal Anti-inflammatory Drugs as Anticancer Agents: Mechanistic, Pharmacologic, and Clinical Issues," Journal of the National Cancer Institute, Feb. 20, 2002, vol. 94, No. 4, pp. 252-266.

W. Weissflog, et al., "From Laterally Branched Mesogens to Novel Twin Molecules", Liquid Crystals, 1989, vol. 5, No. 1, pp. 111-122.

J.L. Wallace, et al., "Potential Cardioprotective Actions of No-Releasing Aspirin," Nature Reviews Drug Discovery, May 2002, vol. 1, pp. 375-382.

Z.G. Dan, et al., "Design and synthesis of novel triazole antifungal derivatives based on the active site of fungal lanosterol 14a-demethylase (CYP51)", Chinese Chemical Letters, 2009, vol. 20, pp. 935-938.

Lam, P., et al., Cyclic HIV Protease Inhibitors: Synthesis, Conformational Analysis, P2/P2' Structure—Activity Relationship, and Molecular Recognition of Cyclic Ureas, Journal of Medicinal Chemistry 39(18):3514-3525, 1996.

Ankala, S.V., and G. Fenteany, Aryl, Alkyl bis-Silyl Ethers: Rapid Access to Monopotected Aryl Alkyl and Biaryl Ethers, Synlett, No. 6, pp. 825-828, 2003.

Berlin, A.Y., Methyl Vanillyl Sulfide, The Journal of Applied Chemistry of the USSR, 25(5):645-646, May 1952.

Li, C., et al., The Dual Roles of Oxodiperoxovanadate Both as a Nucleophile and an Oxidant in the Green Oxidation of Benzyl Alcohols or Benzyl Halides to Aldehydes and Ketones, Angew. Chem. Int. Ed. 42:5063-5066, 2003.

Rosenau., T., et al., A Mild, Simple and General Procedure for the Oxidation of Benzyl Alcohols to Benzaldehydes, Synthetic Communications, 26(2):315-320, 1996.

Office Action received in Australian Application No. 2014327311 dated Nov. 16, 2017.

* cited by examiner

The proposed mechanism:

N. Hulsman, J. P. Medema, C. Bos, et al., *J. Med. Chem.* 2007, *50*, 2424-2431
*) J. L. Williams, P. Jia, N. Ouyang et al., *Exp. Cell Res.* 2011, *10*, 1359-1367.

The „NO"-moiety:

Figure 2 Top Part
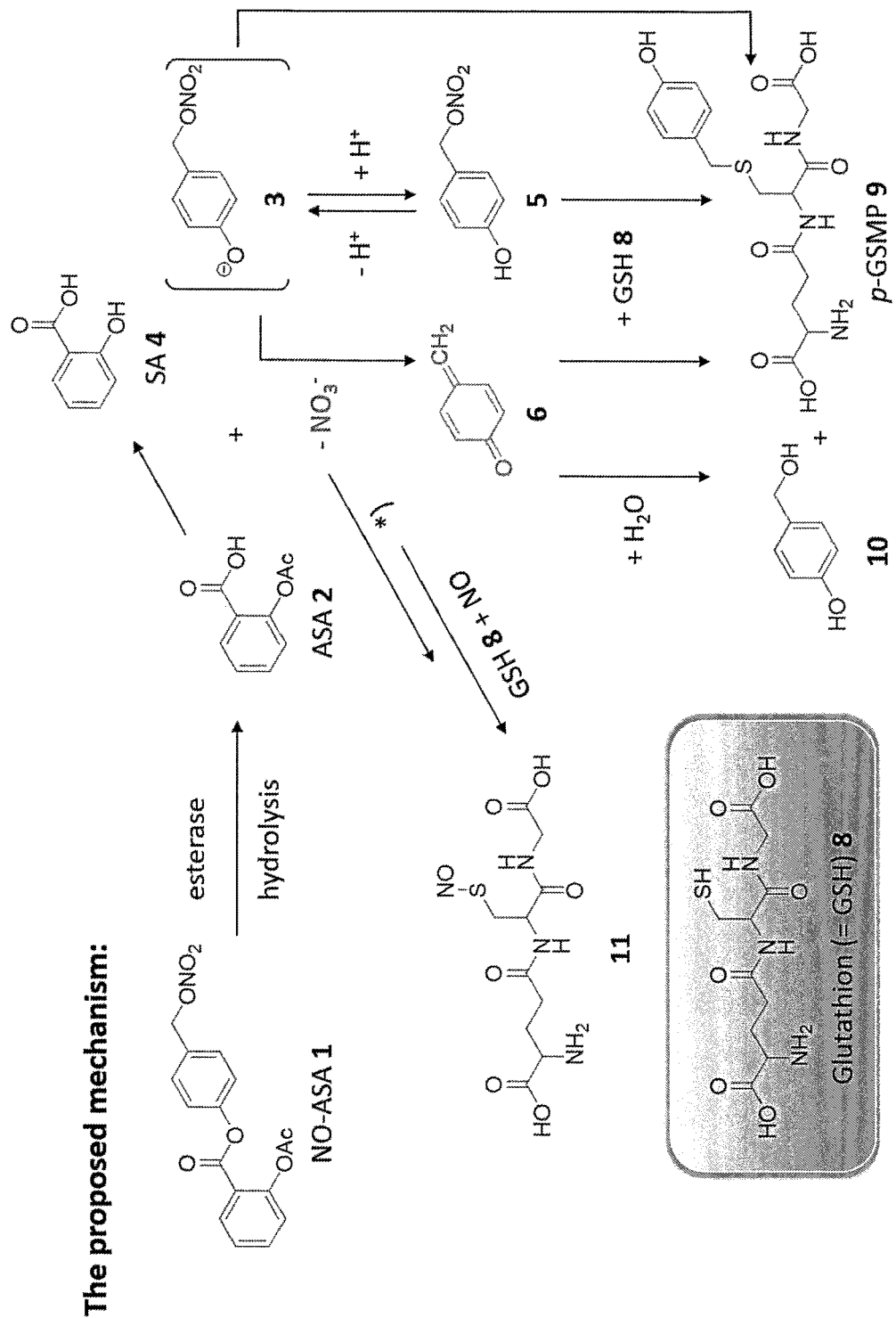

Figure 2 Bottom Part
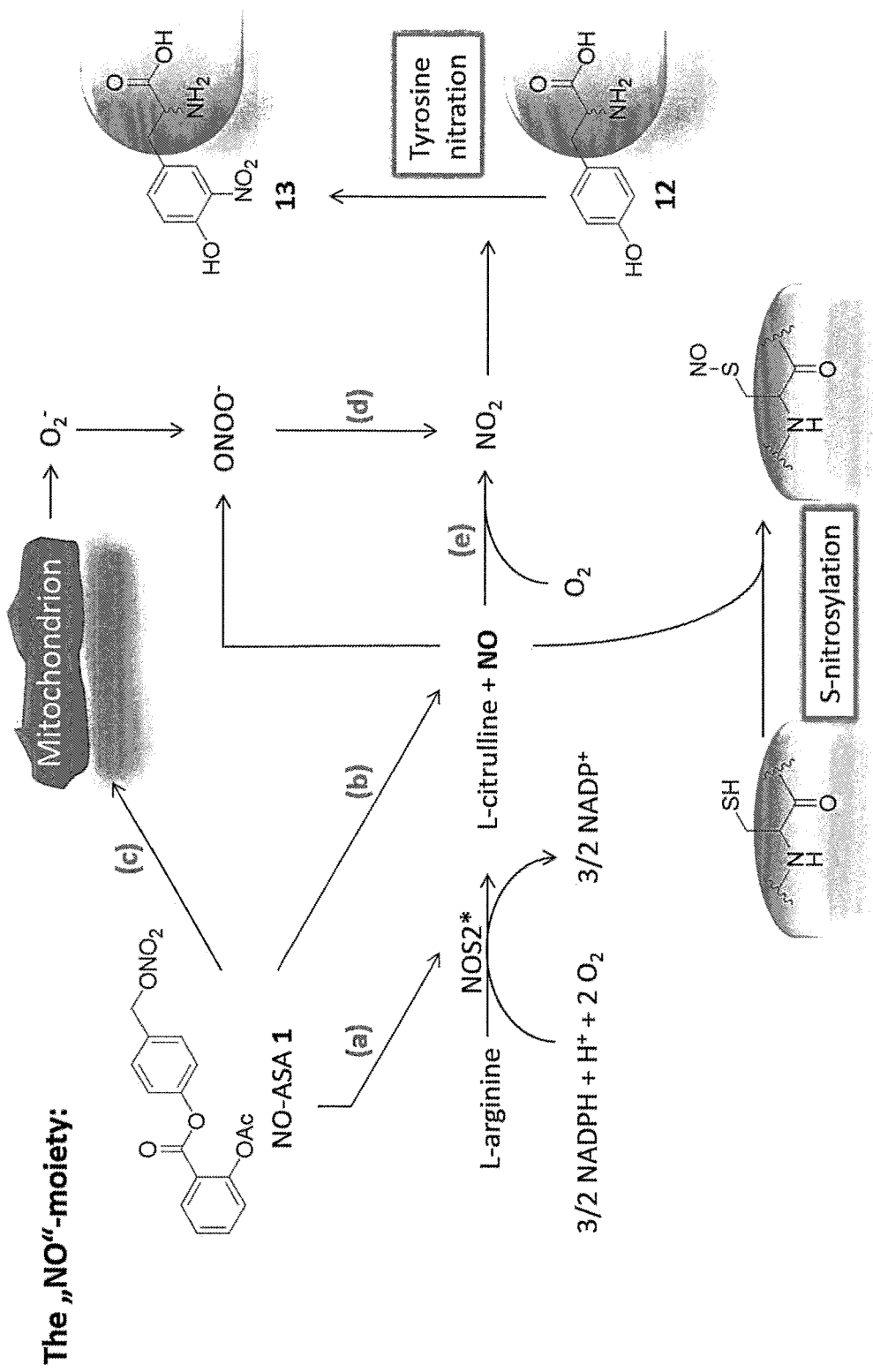

Figure 3 continuation
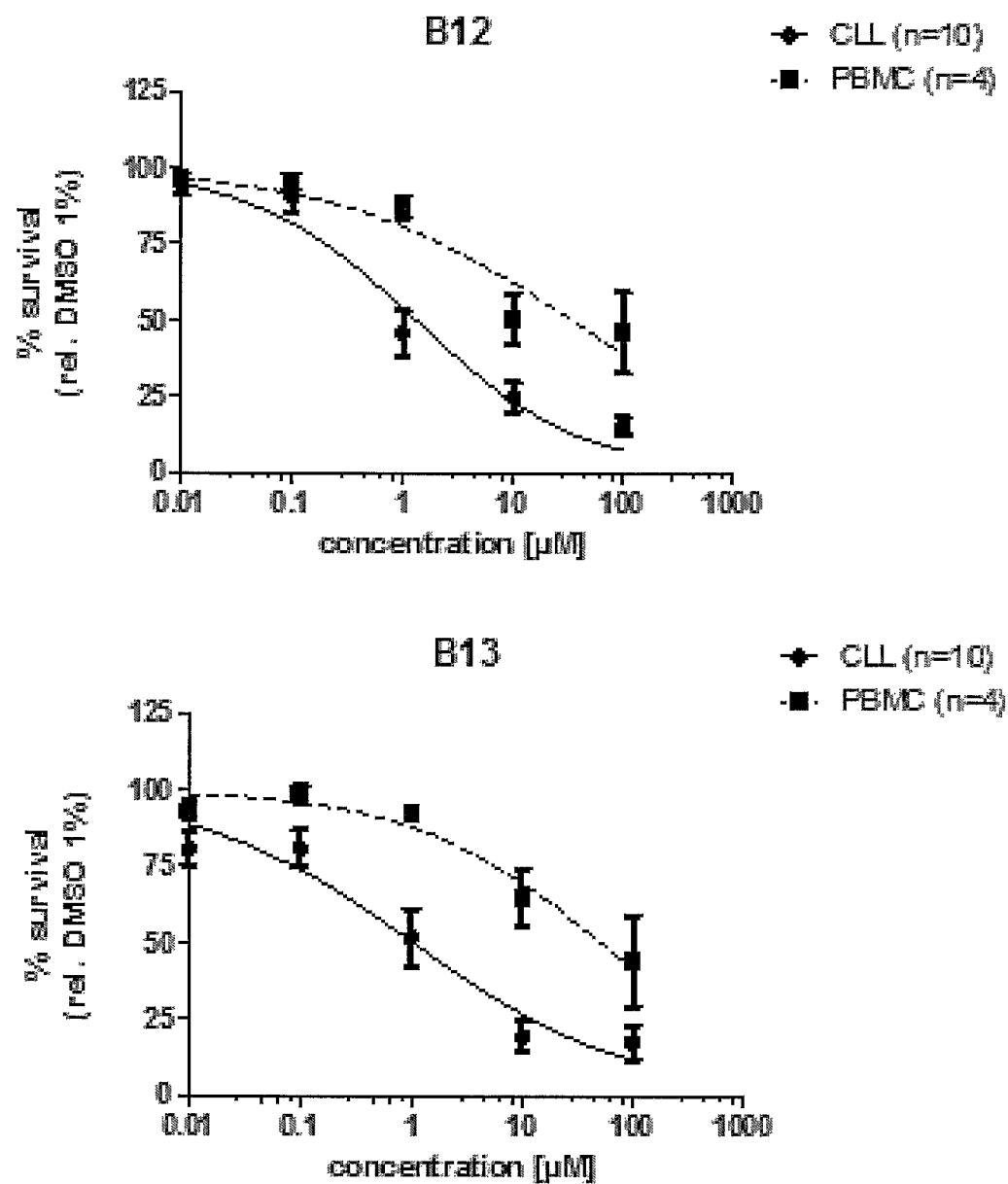

Figure 7 continuation
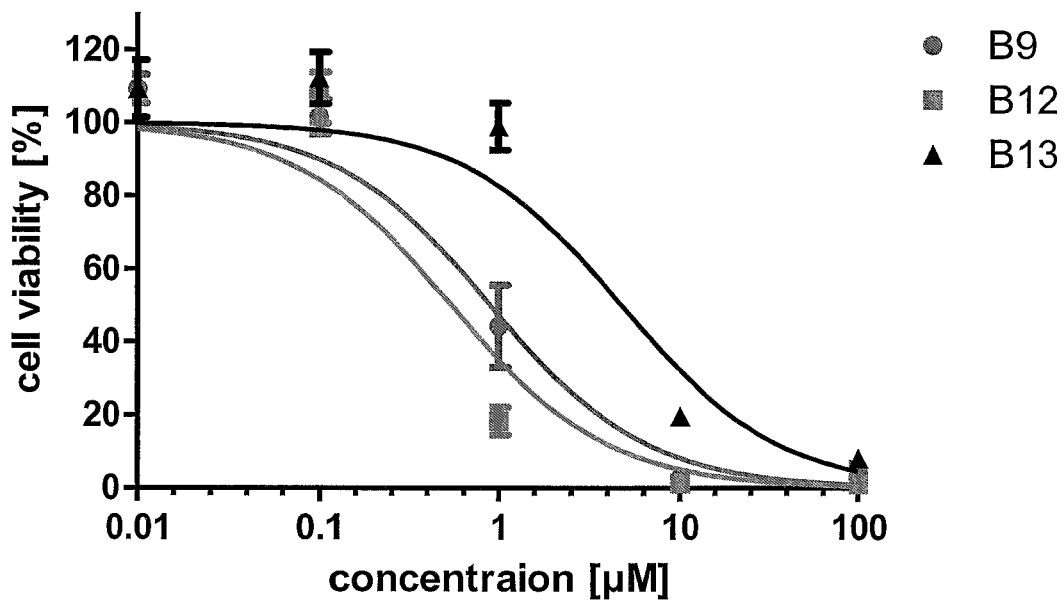
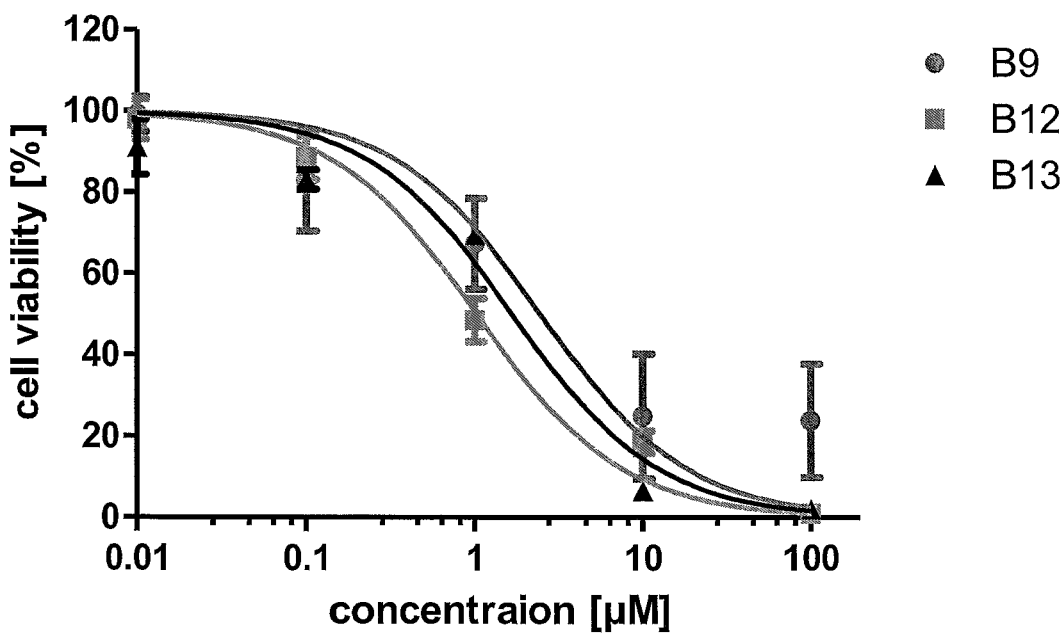

Figure 7 continuation
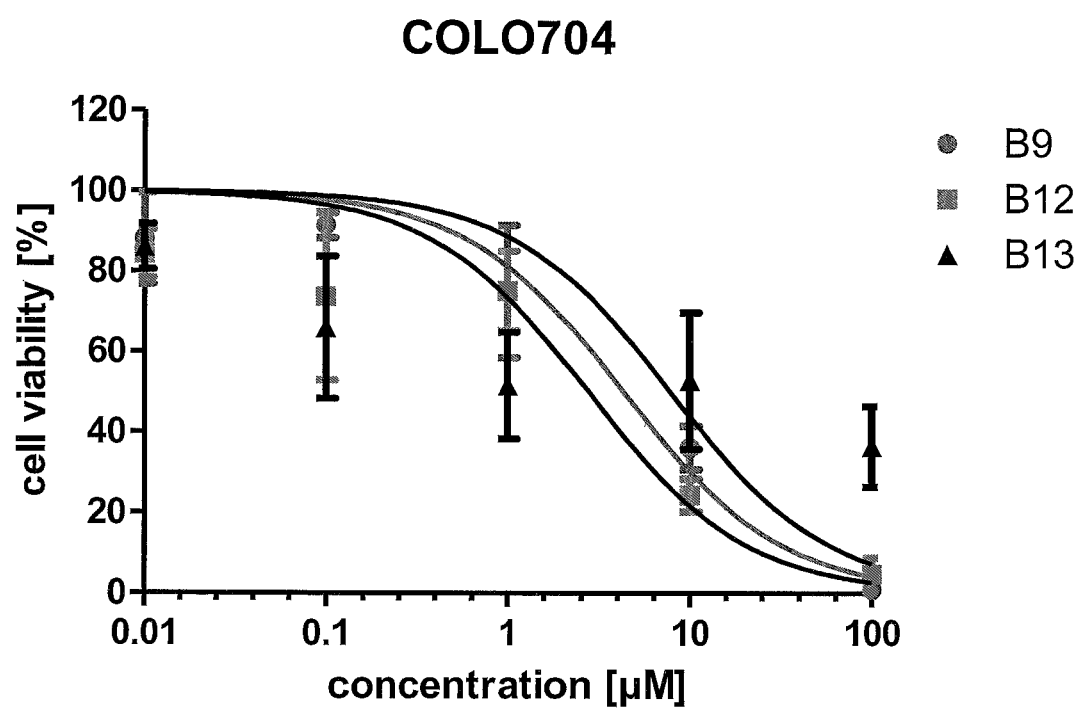

COMPOUNDS USEFUL IN THE TREATMENT OF NEOPLASTIC DISEASES

INCORPORATION BY REFERENCE TO ANY PRIORITY APPLICATIONS

This application is the U.S. National Phase of International Application No. PCT/EP2014/070328, filed Sep. 24, 2014, designating the U.S. and claiming priority to European Application No. 13 185 801.1, filed Sep. 24, 2013. Any and all applications for which a foreign or domestic priority claim is identified here or in the Application Data Sheet as filed with the present application are hereby incorporated by reference under 37 CFR 1.57.

FIELD OF THE INVENTION

The present invention refers to new compounds and pharmaceutically acceptable salts thereof, which are useful in the treatment of neoplastic diseases or proliferative disorders, a pharmaceutical composition comprising such a compound and a method for preparing these compounds.

BACKGROUND OF THE INVENTION

Chronic lymphocytic leukemia (CLL) is the most common adult leukemia in Western countries. The disease is very heterogeneous with some patients showing extremely slow progression while others proceed rapidly into advanced disease stages and require immediate treatment (Cramer, P. and Hallek, M. (2011), "Prognostic factors in chronic lymphocytic leukemia—what do we need to know?", Nat Rev Clin Oncol 8: 38-47). Despite considerable improvement of therapeutic strategies in the last decade, CLL remains incurable by conventional chemoimmunotherapies. The development of new treatment options remains an important goal.

Nonsteroidal anti-inflammatory drugs (NSAIDs) have been demonstrated to not only be useful in the treatment of pain, inflammation and fever, but also to possess a considerable antineoplastic effect (Thun et al. (2002), "Nonsteroidal anti-inflammatory drugs as anticancer agents: mechanistic, pharmacologic, and clinical issues", J. Natl Cancer Inst 94: 252-266; Shiff, S. J. and Rigas, B. (1999), "Aspirin for cancer", Nat Med 5: 1348-1349).

As for most of the classical NSAIDs, use as an anticancer agent is limited by mainly gastrointestinal and cardiovascular side effect at required concentrations (for a review see Ng, S. C. and Chan, F. K. (2010), "NSAID-induced gastrointestinal and cardiovascular injury", Curr Opin Gastroenterol 26: 611-617), so chemical modifications have been conducted. These modifications focused on the association of traditional NSAIDs with phospholipids, cyclodextrins, or chemical moieties that release gastroprotective mediators such as nitric oxide (NO) via an aliphatic, aromatic or heterocyclic spacer (for reviews see Abdel-Tawab, M. et al. (2009), "Nonsteroidal anti-inflammatory drugs: a critical review on current concepts applied to reduce gastrointestinal toxicity.", Curr Med Chem 16: 2042-2063) and Burgaud, J. L. et al., (2002), "Nitric-oxide releasing molecules: a new class of drugs with several major indications", Curr Pharm Des 8: 201-213). The pharmacokinetic and pharmacological properties of the final substance are largely dependent on the chemical structure of the spacer. NO-donating acetylsalicylic acid (NO-ASA) can be considered the classic NO-NSAID. Here, an aromatic spacer links the classical acetylsalicylic acid molecule to a NO-releasing moiety (—ONO$_2$) (Baron, J. A., (2003), "Epidemiology of non-steroidal anti-inflammatory drugs and cancer", Prog Exp Tumor Res 37: 1-24). It is believed that upon oral administration esterases rapidly cleave NO-ASA into ASA and the NO-releasing moiety linked to the spacer. Actual release of NO takes place in the subsequent metabolism of the spacer/NO-releasing complex (Wallace, J. L. et al. (2002), "Potential cardioprotective actions of NO-releasing aspirin", Nat Rev Drug Discov 1: 375-382).

Razavi, R. et al. describe in Clinical Cancer Research 17 (2), Jan. 15, 2011, on page 286 to 293 that para-NO-ASA induces cell apoptosis in CLL cells in vitro and could inhibit tumor growth in vivo. Furthermore, Gehrke, I. et al. discuss in Therapeutic Advance Hematology (2011) 2 (5), page 279 to 289 that the anti-neoplastic effect of NO-ASA in CLL cells is highly dependent on its positional isomerism, which is that the para-NO-ASA shows a much higher effect than the meta- or ortho-isomer.

WO 2005/065361 describes compounds and compositions for treating proliferative diseases, in particular cancer, by inhibiting the growth of dysproliferative cells. In this application several types of aromatic compounds are described, wherein among others NO-ASA and derivatives thereof are shown. Furthermore, WO 02/30866 describes nitrate-derivatives of aromatic compounds as drugs for diseases having an inflammatory basis, in particular diseases of the intestinal tract. Here again among others the isomers of NO-ASA are disclosed as effective compounds.

In document WO 01/04082 (nitrooxymethyl)phenyl esters of salicylic acid derivatives and methods for their preparation are disclosed.

Furthermore, WO 2009/023631 is disclosing compounds for treating diseases relating to inflammation, such as cancer, neurodegenerative and cardiovascular diseases are described, wherein said compounds include esters of aromatic derivatives.

In none of the prior art documents cited above, compounds described herein are disclosed, particularly it is not disclosed that said compounds can be used for treatment of neoplastic diseases of proliferative disorders.

SUMMARY OF THE INVENTION

The object of the present invention was to provide compounds acting as an effective and selective medicament for the treatment of neoplastic diseases or proliferative disorders, in particular compounds which induce selectively apoptosis of degenerated cells providing reduced side effects in living organisms.

This object is met when a compound according to the formula:

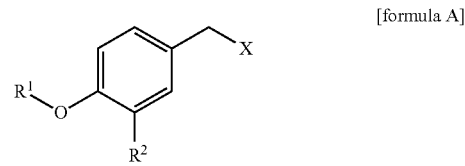

[formula A]

wherein R1 is selected from

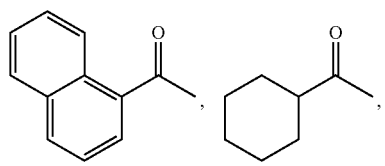

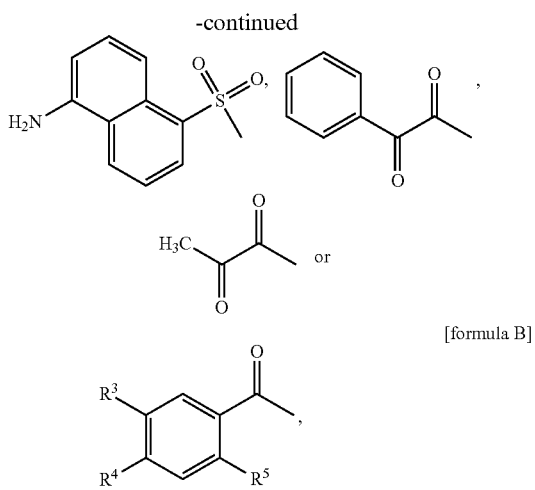

R2 is (C₁ to C₅)alkyl, (C₁ to C₅)alkoxy, (C₂ to C₄)alkenyl or alkinyl, azido(C₁ to C₄)alkyl, or hydrogen;

R3 is (C₁ to C₅)alkyl, (C₁ to C₃)alkyl with 1 to 3 halogen substituents, halogen or hydrogen;

R4 is (C₁ to C₅)alkyl, (C₁ to C₅)alkoxy, or hydrogen;

R5 is (C₁ to C₅)alkyl, (C₁ to C₅)alkoxy, acetoxy, halogen or hydrogen;

X is OTBS, hydroxy, formyloxy, acetoxy, nitrooxy, nitrooxymethyl, or a halogen; with the proviso that if R1 is [formula B], R2, R3 and R5 are hydrogen and X is hydroxyl R4 is not methoxy;

or a pharmaceutically acceptable salt thereof.
is used as a medicament, in particular the compound is suitable for use in the treatment of a neoplastic disease or a proliferative disorder. Although one of the compounds falling under the formula as defined above is disclosed in document WO 2001/021577 as a melanin-concentrating hormone antagonist, the compounds of the present invention are nowhere described as potential agents for the treatment of neoplastic diseases or (dys)proliferative disorders.

DETAILED DESCRIPTION OF THE INVENTION

Preferred embodiments are comprised in dependent claims and described below.

In formula (A) it is of particular interest that the residue-OR1 and —CH₂X are bound to the benzene ring in para-configuration.

The present invention is also directed to such a compound for the use of treatment of a neoplastic disease or a (dys-)proliferative disorder, wherein said disease or disorder is preferably a cancer. More preferably the cancer is selected from group consisting of prostate, pancreatic, lung, skin, breast, bladder, colon and blood cancer, wherein it is particularly preferred that the cancer is chronic lymphocytic leukemia (CLL).

In the compounds of the present invention it is preferred that by linkage to the residue R1 an ester group is obtained at benzene ring of formula A.

The compounds of the present invention effect an increased apoptosis of dysfunctional proliferative cells. Without being bound to the following theory, it is assumed that said increased apoptosis of the dysfunctional cells is due to the ability of the compounds of the present invention to form unusual derivatives of biologically active compounds within the cells, like for example derivatives of nucleic acid sequences (DNA, RNA), of amino acids, peptides or proteins, or compounds of signal pathways or biological pathways. The ester group of the compounds of the present invention can be cleaved by esterases inside the organisms/cells resulting in highly reactive compounds which are able to be added to the biological compounds usually present in a cell. The mechanism of building said reactive compounds and the formation of derivatives of biological compounds is exemplarily shown as a general overview in FIG. 1. The presence of the so formed derivatives increases the apoptosis of the cells comprising said derivatives and thus deleting the amount of dysfunctional cells. Details of said mechanisms as described in the literature are shown in FIG. 2.

The compounds of the present invention provide an increased selectivity to dysfunctional cells, in particular to cancer cells. The selectivity of the substances was analyzed in vitro via AnnexinV/Propidium iodide assay (PI) (apoptosis/cell death) with primary CLL cells and peripheral blood mononuclear cells (PBMCs). Differences of sensitivity between CLL cells and PBMCs towards a compound are referred to as selectivity. The underlying mechanism of the selectivity of NO-ASAs to cancer cells is thought to be due to inhibition of different signaling pathways, like the WNT or NFkappaB pathways, which are specifically important for cancer cell survival.

A high selectivity often indicates a reduced likelihood of adverse of target events and is therefore an important feature of modern chemotherapeutics. The actual toxicity and side effects of a drug is tested in subsequent animal experiments.

The present invention furthermore relates to a pharmaceutical composition comprising at least one of the compounds of the present invention or a pharmaceutically acceptable salt thereof, preferably in admixture with one or more pharmaceutically acceptable carriers.

Further, the present invention provides methods for the preparation of such compounds.

"Pharmaceutically acceptable salt" refers to those salts which retain the biological effectiveness and properties of the free bases or free acids and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, ascorbic acid and the like or with suitable bases or salts including, but not limited to, e.g. aluminum, calcium, lithium, magnesium, potassium, sodium, zinc, and diethanolamine salts. For a review on pharmaceutically acceptable salts see Berge et al., 66 J. PHARM. SCI. 1-19 (1977).

The term "treatment" as used herein covers any treatment of a disease in a mammal, particularly a human, and includes:
(i) preventing the disease from occurring in a subject which may be predisposed to the disease but has not yet been diagnosed as having it;
(ii) inhibiting the disease, i.e., arresting its development; or
(iii) relieving the disease, i.e., causing regression of the disease.

The term "neoplastic disease" or "(dys)proliferative disorder" as used herein is intended to cover disease states showing the formation of an abnormal mass of tissue as a result of neoplasia. Neoplasia is the abnormal proliferation of cells. Prior to neoplasia the cells often undergo an abnormal pattern of growth. The growth of neoplastic cells exceeds, and is not coordinated with, that of the normal tissue around it. The growth persists in the same excessive manner even after cessation of the stimuli. It usually causes a lump or tumor. Neoplasm may be benign, pre-malignant or malignant (cancer). A proliferative disease or "dys"proliferative disorder refers to a dysfunction of cells, wherein the coordinated proliferation (new development and growth or biological cells) is dis-regulated and the cell production and growth increases and exceeds the usual cell rate.

With "cancer" a disease state is referred to, where an uncontrolled growth of malignant cells results in a noticeable mass increase of tissue cells, often accompanied by crowding out the normal tissue. "Chronic lymphocytic leukemia" is a type of leukemia cancer. Leukemias are cancers of the white blood cells, wherein CLL effects B cell lymphocytes. B cells originate in the bone marrow, develop in the lymph nodes and normally fight infections by producing antibodies. In CLL, B cells grow out of control and accumulate in the bone marrow and blood, where they crowd out healthy blood cells.

The compounds of the present invention can be used as a medicament. Due to the affinity of the compounds to malignant cells the compounds of the present invention are suitable for the use in treatment of neoplastic diseases or proliferative disorders. Furthermore, the compounds have an effect in inflammatory diseases. The assumed main effect of the compounds of the present invention is the "marking" of biological cell molecules as described above, resulting in apoptosis of the cells including the marked compounds.

The compounds of the present invention show a good selectivity for cells with undue proliferation and are believed to be processed by esterasis resulting in the active components as shown in FIGS. 1 and 2.

In a preferred embodiment of the present invention the compounds which can be used as an effective medicament is as follows:

Compound having the formula:

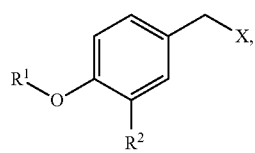

[formula A]

wherein R1 is selected from

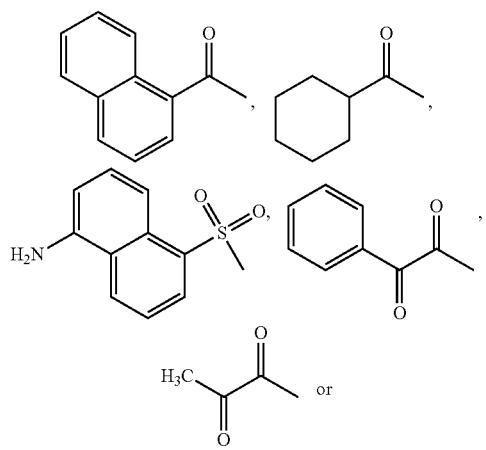

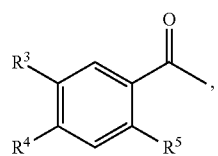

[formula B]

R2 is methoxy, ethinyl, azidomethyl, or hydrogen;

R3 is methyl, trifluoromethyl, fluorine, or hydrogen;

R4 is methyl, methoxy, or hydrogen;

R5 is acetoxy, methoxy, chlorine or hydrogen;

X is OTBS, hydroxy, formyloxy, nitrooxy, nitrooxymethyl, or chlorine; with the proviso that if R1 is [formula B], R2, R3 and R5 are hydrogen and X is hydroxyl R4 is not methoxy;

or a pharmaceutically acceptable salt thereof;

as a medicament.

Some compounds showing this formula are known in the prior art, however, they are not described as a medicament. However, most of the compounds, provided in the present application, are new compared to compounds known from the prior art, which are in particular compounds according to the formula:

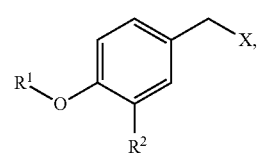

[formula A]

wherein R1 is selected from

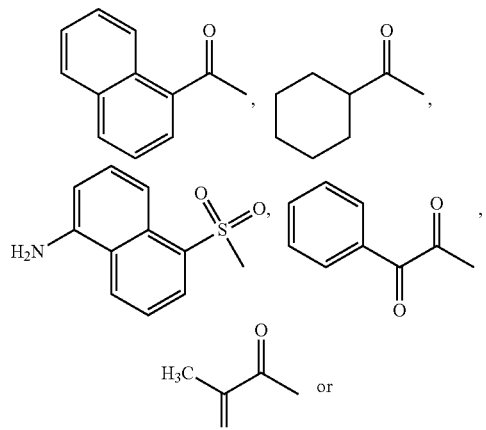

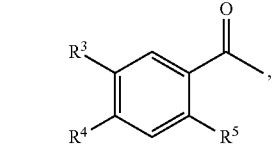

[formula B]

R2 is ($C_1$ to $C_5$)alkyl, ($C_1$ to $C_5$)alkoxy, ($C_2$ to $C_4$)alkenyl or alkinyl, azido($C_1$ to $C_4$)alkyl, or hydrogen;

R3 is ($C_1$ to $C_5$)alkyl, ($C_1$ to $C_3$)alkyl with 1 to 3 halogen substituents, halogen or hydrogen;

R4 is ($C_1$ to $C_5$)alkyl, ($C_1$ to $C_5$)alkoxy, or hydrogen;

R5 is ($C_1$ to $C_5$)alkyl, ($C_1$ to $C_5$)alkoxy, acetoxy, halogen or hydrogen;

X is OTBS, hydroxy, formyloxy, acetoxy, nitrooxy, nitrooxymethyl, or a halogen;

with the proviso that if R1 is [formula B], X is nitrooxy and R5 is acetoxy at least one of R2 to R4 is not hydrogen; with the proviso that if R1 is [formula B], R3 to R5 are hydrogen and X is hydroxyl R2 is not hydrogen and not methoxy; with the proviso that if R1 is [formula B], R2, R3 and R5 are hydrogen and X is hydroxyl R4 is not methoxy; with the proviso that if R1 is [formula B], R3 to R5 are hydrogen and X is OTBS R2 is not methoxy; and with the proviso that if R1 is methoxy and X is nitrooxy R2 is not hydrogen.

Under these a compound is preferred having formula (C),

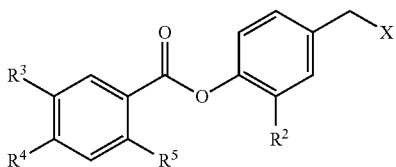

wherein

R2 is methoxy, ethinyl, azidomethyl, or hydrogen;

R3 is methyl, trifluoromethyl, fluorine, or hydrogen;

R4 is methyl, methoxy, or hydrogen;

R5 is acetoxy, methoxy, chlorine or hydrogen;

X is OTBS, hydroxy, formyloxy, nitrooxy, nitrooxymethyl, or chlorine;

with the proviso that if R1 is [formula B], X is nitrooxy and R5 is acetoxy at least one of R2 to R4 is not hydrogen; with the proviso that if R1 is [formula B], R3 to R5 are hydrogen and X is hydroxyl R2 is not hydrogen and not methoxy; with the proviso that if R1 is [formula B], R2, R3 and R5 are hydrogen and X is hydroxyl R4 is not methoxy; with the proviso that if R1 is [formula B], R3 to R5 are hydrogen and X is OTBS R2 is not methoxy; and with the proviso that if R1 is methoxy and X is nitrooxy R2 is not hydrogen.

From the compounds mentioned above such compounds are preferred wherein X is nitrooxy or OTBS, R2 is hydrogen, R3 to R5 are all hydrogen or R3 and R4 are methyl and R5 is acetoxy and/or wherein R1 is [formula B] R2 to R5 are all hydrogen and X is selected from OTBS, hydroxyl, nitrooxy, nitrooxy methyl, formyloxy, and chlorine.

In a particularly preferred embodiment of the present invention the compound is selected of the group consisting of 4-((nitrooxy)methyl)phenyl 2-actetoxy-5-methylbenzoate, 4-((nitrooxy)methyl)phenyl 2-actetoxy-5-fluorobenzoate, 4-((nitrooxy)methyl)phenyl 2-actetoxy-4-methylbenzoate, 4-(((tert-butyldimethylsilyl)oxy)methyl)phenyl 2-chloro-5-(trifluoromethyl)benzoate, 4-(hydroxymethyl)phenyl 2-chloro-5-(trifluoromethyl)benzoate, 4-((nitrooxy)methyl)phenyl 2-chloro-5-(trifluoromethyl)benzoate, 4-(((tert-butyldimethylsilyl)oxy)methyl)phenyl benzoate, 4-((nitrooxy)methyl)phenyl benzoate, 4-((formyloxy)methyl)phenyl benzoate, 2-methoxy-4-((nitrooxy)methyl)phenyl benzoate, 4-(chloromethyl)phenyl benzoate, 4-((nitrooxy)methyl)phenyl 1-naphthoate, 4-((nitrooxy)methyl)phenyl cyclohexane carboxylate, 4-((nitrooxy)methyl)phenyl 5-aminonaphthalene-1-sulfonate, 4-(2-(nitrooxy)ethyl)phenyl benzoate, 4-((nitrooxy)methyl)phenyl 2-methoxybenzoate, 4-((nitrooxy)methyl)phenyl 4-methoxybenzoate, 2-ethynyl-4-((nitrooxy)methyl)phenyl benzoate, 2-(azidomethyl)-4-((nitrooxy)methyl)phenyl benzoate, 4-((nitrooxy)methyl)phenyl 2-oxo-2-phenylacetate, and 4-((nitrooxy)methyl)phenyl 2-oxopropanoate or a pharmaceutically acceptable salt thereof.

The particularly preferred compounds according to the present invention are 4-((nitrooxy)methyl)phenyl-2-acetoxy-5-methyl benzoate, 4-((nitrooxy)methyl)phenyl-2-acetoxy-4-methyl benzoate, 4-((nitrooxy)methyl)phenyl benzoate, 4-((chloro)methyl)phenyl benzoate, 4-((nitrooxy)methyl)phenyl naphthoate wherein 4-((nitrooxy)methyl)phenyl benzoate and 4-((chloro)methyl)phenyl benzoate are particularly preferred. In particular such compounds are preferred having a high efficacy (low concentration is necessary for an effect, see table 1) and good chemical stability.

The term "alkyl" shall mean a straight, branched or cyclic alkyl group of the stated number of carbon atoms. Examples include, but are not limited to methyl, ethyl, n-propyl, iso-propyl, n-butyl, iso-butyl, sec-butyl, t-butyl, and straight and branched chain pentyl etc. or the according cyclic alkyls. In any case when a range between two limits is described it is meant that any value or integer in this range is disclosed. For example "$C_1$-$C_5$" means $C_1$, $C_2$, $C_3$, $C_4$ or $C_5$, a range from "1 to 3" means 1, 2 or 3, and a range between "0.1 and 1" means 0.1, 0.2, 0.3, 0.4, 0.5, 0.6, 0.7, 0.8, 0.9, or 1.

The term "alkoxy" means the bonding of an alkyl group via an oxygen, like for example methoxy, ethoxy, propoxy, iso-propoxy, butoxy (n-butoxy, iso-butoxy, sec-butoxy, t-butoxy), or pentoxy etc., the term "alkenyl" or "alkinyl" means alkyl residues having a double or a triple bond within the carbon chain.

The term "halo" or "halogen" means chlorine, flourine, bromine and iodine.

The methods used to synthesise the novel compounds of the present invention include the formation of a carbonic or sulphonic ester and the activated aliphatic or aromatic carbonic or suphonic acid is reacted with the compound according to the formula [D]:

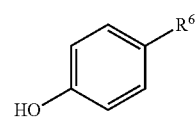

wherein R6 is methyl-X or formyl, X is as defined above.

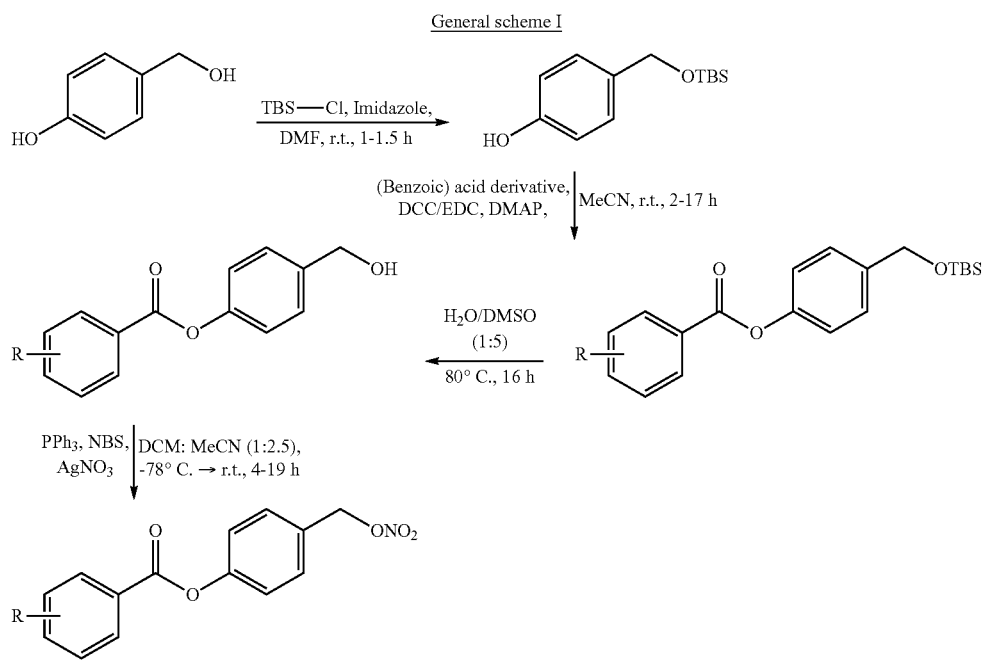

General scheme I

4-Hydroxybenzyl-tert-butyldimethylsilyl(TBS)ether was prepared by treatment of 4-hydroxybenzyl alcohol with TBS-Cl and imidazole. Bezoic acid derivatives, acetic acid or acid derivatives in general were esterified in a Steglich-like reaction (with DCC/EDC and DMAP) to form OTBS-bezoic acid (OTBS-BA).

NO-Dansyl (B16, see table 1 below) can be synthesised starting from the sulphonic acid chloride (dansyl chloride) to form the sulphonic acid ester. The following steps are as above (deprotetion and finally introducing the nitrate. The synthesis of ethyne-labelled compounds can start with the iodine substituted acid- or linker-building block. This substrate can be converted to the acetylene compound in a Sonogashira reaction to form with the corresponding counterpart the ester afterwards. Then deprotection of both silyl ethers and nitration follows to give the target molecules. All details of these procedures can be seen below in the Examples.

Abbrevations used in the schemes of the present application:

| Abbreviation | IUPAC name |
| --- | --- |
| TBS-Cl | tert-butylchlorodimethylsilane |
| DMF | N,N-dimethylformamide |
| r.t. | room temperature |
| DCC | N,N'-dicyclohexylcarbodiimide |
| EDC | 3-(ethyliminomethyleneamino)-N,N-dimethylpropan-1-amine |
| DMAP | 4-dimethylaminopyridine |
| DMSO | dimethyl sulfoxide |
| PPh$_3$ | triphenylphosphine |
| NBS | 1-bromo-2,5-pyrrolidinedione (N-Bromosuccinimide) |
| AgNO$_3$ | nitric acid silver(1+) salt (silver nitrate) |
| DCM | dichloromethane |
| MTBE | methyl tert.-butyl ether |
| MeCN | acetonitrile |

| Abbreviation | IUPAC name |
| --- | --- |
| Ac$_2$O | acetic anhydride |
| cat. | catalytic |
| SOCl$_2$ | sulfurous dichloride (thionyl chloride) |
| NaBH$_4$ | sodium tetrahydridoborate (sodium borohydride) |
| THF | oxolane (tetrahydrofuran) |
| DABCO | 1,4-diazabicyclo[2.2.2]octane |
| Ce(NH$_4$)$_2$(NO$_3$)$_6$ | diammonium cerium(IV) nitrate (ceric ammonium nitrate) |
| DIBAL-H | diisobutylaluminum hydride |
| TMS acetylene | ethynyltrimethylsilane (trimethylsilylacetylene) |
| PdCl$_2$(PPh$_3$)$_2$ | bis(triphenylphosphine)palladium(II) dichloride |
| CuI | copper(I) iodide |
| NEt$_3$ | triethylamine |

General scheme II

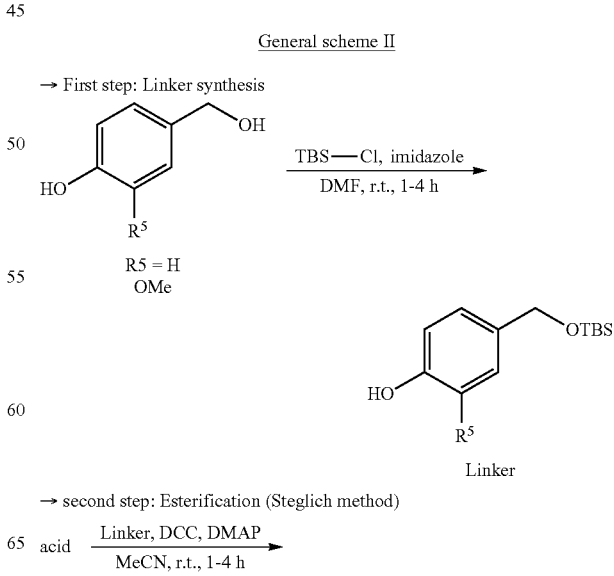

→ First step: Linker synthesis

R$^5$ = H
OMe

Linker

→ second step: Esterification (Steglich method)

acid $\xrightarrow{\text{Linker, DCC, DMAP}}{\text{MeCN, r.t., 1-4 h}}$

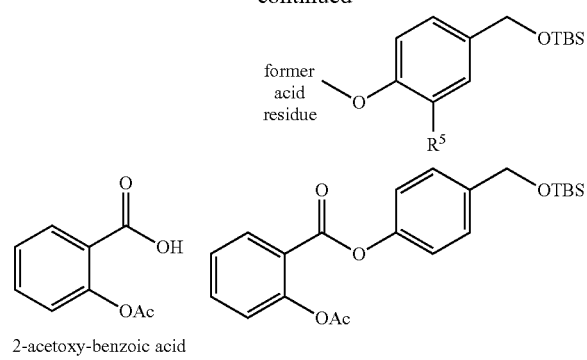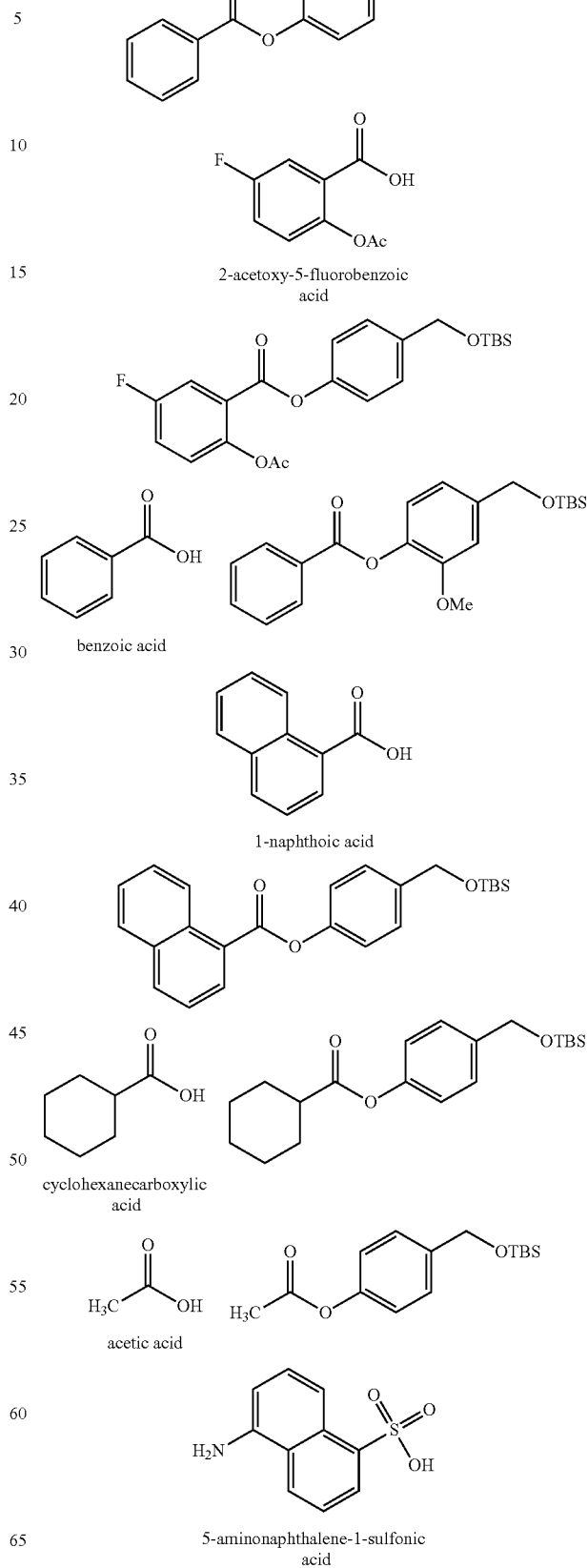

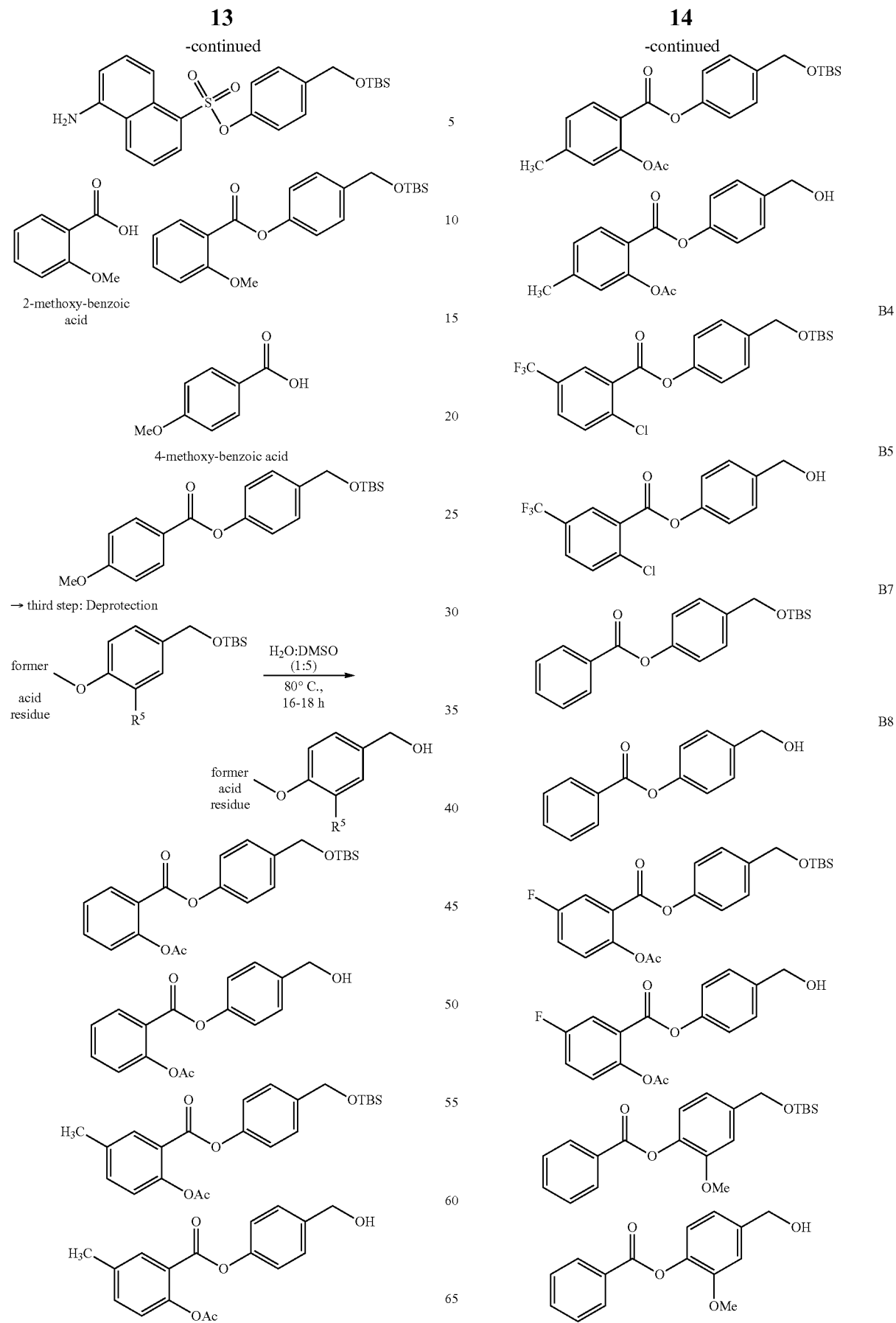

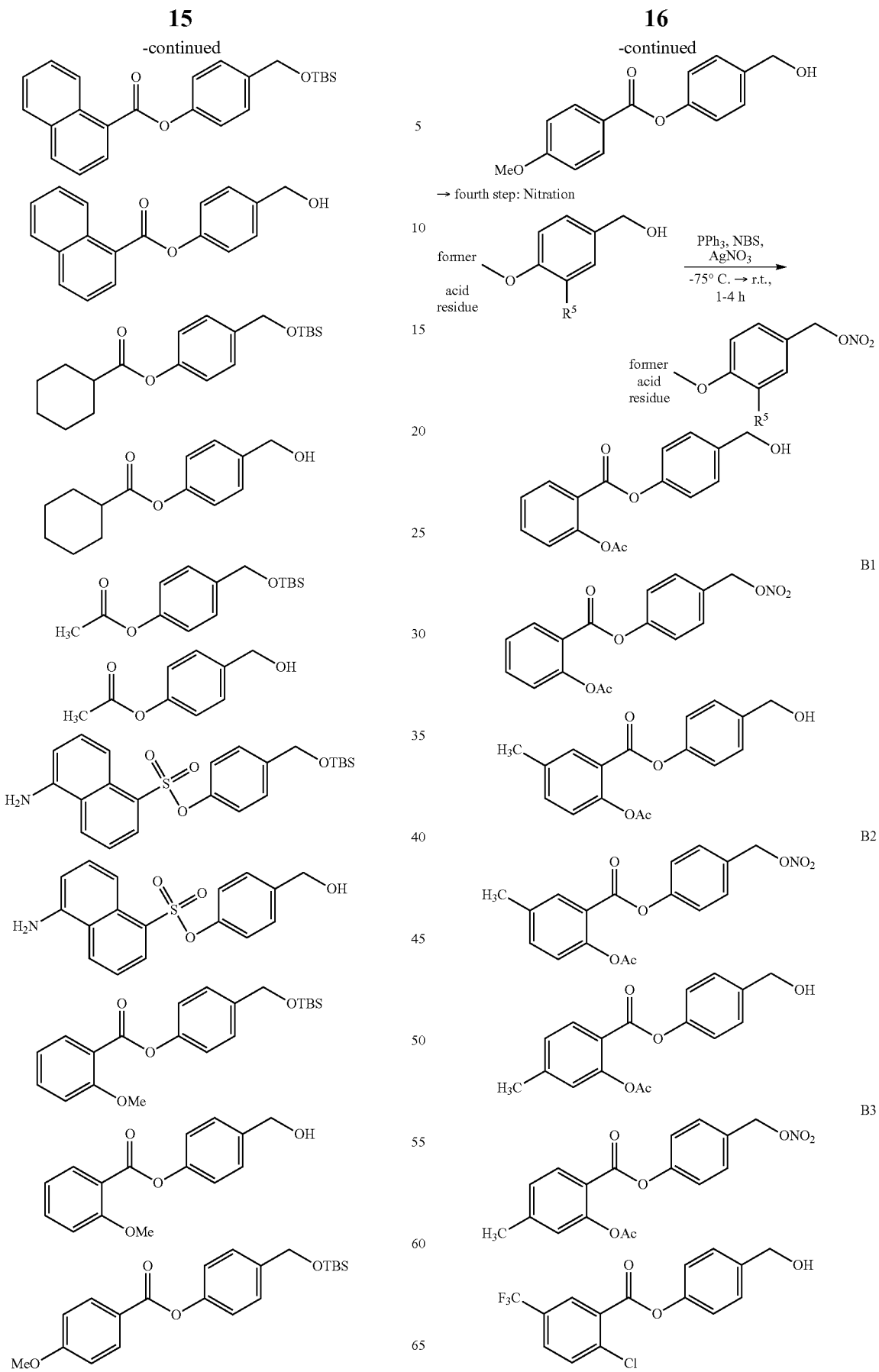

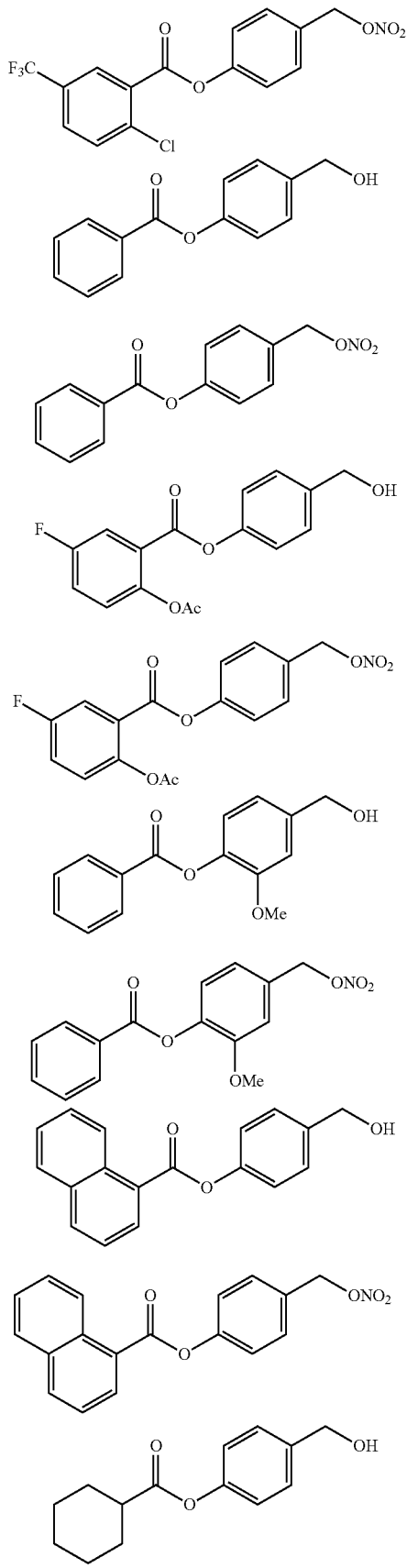
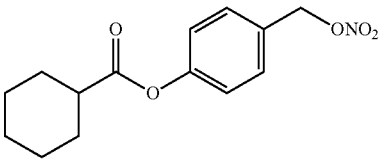
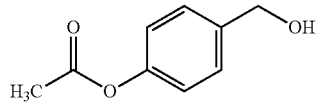
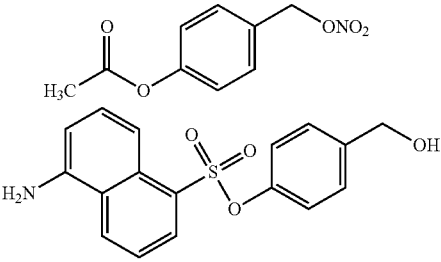
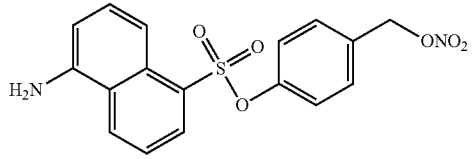
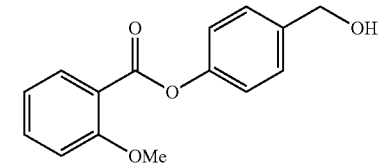
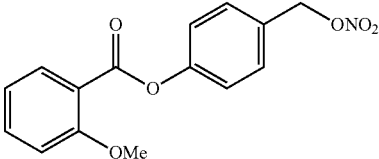
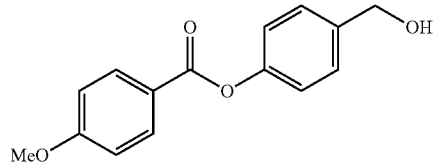
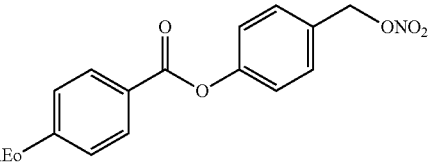
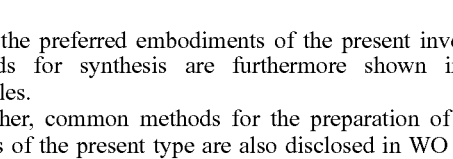

For the preferred embodiments of the present invention methods for synthesis are furthermore shown in the examples.

Further, common methods for the preparation of compounds of the present type are also disclosed in WO 2002/30866 and WO 2001/04082.

The compounds of the present invention are effective in decreasing further development of neoplasm or dysproliferative cells by increasing apoptosis of such cells. Due to the selectivity of these compounds the side effects in a living organism are decreased and therefore the compounds are suitable as pharmaceutical agents.

Accordingly, the compounds of this invention are useful for treating neoplastic diseases or (dys)proliferative disorders. In particular, the compounds of the present invention are effective in the treatment of cancer. The cancer, which can be effectively treated, is for example prostate, pancreatic, lung, skin, breast, bladder, colon, and blood cancer. In one particularly preferred embodiment the cancer which is treated is chronic lymphocytic leukemia (CLL).

Selectivity of the compounds for cells showing proliferative disfunction (like in neoplasm or in proliferative disorders) can be shown by in vitro experiments, in which a compound's ability to induce apoptosis and/or cell death or to reduce proliferation in disfunctional cells is compared to its impact on healthy control cells.

A compound which is known to be effective in the treatment of neoplastic diseases, particularly in the treatment of chronic lymphocytic leukemia (CLL) is 4-(nitrooxy) methyl phenyl-2-acetoxy benzoate, known as NO-ASA, see for example Gehrke, I. et al. in "Therapeutic Advances in Hematology" (2011) 2(5), pages 279 to 289. Thus, this compound is used as a reference in assays for the analysis of the compounds of the present invention concerning their effectivity, efficacy and effects on the disfunctional cells.

Experimental evidence indicates that the compounds of the present invention are useful in the treatment of neoplastic diseases or (dys)proliferative disorders due to the increased apoptosis of disfunctional cells after the addition of said compounds in an in vitro assay described in Example 1. The results of such assays are shown in FIG. 3 for the compounds B1 (control reference NO-ASA), B9, B12 and B13 (see table 1).

FIG. 3 shows a higher sensitivity of CLL cells towards the four drugs when compared to PBMCs. The drugs B1, B9, B12 and B13 are therefore selective for CLL cells. Relevant for the assessment of the selectivity is the ratio of the $ED_{50}$ for PBMCs and CLL cells (see table 1).

In the assays carried out with compounds of the present invention it becomes clear that the compounds have a clear effect on the disfunctional cells, wherein some of the compounds were particularly potent to increase cell apoptosis and thus decrease the development of malignant tumor cells.

In Table 1 shown below the preferred compounds are listed, wherein the compounds showing the lowest $EC_{50}$ (effective contration 50%) on CLL cells while remaining relatively untoxic for PBMCs in the AnnexinV/PI assay are the most preferred compounds. As can be seen from the below table, the compound determined as "B9" shows a very high effect in the AnnexinV assay and therefore is the most preferred compound of the present invention. Furthermore, the compounds "B9", "B12" and "B13" as well are preferred due to their high effect in the AnnexinV/PI assay. However, it should be particularly pointed out that not only the effect in the AnnexinV/PI assay is relevant for the preference of the compound, but furthermore their stability, compatibility, the development of side effects and their selectivity, and therefore as well compounds showing a higher value in the AnnexinV/PI assay compared to NO-ASA might be preferable compounds due to other positive effects.

All the compounds described in the present application and claimed in the appending claims can be used as medicament, in particular for the treatment of a neoplastic disease or a (dys)proliferative disorder. In particular, all these compounds as well as NO-ASA are effective medicaments for the treatment of cancer, wherein the treatment of CLL is particularly preferred.

In applying the compounds of this invention to the treatment of the above conditions, administration of the active compound and salts described herein can be via any of the accepted modes of administration, including oral, parenteral and otherwise systemic route of administration. Any pharmaceutically acceptable mode of administration can be used, including solid, semi-solid or liquid dosage forms, such as, for example, tablets, suppositories, pills, capsules, powders, liquids, suspensions, or the like, preferably in unit dosage forms suitable for single administration of precise dosages, or in sustained or controlled release dosage forms for the prolonged administration of the compound at a predetermined rate. The compositions will typically include a conventional pharmaceutical carrier or excipient and at least one of the compounds of the present invention or the pharmaceutically acceptable salts thereof and, in addition, may include other medicinal agents, pharmaceutical agents, carriers, adjuvants, etc.

The amount of one of the derivatives of the present invention administered will of course be dependent on the subject being treated, the severity of the affliction, the manner of administration and the judgment of the prescribing physician. However, an effective dose for oral, parenteral and otherwise systemic routes of administration is in the range of 0.01-100 mg/kg/day, preferably 0.1-50 mg/kg/day. For an average 70 kg human, this would amount to 0.7-7000 mg per day, or preferably 7-3500 mg/day.

One of ordinary skill in the art of treating such diseases will be able, without undue experimentation and in reliance upon personal knowledge and the disclosure of this application, to ascertain a therapeutically effective amount of one of the inventive compounds for a given disease.

For solid compositions, conventional non-toxic solid carriers include, for example, pharmaceutical grades of mannitol, lactose, cellulose, cellulose derivatives, sodium crosscarmellose, starch, magnesium stearate, sodium saccharin, talcum, glucose, sucrose, magnesium carbonate, and the like may be used. The active compound as defined above may be formulated as suppositories using, for example, polyalkylene glycols, e.g PEG (polyethyleneglycol) or PEG derivatives, acetylated triglycerides and the like, as the carrier. Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. The composition or formulation to be administered will, in any event, contain a quantity of the active compound(s) in an amount effective to alleviate the symptoms of the subject being treated.

Dosage forms or compositions containing one of the present compounds in the range of 0.25 to 95% by weight with the balance made up from non-toxic carrier may be prepared.

For oral administration, a pharmaceutically acceptable non-toxic composition is formed by the incorporation of any of the normally employed excipients, such as, for example pharmaceutical grades of mannitol, lactose, cellulose, cellulose derivatives, sodium crosscarmellose, starch, magnesium stearate, sodium saccharin, talcum, glucose, sucrose, magnesium, carbonate, and the like. Such compositions take the form of solutions, suspensions, tablets, pills, capsules, powders, sustained release formulations and the like. Such compositions may contain 1 to 95% by weight of one of the compounds of the present invention, more preferably 2 to 50% by weight, most preferably 5 to 8% by weight.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, triethanolamine sodium acetate, etc.

Transdermal or "pulsed" transdermal administration may be supported by cremes, gels, dispersions and the like.

A more recently devised approach for parenteral administration employs the implantation of a slow-release or sustained-release system, such that a constant level of dosage is maintained (see, e.g., U.S. Pat. No. 3,710,795).

The percentage of active compounds contained in such parental compositions is highly dependent on the specific nature thereof, as well as the activity of the compound and the needs of the subject. However, percentages of one of the inventive compounds of 0.1 to 10% by weight in solution are employable, and will be higher if the composition is a solid which will be subsequently diluted to the above percentages. Preferably the composition will comprise 0.2 to 2% by weight of one of the compounds in solution.

Preferably the pharmaceutical composition is administered in a single unit dosage form for continuous treatment or in a single unit dosage form ad libitum when relief of symptoms is specifically required.

FIGURES

Figure 1:
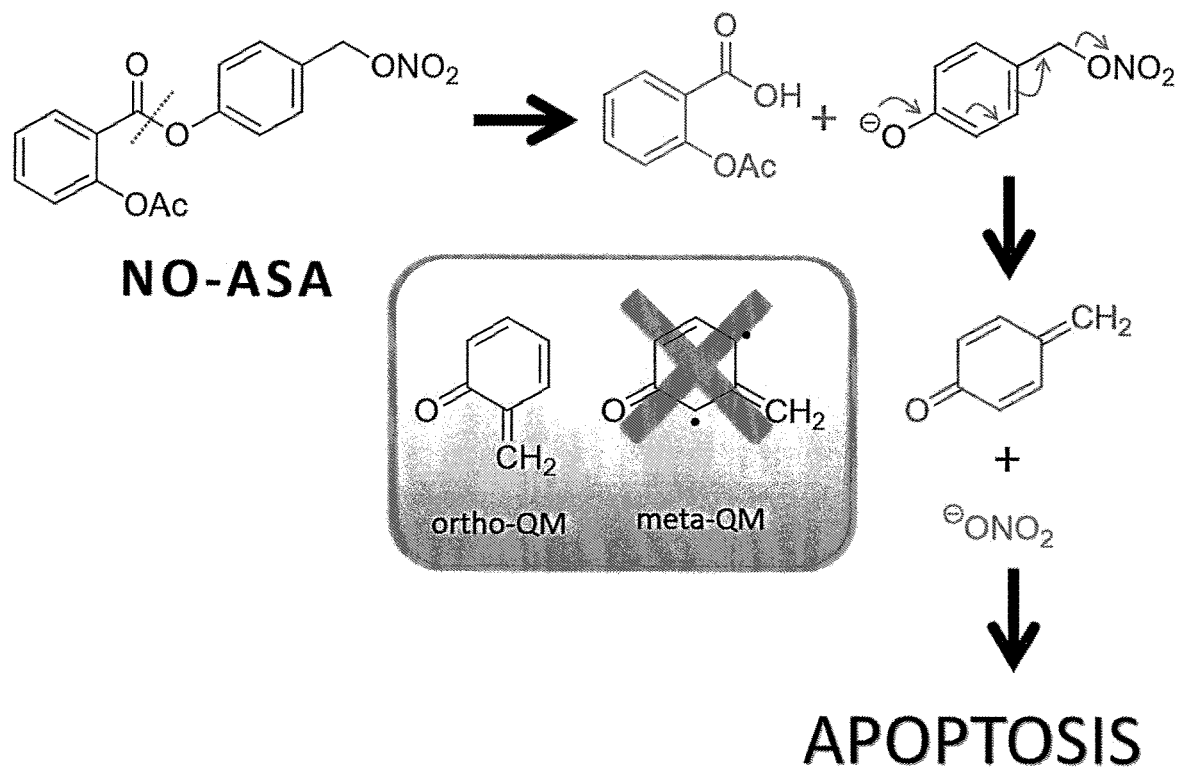
FIG. 1 is a very general scheme of the assumed mechanisms a pharmaceutically active agent effects in a proliferative cell.
Figure 1:
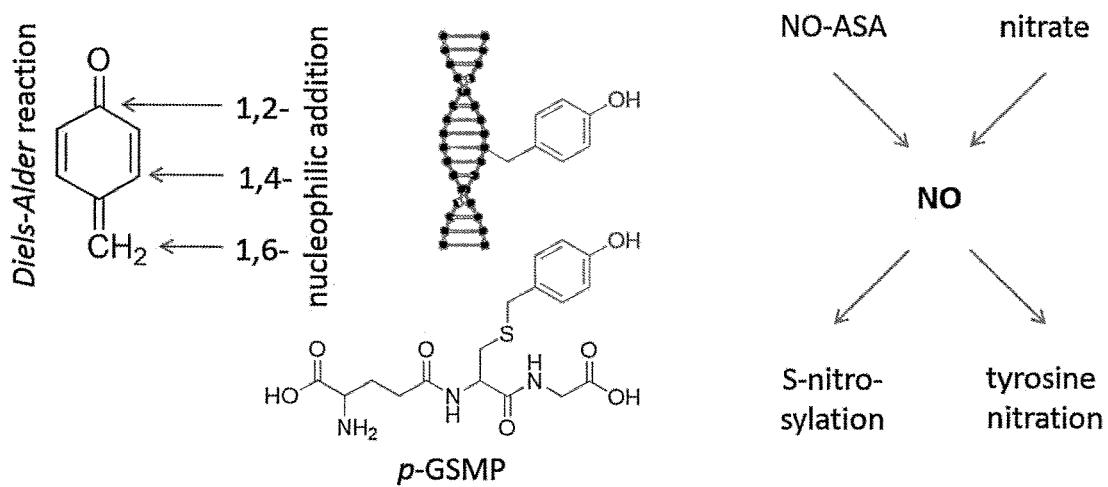
Figure 2:
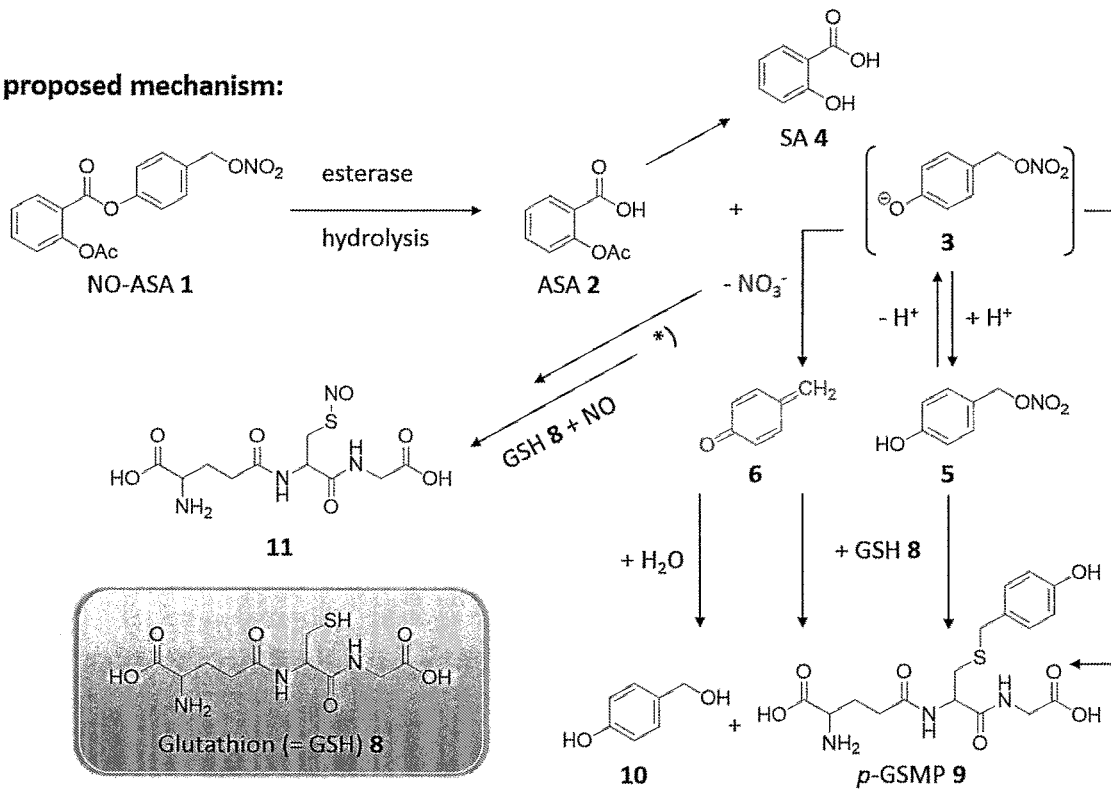
FIG. 2 shows the assumed mechanism as described in the literature of the provision of the pharmaceutically active agent, in particular quinone methide (upper part), or in particular $NO_x$ (lower part), effecting apoptosis in the cell.
Figure 2:
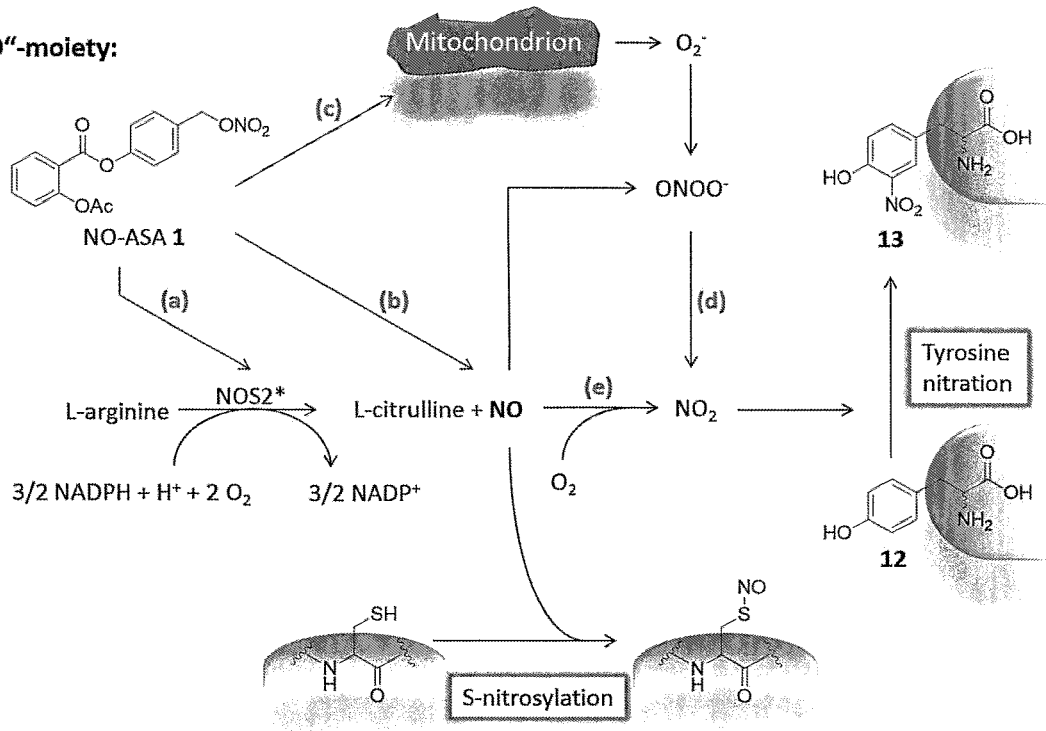
Figure 3:
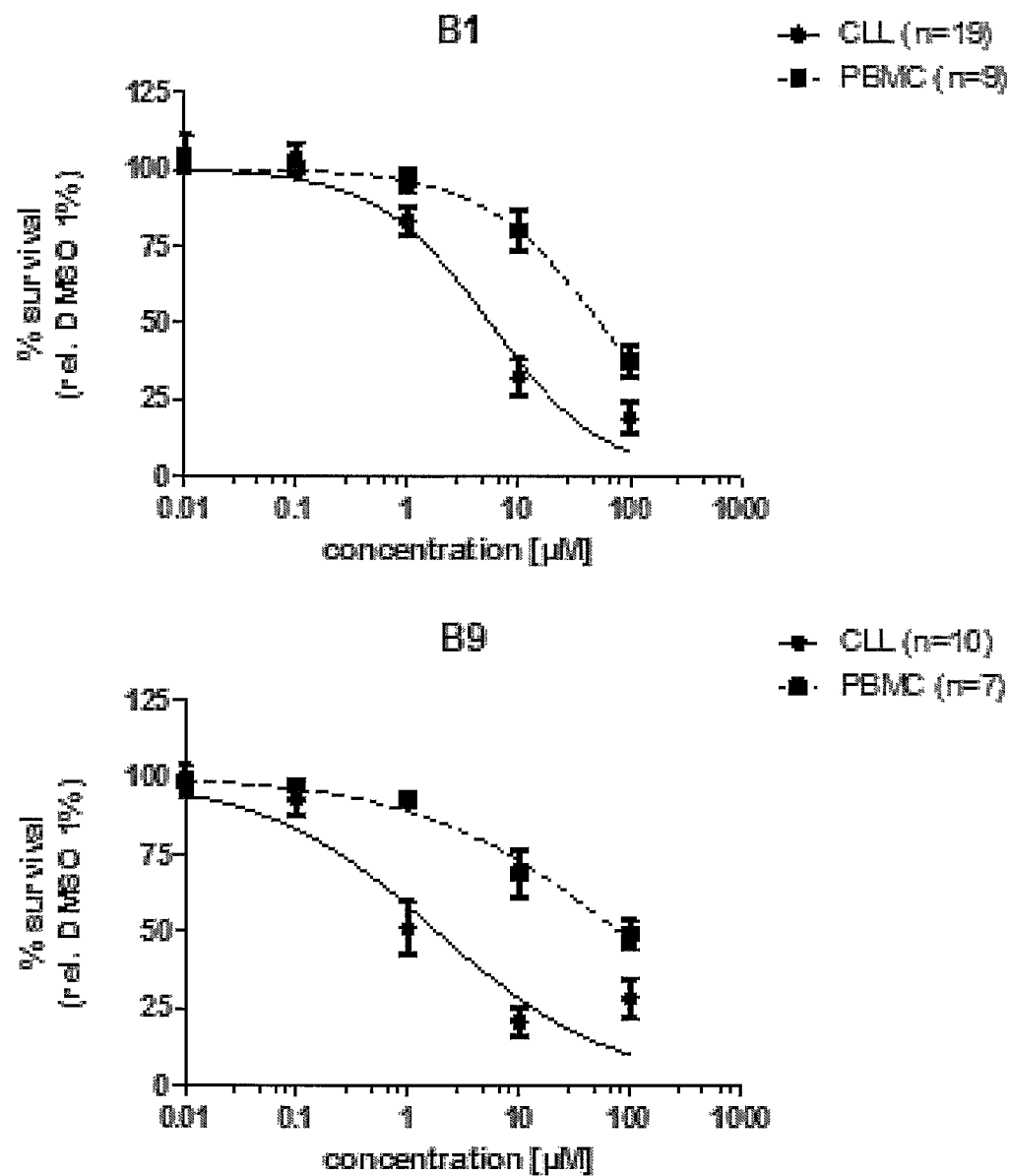

FIG. 3 shows the impact of compounds B1(control agent NO-ASA), B9, B12 and B13 (see table 1) on survival of primary PBMCs from healthy donors or CLL cells. PBMCs or CLL cells ($5*10^6$ cells/ml) were incubated for 24 h with different compounds at concentrations from 0.01 to 100 µM. Cell survival was normalized to DMSO control [vehicle]. See Example 1.

Figure 4:
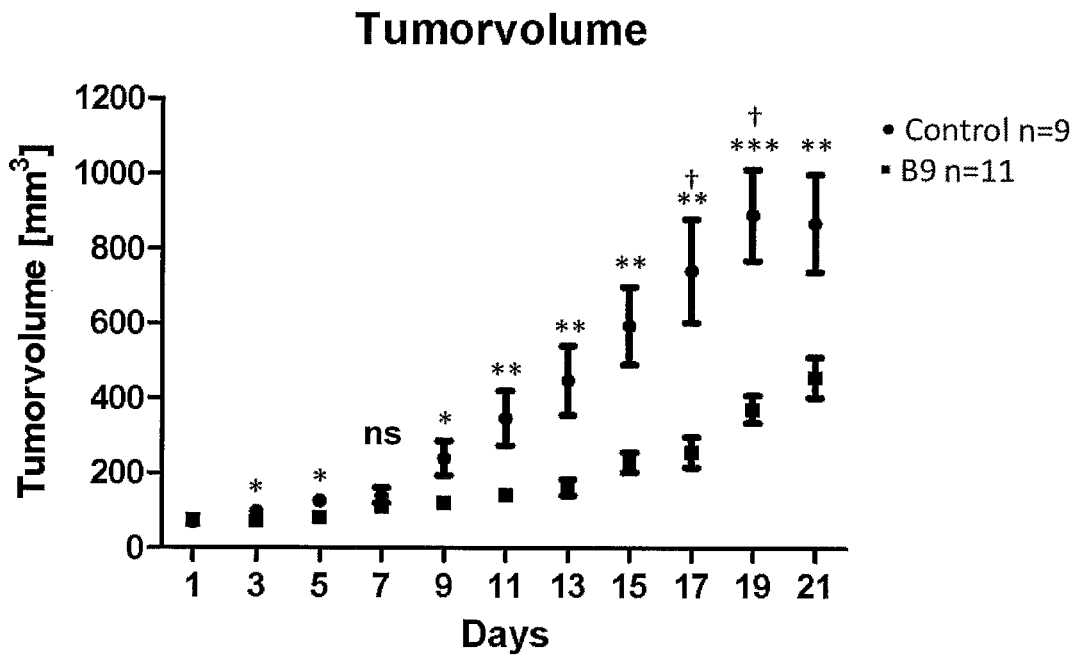

FIG. 4 shows the Inhibition of tumor growth by compound B9 in CLL xenografts (see Example 2). Treatment with B9 leads to significant tumor inhibition compared to vehicle control (p=0.015) after nine days with increasing significance up to day 19 of treatment (p=0.0003). $IR_{max}$ value of 65% for B9 over vehicle control was determined.

*=p≤0.05, =p≤0.01, *=p≤0.001 calculated by unpaired two-tailed students test, †=death, IR=Inhibition ratio.

Figure 5:
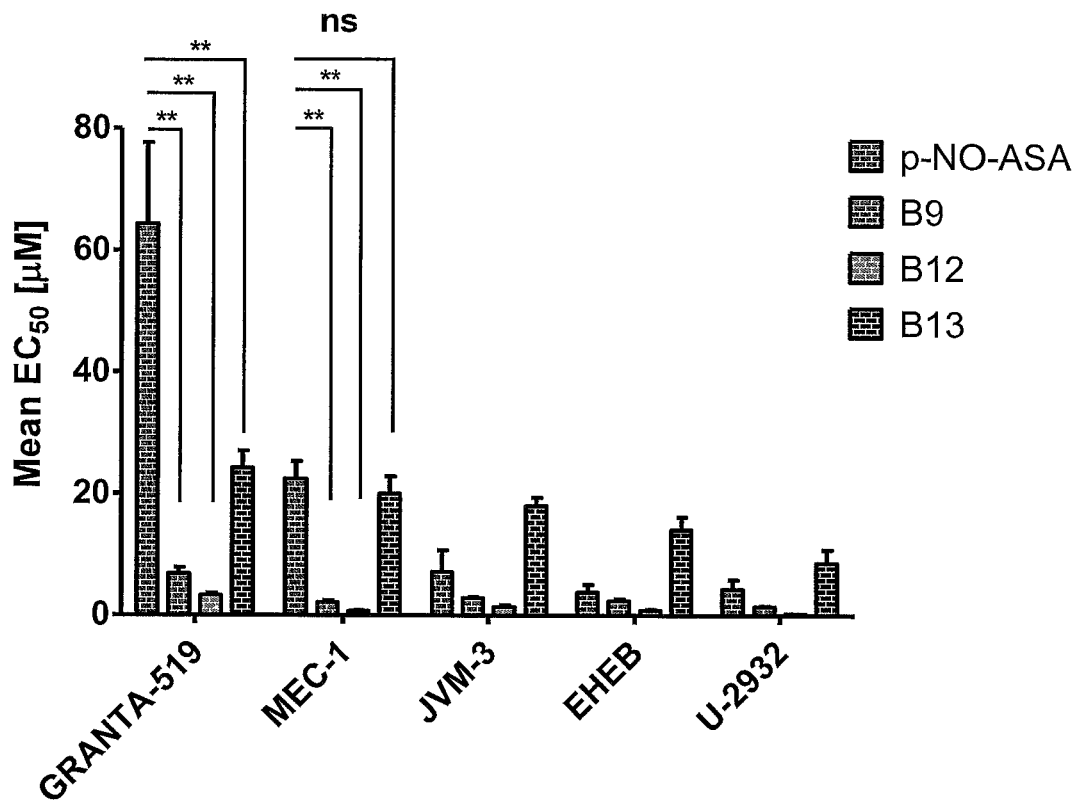

FIG. 5 shows that compounds B9 and B12 have superior cytotoxic effects on cell lines harboring bad prognosis (see Example 3). Several cell lines (n=5) were treated with different concentrations of p-NO-ASA, B9, B12 and B13 ranging between 0.01 µM and 1000 µM for 24 hours followed by addition of luminogenic CellTiter-Glo®-reagent. Para-NO-ASA, B9, B12 and B13 reduced ATP content in JVM-3, U2932 and EHEB cell lines likewise significantly, whereas para-NO-ASA is significantly less effective in MEC-1 and GRANTA-519 cell lines. For each cell line the order of used compound in the bar chart is from left to right as following: p-NO-ASA, B9, B12, B13.

Figure 6:
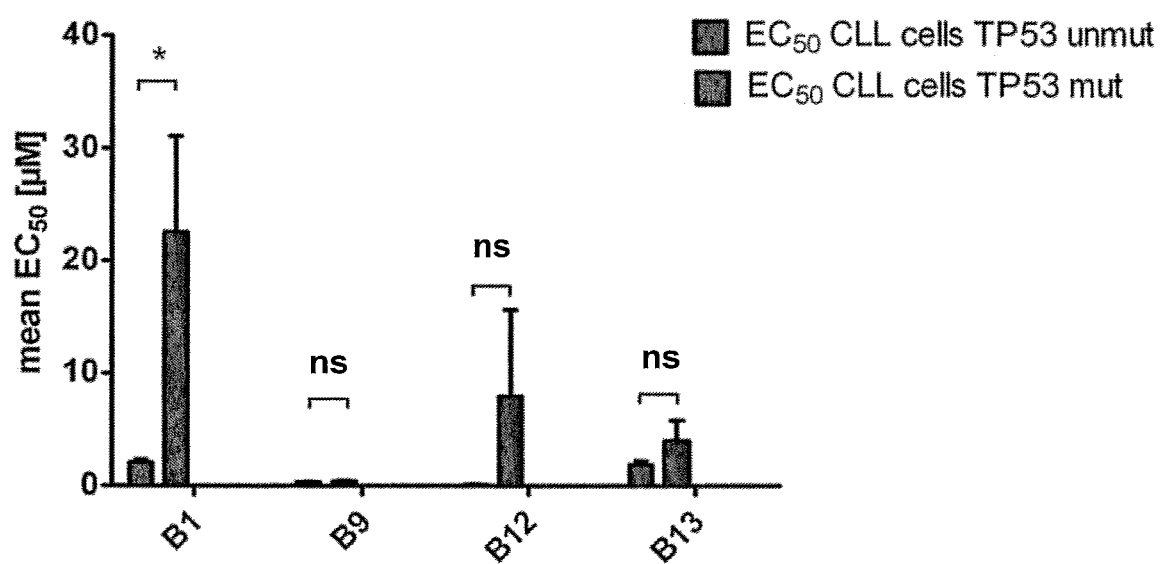

FIG. 6 shows the growth inhibition of CLL cells with and without a TP53 mutation by p-NO-ASA and the derivatives B9, B12, B13 (see Example 4). Isolated, primary CLL cells were treated for 24 h with the $EC_{50}$ of the different compounds and the ATP-content was measured by flow cytometry. For each used compound the order of mean $EC_{50}$ concentrations in the bar chart is from left to right as following: $EC_{50}$ CLL cells TP53 unmut (unmutated=without mutation), $EC_{50}$ CLL cells TP53 mut (mutated=with mutation).

Figure 7:
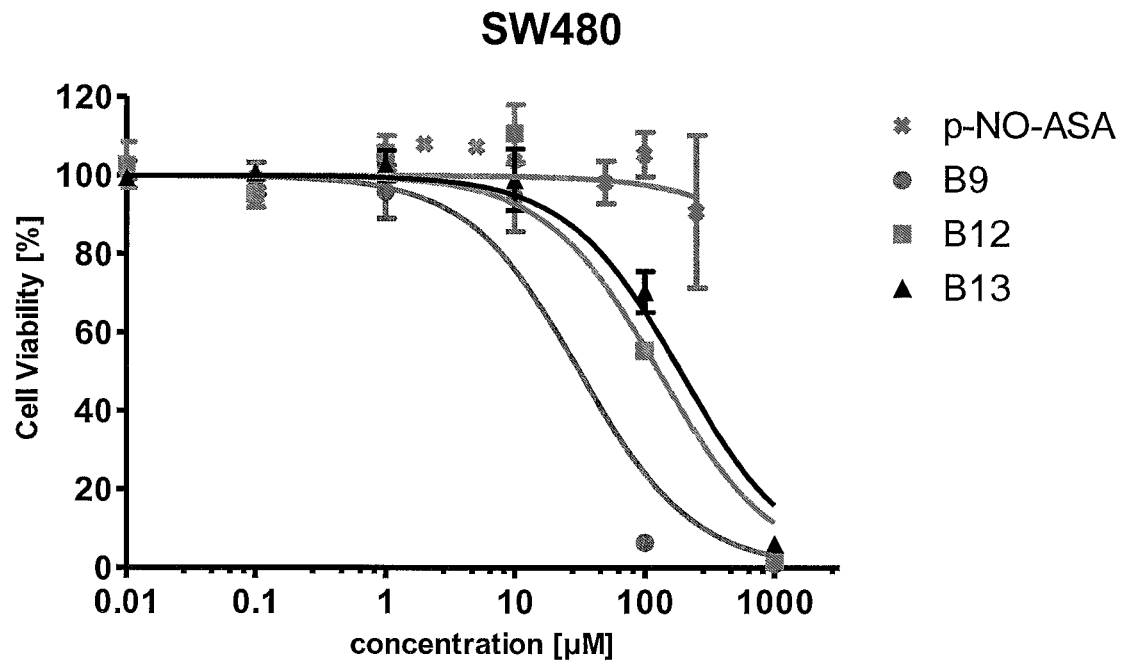
Figure 7:
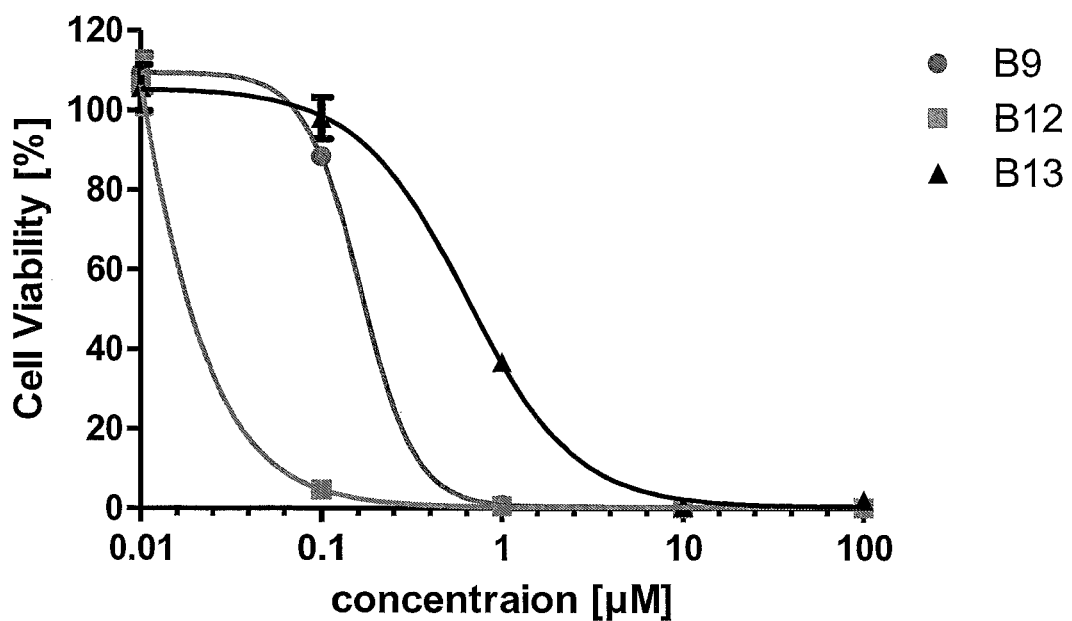

FIG. 7 depicts that compounds B9, B12 and B13 show superior cytotoxic effects on the colon cancer cell line SW480 compared to p-NO-ASA. The cell lines (n=5) were treated with different concentrations of p-NO-ASA, B9, B12 and B13 ranging between 0.01 µM and 100 µM for 24 hours followed by addition of luminogenic CellTiter-Glo®-reagent (see Example 5).

Figure 8:
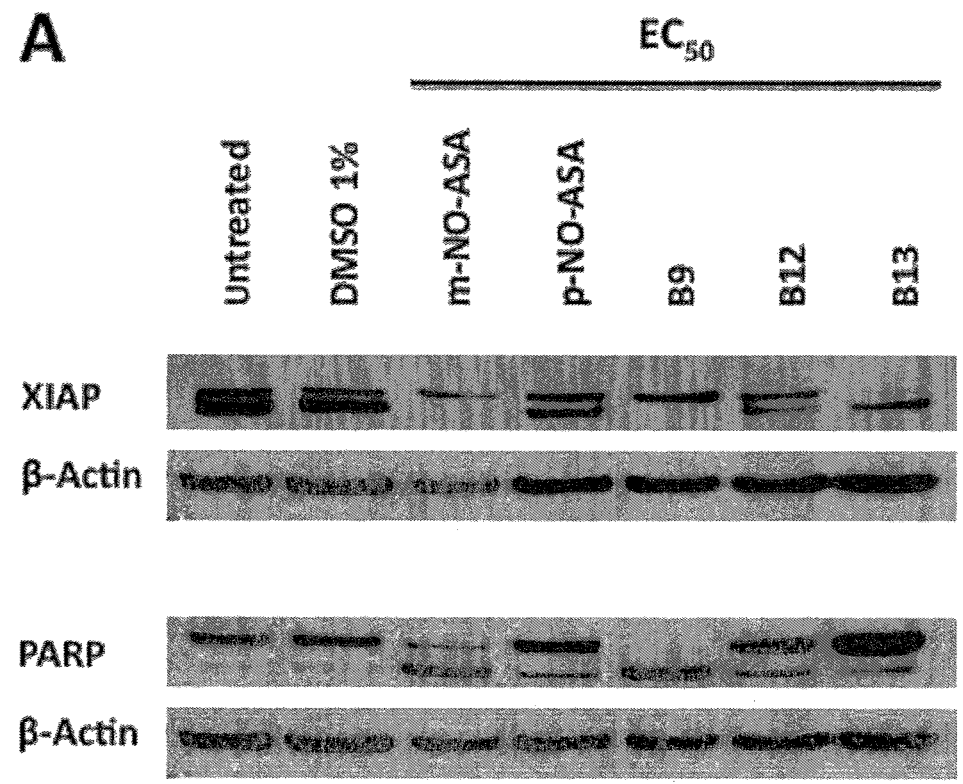
Figure 8:
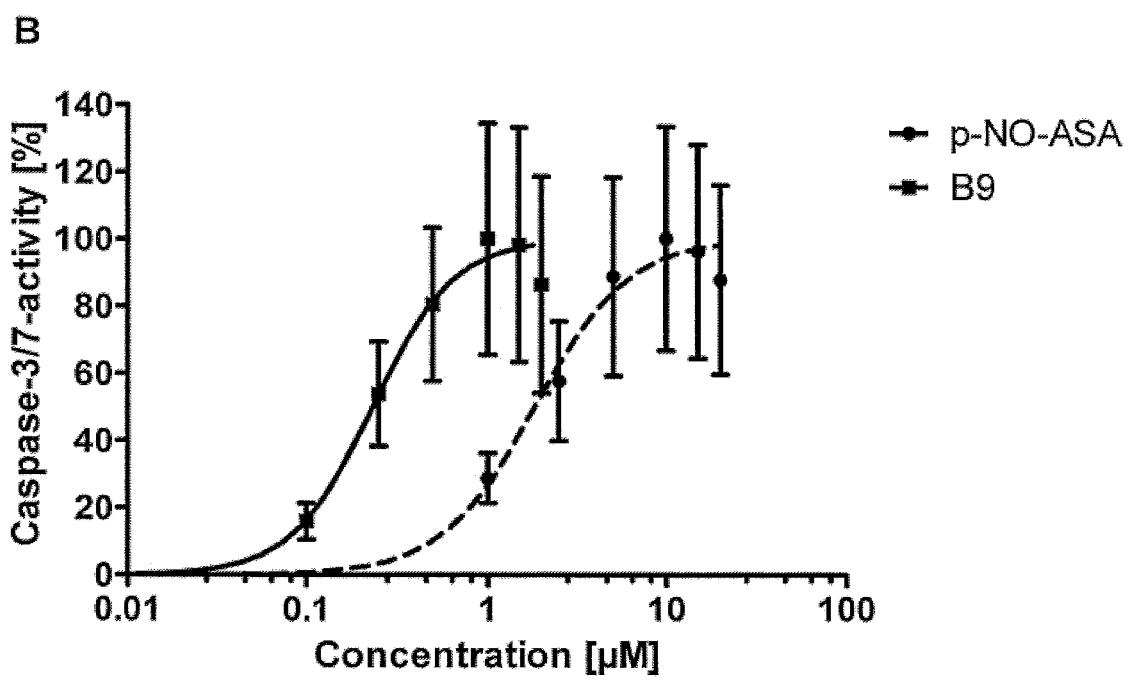

FIG. 8 depicts the involvement of caspase-mediated apoptosis in CLL cells upon treatment with p-NO-ASA, B9, B12 and B13. Representative blots of 3 independent experiments are shown. Untreated and DMSO (1%) treated cells served as control. beta-actin=loading control (FIG. 8A). para-NO-ASA and B9 induced a concentration-dependent increase in caspase-3/7-activation (FIG. 8B).

Figure 9:
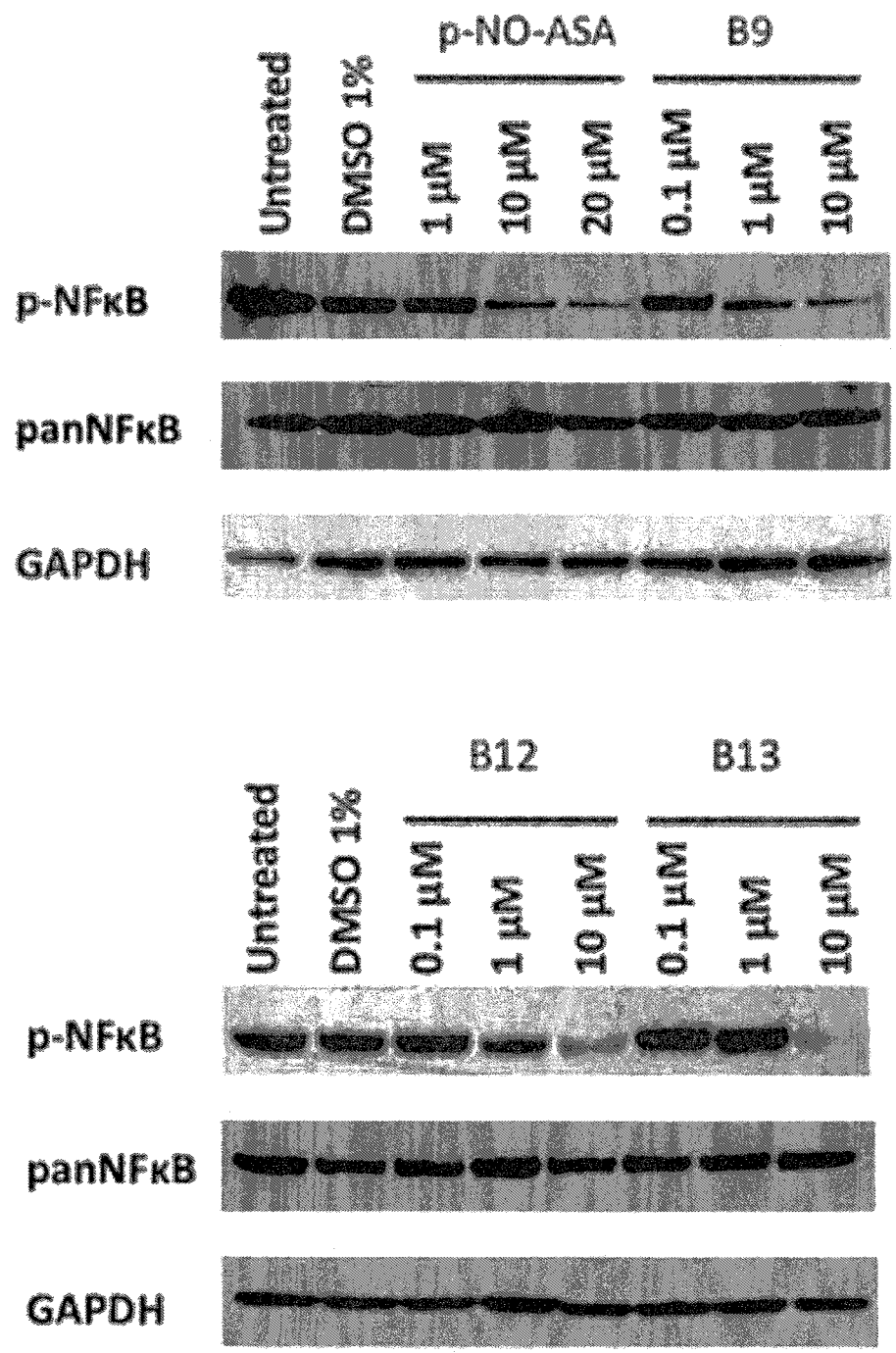

FIG. 9 depicts the concentration dependent reduction of the NFkappaB activity by B1 (p-NO-ASA), B9, B12 and B13 in western blot analyses (see Example 7). CLL cells were treated with B1, B9, B12 and B13 (0.1 µM, 1 µM, 10 µM) for 3 h. Untreated and DMSO (1%) treated cells served as control. GAPDH=loading control.

EXAMPLES

Example 1: Effective Concentrations of Compounds According to the Invention

Primary CLL or peripheral blood mononuclear cells of healthy donors ($5*10^6$/ml) were incubated for 24 h with different compounds according to the invention and NO-ASA as a control. The compounds were added in different concentrations, in particular in concentrations from 0.01-100 µM. Cell survival was assessed by AnnexinV/PI assay (Kit commercially available, e.g. by Biotium Inc, USA; or Phoenix Flow Systems, US), the results were normalized to DMSO control [vehicle] and dose response curves were calculated using a non-linear regression model.

TABLE 1

Effective concentration 50% (EC$_{50}$) of different NO-ASA derivatives.

| | | AnnexinV/PI assay EC$_{50}$ [μM] | | | |
|---|---|---|---|---|---|
| Designation | chemical formula | Primary CLL | n | PBMCs | n |
| B1 pNO—ASA | | 6.7 | 17 | 47.25 | 9 |
| B2 5Me—NO—ASA | | 4.75 | 10 | 48.5 | 5 |
| B3 4Me—NO—ASA | | 4.0 | 10 | 55.09 | 5 |
| B4 2Cl—5CF3—OTBS—BA | | 101.4 | 10 | 1771* | 3 |
| B5 2Cl—5CF3—OH—BA | | 37.2 | 10 | 107.6* | 4 |
| B6 2Cl—5CF3—NO—BA | | 4.42 | 10 | 73.91 | 4 |
| B7 OTBS—BA | | 52.76 | 10 | 203.3* | 4 |
| B7a 5F—NO—ASA | | nt | | nt | |

TABLE 1-continued

Effective concentration 50% (EC$_{50}$) of different NO-ASA derivatives.

| | | AnnexinV/PI assay EC$_{50}$ [μM] | | | |
|---|---|---|---|---|---|
| Designation | chemical formula | Primary CLL | n | PBMCs | n |
| B8 OH—BA | | 57.31 | 10 | / | 4 |
| B9 NO—BA | | 1.85 | 10 | 79.54 | 7 |
| B10 Form-BA | | 79.42 | 10 | 858.9* | 3 |
| B11 NO—OMe—BA | | 14.65 | 10 | 24.4 | 3 |
| B12 Cl—BA | | 1.33 | 10 | 35.02 | 4 |
| B13 NO-Naphthyl | | 1.04 | 10 | 52.7 | 4 |
| B14 NO-cHex | | 3.31 | 8 | 20.19 | 4 |
| B15 NO-AA | | / | 8 | / | 4 |

TABLE 1-continued

Effective concentration 50% ($EC_{50}$) of different NO-ASA derivatives.

| Designation | chemical formula | AnnexinV/PI assay $EC_{50}$ [μM] | | | |
|---|---|---|---|---|---|
| | | Primary CLL | n | PBMCs | n |
| B16 NO-Dansyl | | 82.37 | 8 | 369.8* | 4 |
| B17 NO-Homo-BA | | nt | | nt | |
| B18 NO—2OMeBA | | 25.97 | 6 | / | 4 |
| B19 NO—4OMeBA | | nt | | nt | |
| B20 NO-2Ethin-BA | | 21.84 | 9 | 308* | 2 |
| B21 NO—2N$_3$—BA | | nt | | nt | |
| B22 CO—NO—BA | | nt | | nt | |
| B23 CO—NO-AA | | nt | | nt | |

*= extrapolated, / = not calculable, nt = not tested

Example 2

Due to its favorable characteristics B9 was chosen for in vivo testing in a CLL xenograft mouse model. JVM3 cells (human chronic B cell leukemia cell line) were injected subcuntaneously into the flank of immunincompetent mice. The developing solid tumor was treated with intraperitoneal injections of 8 mg/kg of compound B9 or sesame oil (vehicle) every other day (see FIG. 4).

$1*10^7$ JVM3 cells were injected subcutaneously in SCID beige mice (CB17.Cg-Prkdc$^{scid}$Lyst$^{bg}$-J/Crl). Tumors were measured every other day by caliper and the tumor volume was calculated V=(Length*(0.5*Width$^2$)). Mice carrying a tumor of more than 50 mm$^3$ were treated every other day with either sesame oil (vehicle control) or with 8 mg/kg B9 solved in sesame oil via intraperitoneal injections. The abortion criteria given by the GV-SOLAS for tumor bearing mice were applied. p-values were calculated using unpaired two-tailed Students test.

FIG. 4 shows a significant reduction in tumor growth by B9 treatment. The inhibition of the tumor growth is highly significant after day 11. The Inhibition of the growth rate (IR) was highest at day 17 with 65.33%. Two animals of the control group had to be sacrificed as their tumor exceeded 15 mm in diameter (abortion criteria). Severe side effects were not observed during vehicle or B9 treatment. Mice reacted to the treatment with slightly reduced mobility for 15 to 30 min, while drinking and feeding normally. A reduction of bodyweight was not observed. B9 significantly reduced the tumor growth in a xenograft mouse model (Day 9: B9 treatment=82.97 mm$^3$).

Example 3: The in Vitro Efficacy of the NO-ASA Derivatives in Subgroups of CLL Treatment success in CLL may depend on cytogenetic and molecular parameters as for instance del13q or TP53 gene disruption. Therefore, the NO-ASA derivatives were examined on (chronic) B cell lymphoma cell lines with different geno- and phenotypes (JVM3, EHEB, U2932, MEC-1, GRANTA-519). The cells were treated with concentrations between 0.01 and 1000 µM for 24 h followed by the addition of luminogenic CellTiter-Glo® reagent.

p-NO-ASA was significantly less effective against MEC-1 (EC$_{50}$=53.44 mM, p<0.001) and GRANTA-519 (EC$_{50}$=22.21 mM, p<0.001) compared to B9 (MEC-1: EC$_{50}$=6.62 mM; GRANTA-519: ED$_{50}$=2.28 mM), B12 (MEC-1: EC$_{50}$=3.24 mM; GRANTA-519: EC$_{50}$=0.68 mM) and B13 (MEC-1: EC$_{50}$=24.13 mM; GRANTA-519: EC$_{50}$=19.72 mM). See FIG. 5.

Example 4

Further, the derivatives B9, B12 and B13 were tested in comparison to para-NO-ASA on CLL cells which harbour a TP53 mutation. The patient subgroup with a TP53 disruption is characterized by a considerable dismal prognosis. CLL cells of patients with and without the TP53 mutation were treated with five different concentrations (0.01, 0.1, 1, 10, 100 µM) of para-NO-ASA, B9, B12 and B13 for 24 h.

FIG. 6 demonstrates the results of FACS analyses of said treated cells, showing that all the compounds especially B9 and B12 have a great effect on CLL cells without a TP53 mutation. Additionally, the three compounds B9, B12 and B13 were more effective on TP53-mutated CLL cells in comparison to para-NO-ASA (B1). B9 was the compound of said group, showing the most remarkable effect on CLL cells with and without TP53 mutation.

Example 5

In the following experiment the possible therapeutic window for NO-ASA derivatives was investigated. Therefore, the influence of the most effective derivatives on cell viability and induction of apoptosis on several cancer cell lines was analyzed by Annexin staining. The melanoma cell line MelJuso, the colon carcinoma cell line SW480, the small cell lung cancer cell line HCC44, the ovarian adenocarcinoma cell line COLO704 and the acute myeloid leukemia cell line SH2 were treated with concentrations of p-NO-ASA and B9, B12 and B13 in a range between 0.01 µM and 100 µM for 24 h, followed by addition of luminogenic CellTiter-Glo® reagent. The three derivatives (B9, B12 and B13) showed a clear cytotoxic effect on all cancer cell lines. FIG. 7 shows the results on said cell lines. p-NO-ASA, B9, B12 and B13 reduced ATP content in SW480, MelJuso, HCC44, SH2 and COLO704 cell lines likewise significantly, whereas p-NO-ASA is significantly less effective in SW480.

The results of the survival measured by ATP-Assay further underline that the three derivatives B9, B12 and B13 exhibit therapeutic capacity for different neoplasias and solid tumors. Especially B12 shows toxic effects on cancer cells (SH2 EC$_{50}$:0.005 µM, SW480 EC$_{50}$: 129.5 µM, MelJuso EC$_{50}$: 0.54 µM, HCC44 EC$_{50}$: 1.05 µM, COLO704 EC$_{50}$: 2.77). Also the results of the apoptosis array show induction of apoptosis in different diseases by concentrations between B9 1-9 µM, B12 1-5 µM and B13 7-57 µM (see Table below).

Table accompanying Example 5. Overview of the EC$_{50}$ values of cell survival analyzed by ATP content and Annexin V/PI assay. n.t.; not tested

| Cell line | Viability assay of CLL cells EC$_{50}$ [µM] (n) B9 | Annexin V/PI assay of CLL cells EC$_{50}$ [µM] (n) B9 | Viability assay of CLL cells EC$_{50}$ [µM] (n) B12 | Annexin V/PI assay of CLL cells EC$_{50}$ [µM] (n) B12 | Viability assay of CLL cells EC$_{50}$ [µM] (n) B13 | Annexin V/PI assay of CLL cells EC$_{50}$ [µM] (n) B13 |
|---|---|---|---|---|---|---|
| SW480 | 31.81 | n.t. | 129.50 | n.t. | 189.50 | n.t. |
| SH2 | 0.16 | 1.93 | 0.01 | 1.68 | 0.64 | 6.95 |
| MelJuso | 0.89 | 8.76 | 0.54 | 4.79 | 4.79 | 57.45 |
| HCC44 | 2.48 | 6.76 | 1.03 | 7.35 | 1.68 | 37.86 |
| COLO704 | 4.33 | 7.25 | 2.77 | 1.80 | 7.86 | 53.70 |

Example 6: Involvement of Caspase-Mediated Apoptosis in CLL Cells upon Treatment with p-NO-ASA, B9, B12 and B13

To determine whether the toxicity on CLL cells is due to caspase-mediated apoptosis, the cleavage of PARP (Poly (ADP-ribose)-Polymerase 1) and XIAP (X-linked inhibitor of apoptosis) was analyzed by immunoblot. CLL cells were cultured alone, with 1% DMSO or with $EC_{50}$ of p-NO-ASA, meta-NO-ASA, B9, B12 and B13 for 24 h followed by protein lysation and western blot analysis using antibodies to detect prognostic apoptotic proteins (XIAP, PARP). Agents-treatment at $EC_{50}$ concentration affected PARP cleavage and clearly reduced levels of anti-apoptotic proteins XIAP. All compounds tested induced PARP and XIAP cleavage (FIG. 8A). Further a caspase-3/7 assay was carried out. CLL cells were incubated with para-NO-ASA and B9 in different concentrations ranging from 0.01 µM to 20 µM for 6 h followed by addition of luminogenic caspase-3/7-substrate. This indicates the reduction of the survival of CLL cells upon treatment with p-NO-ASA and B9 due to the induction of caspase-mediated apoptosis. Para-NO-ASA and B9 also showed a concentration dependent activation of caspases 3 and 7 ($EC_{50}$ B9=0.23 µM, 95% CI=0.11 to 0.49 µM; $EC_{50}$ p-NO-ASA=1.84 µM, 95% CI=0.81 to 4.21 µM) in a specific caspase-3/7 assay (FIG. 8B).

Example 7: The Influence of NO-ASA Derivatives on Major CLL Intracellular Signalling Pathways (NFkappaB, WNT)

The BCR signalling pathway plays an important pathogenic role in CLL and lymphomas leading often to a constitutive active NFkappaB (in this state NFkappaB is phosphorylated). Therefore the influence of the derivatives on the phosphorylation status of NFkappaB was analyzed by Western Blot. CLL cells were treated with 0.1 µM, 1 µM or 10 µM of each derivate, respectively, for 3 h. CLL cells were treated with B1, B9, B12 and B13 (0.1 µM, 1 µM, 10 µM) for 3 h. Untreated and DMSO (1%) treated cells served as control. GAPDH=loading control.

The NO-ASA derivatives induced a concentration dependent reduction of phosphorylated NFkappaBp65 protein and therefore a repression of the signalling NFkappaB pathway. B9, B12 and B13 induced the reduction by a concentration of just 10 µM while of p-NO-ASA the twofold concentration was needed for the induction of the reduction of NFkappaB p65 protein (see FIG. 9).

Example 8: Synthesis Procedures

B1: pNO-ASA

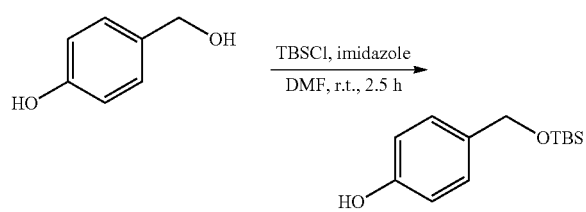

In an inert 100 mL three-necked flask 6.02 g (88.6 mmol, 2.19 eq) imidazole and 6.76 g (44.8 mmol, 1.11 eq) tert-butyl(chloro)dimethylsilane were placed. After evacuating and flooding with argon twice, 40.0 mL dry DMF were added and stirred for 10 minutes at room temperature. Afterwards 5.00 g (40.3 mmol, 1.00 eq) 4-(hydroxymethyl) phenol were added. The stirring was continued for 2.5 hours. The suspension was mixed with 150 mL brine and extracted twice with 100 mL ethyl acetate. The solvent was removed under reduced pressure and the crude product was purified by flash chromatography on silica gel (cyclohexane/ethyl acetate=5:1) to obtain the title compound as a colourless oil in 6.78 g (28.5 mmol, 71%).

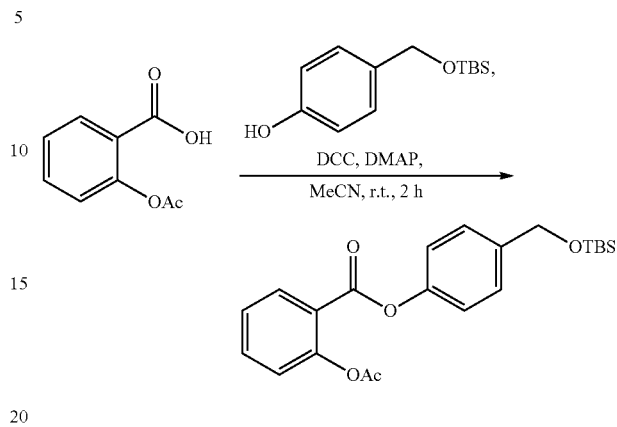

In an inert 100 mL Schlenk flask 2.25 g (12.5 mmol, 1.00 eq) acetyl salicylic acid were dissolved in 45.0 mL acetonitrile. 2.98 g (12.5 mmol, 1.00 eq) 4-(((tert-butyldimethylsilyl)oxy)methyl)phenol, 153 mg (1.25 mmol, 0.10 eq) 4-(dimethylamino)-pyridine and 2.84 g (13.8 mmol, 1.10 eq) dicyclohexylcarbodiimide were added. After 2 hours the solvent was removed under reduced pressure and the crude product was purified by flash chromatography on silica gel (cyclohexane/ethyl acetate=10:1) to obtain the title compound as a colourless solid in 3.14 g (7.85 mmol, 63%).

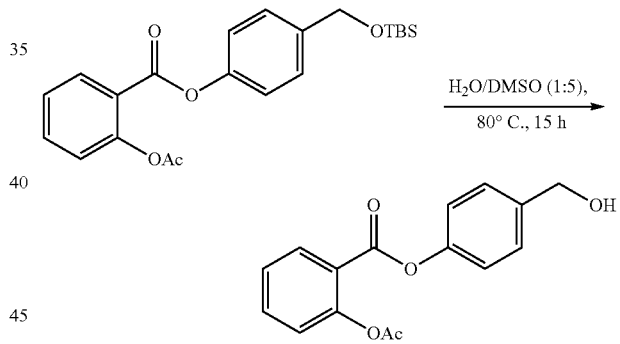

In an inert 250 mL three-necked flask 2.90 g (7.24 mmol, 1.00 eq) 4-(((tert-butyldimethylsilyl)oxy)methyl)phenyl 2-acetoxybenzoate were dissolved in 7.00 mL water and 35.0 mL dimethylsulfoxide. After stirring for 15 h at 80° C. and cooling to room temperature 60.0 mL water were added. The mixture was extracted twice with 60.0 mL diethyl ether. The solvent was removed under reduced pressure and the crude product was purified by flash chromatography on silica gel (cyclohexane/ethyl acetate=1:1) to obtain the title compound as a colourless solid in 1.78 g (6.23 mmol, 86%).

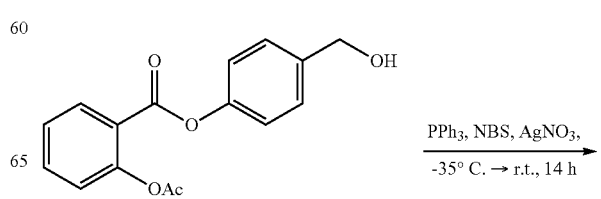

33

-continued

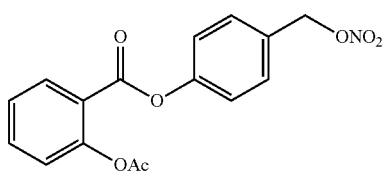

In an inert 25.0 mL Schlenk flask 1.80 g (7.89 mmol, 1.00 eq) 4-(hydroxymethyl)phenyl 2-acetoxybenzoate and 2.07 g (7.89 mmol, 1.00 eq) triphenylphosphine were dissolved in 8.00 mL acetonitrile and 3.20 mL dichloromethane. It was cooled to −45° C. and 1.40 g (7.89 mmol, 1.00 eq) N-bromosuccinimide were added. The cooling was removed, while NBS got dissolved slowly. 5 min later 2.01 g (11.84 mmol, 1.50 eq) silver nitrate were added. After 14 h stirring at room temperature the precipitate was filtered off. The filtrate was removed from the solvent under reduced pressure and the crude product was purified by flash chromatography on silica gel (cyclohexane/ethyl acetate=10:1) to obtain the title compound as a colourless solid in 984 mg (2.97 mmol, 57%).

B2: 5Me-NO-ASA

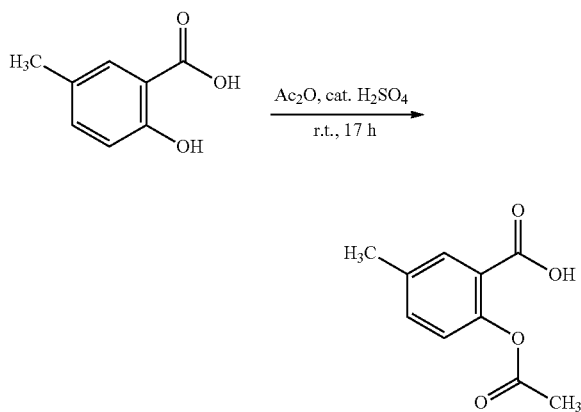

In an inert 100 mL three-necked round bottom flask 5.00 g (32.9 mmol, 1.00 eq) 2-hydroxy-5-methylbenzoic acid and 16.3 g (159 mmol, 16.1 mL, 4.86 eq) acetic acid anhydride were mixed. To this suspension a catalytic amount (6.44 mg (657 µmol, 3.50 µL, 0.02 eq)) of concentrated sulphuric acid was added. After 1 hour 70.0 mL water were added and stirring was continued for additional 17 h. The precipitate was filtered off, washed with 100 mL water. The title compound was obtained as a colourless solid in 6.22 g (32.0 mmol, 98%).

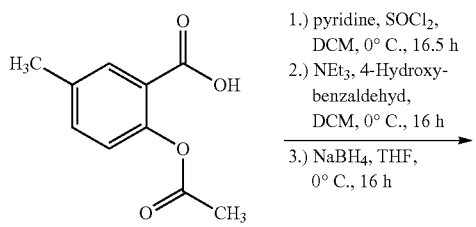

34

-continued

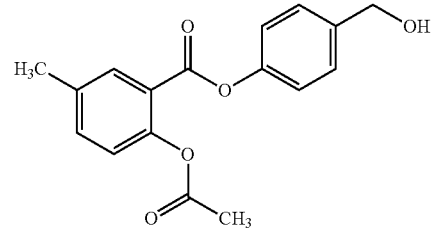

In an inert 250 mL three-necked round bottom flask 5.00 g (25.8 mmol, 1.00 eq) 2-acetoxy-5-methylbenzoic acid were dissolved in 65.0 mL dry DCM. After adding 2.04 g (25.8 mmol, 2.08 mL, 1.00 eq) pyridine the solution was cooled to 0° C. Over a period of 10 minutes 4.60 g (38.7 mmol, 2.81 mL, 1.50 eq) thionylchloride were added. Stirring was continued for additional 16.5 h at 0° C. and the solvent was removed afterwards. The oil was taken up by 50.0 mL dry DCM and 3.14 g (31.0 mmol, 4.29 mL, 1.20 eq) triethylamine were added. At 0° C. 3.78 g (31.0 mmol, 1.20 eq) 4-hydroxybenzaldehyde were added. The solution was stirred for additional 3 h at 0° C. The mixture was washed twice with each 50.0 mL water and 30.0 mL saturated sodium hydrogen carbonate solution. After drying over magnesium sulfate the solvent was removed under reduced pressure. The crude product was purified by flash chromatography on silica gel (cyclohexane/ethyl acetate=2:1) to obtain the intermediate as a colourless solid in 4.16 g (14.0 mmol, 54%). This intermediate was taken up in 45.0 mL dry THF, cooled to 0° C. and 491 mg (12.9 mmol, 0.50 eq) sodium borohydride were added. After stirring for 16 h the solution was washed with 45.0 mL saturated ammonium chloride solution, dried over magnesium sulfate and the solvent was removed under reduced pressure. The crude product was purified by flash chromatography on silica gel (cyclohexane/ethyl acetate=1:1) to obtain the title compound as a colourless solid in 1.91 g (6.37 µmol, 25%).

In an inert 100 mL three-necked round bottom flask 800 mg (2.66 mmol, 1.00 eq) 4-(hydroxymethyl)phenyl 2-acetoxy-5-methylbenzoate were dissolved in 25.0 mL DCM, cooled to −30° C. and over a period of 1 minute 252 mg (3.19 mmol, 283 µL, 1.20 eq) pyridine and 475 mg (3.99 mmol, 283 µL, 1.50 eq) thionylchloride were added. Stirring at −30° C. was continued for additional 45 minutes and then at room temperature for 18 h. The solution was washed with 50.0 mL brine and 25.0 mL water. The organic layer was dried over magnesium sulfate and the solvent was removed under reduced pressure. The crude product was purified by flash chromatography on silica gel (cyclohexane/ethyl acetate=4:1) to obtain the title compound as a colourless solid in 543 mg (1.70 mmol, 64%).

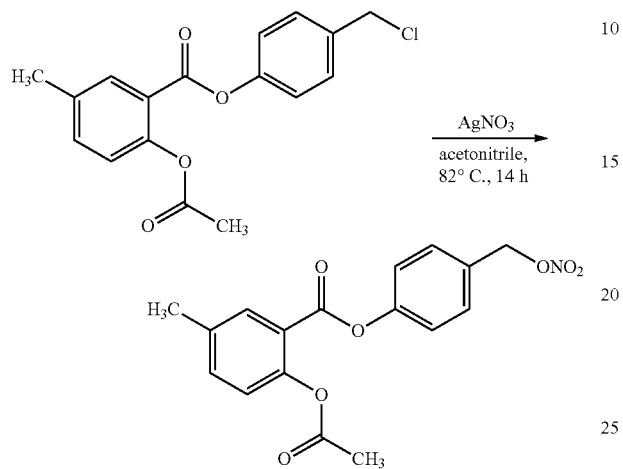

In an inert 50.0 mL three necked round bottom flask 450 mg (1.41 mmol, 1.00 eq) 4-(chloromethyl)phenyl 2-acetoxy-5-methylbenzoate were dissolved in 15.0 mL dry acetonitrile. After the addition of 479 mg (2.82 mmol, 2.00 eq) silver nitrate the solution was heated in the dark to reflux for 14 h. The precipitate was filtered off and the filtrate was dried over magnesium sulfate and the solvent was removed under reduced pressure. The crude product was purified by flash chromatography on silica gel (cyclohexane/ethyl acetate=4:1) to obtain the title compound as a bright yellow solid in 437 mg (1.27 mmol, 90%).

B3: 4Me-NO-ASA

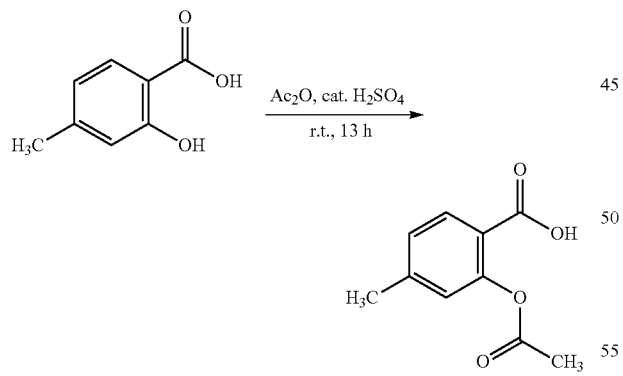

In an inert 250 mL three-necked round bottom flask 6.00 g (39.4 mmol, 1.00 eq) 2-hydroxy-4-methylbenzoic acid and 13.1 g (159 mmol, 12.1 mL, 3.26 eq) acetic acid anhydride were mixed. To this suspension a catalytic amount (69.5 mg (990 µmol, 52.5 µL, 0.03 eq)) of concentrated sulphuric acid was added. After 1 hour 83.7 mL water were added and stirring was continued for additional 13 h. The precipitate was filtered off, washed with 200 mL water. The title compound was obtained as a colourless solid in 6.79 g (34.9 mmol, 89%).

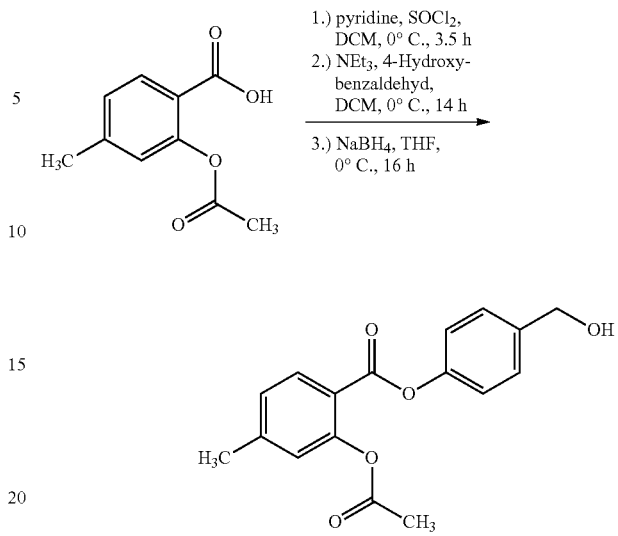

In an inert 250 mL three-necked round bottom flask 5.00 g (25.8 mmol, 1.00 eq) 2-acetoxy-4-methylbenzoic acid were dissolved in 100.0 mL dry DCM. After adding 2.04 g (25.8 mmol, 2.08 mL, 1.00 eq) pyridine the solution was cooled to 0° C. Over a period of 10 minutes 4.60 g (38.7 mmol, 2.81 mL, 1.50 eq) thionylchloride were added. Stirring was continued for additional 3.5 h at 0° C. and the solvent was removed afterwards. The oil was taken up by 75.0 mL dry DCM and 3.14 g (31.0 mmol, 4.29 mL, 1.20 eq) triethylamine were added. At 0° C. 3.78 g (31.0 mmol, 1.20 eq) 4-hydroxybenzaldehyde were added. The solution was stirred for additional 14 h at 0° C. The mixture was washed with 2×75.0 mL water and 2×75.0 mL saturated sodium hydrogen carbonate solution. Afterwards drying over magnesium sulfate and the solvent was removed under reduced pressure. The crude product was purified by flash chromatography on silica gel (cyclohexane/ethyl acetate=2:1) to obtain the intermediate as a colourless solid in 5.18 g (17.4 mmol, 67%). This intermediate was taken up in 50.0 mL dry THF, cooled to 0° C. and 701 mg (18.4 mmol, 0.72 eq) sodium borohydride were added.

After stirring for 16 h the solution was washed with 45.0 mL saturated ammonium chloride solution, dried over magnesium sulfate and the solvent was removed under reduced pressure. The crude product was purified by flash chromatography on silica gel (cyclohexane/ethyl acetate=2:1) to obtain the title compound as a colourless solid in 856 mg (2.85 mmol, 11%).

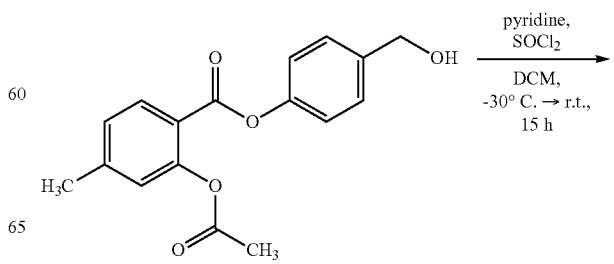

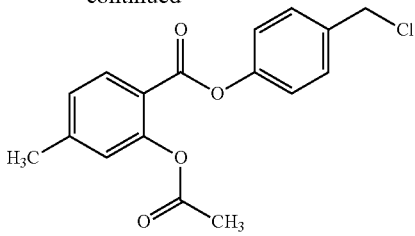

In an inert 50.0 mL three-necked round bottom flask 500 mg (1.67 mmol, 1.00 eq) 4-(hydroxymethyl)phenyl 2-acetoxy-4-methylbenzoate were dissolved in 25.0 mL DCM, cooled to −30° C. and over a period of 2 minutes 158 mg (2.80 mmol, 161 µL, 1.20 eq) pyridine and 297 mg (2.50 mmol, 177 µL, 1.50 eq) thionylchloride were added. Stirring at −30° C. was continued for additional 45 minutes and then at room temperature for 15 h. The solution was washed with 50.0 mL brine and 25.0 mL water. The organic layer was dried over magnesium sulfate and the solvent was removed under reduced pressure. The crude product was purified by flash chromatography on silica gel (cyclohexane/ethyl acetate=10:1) to obtain the title compound as a colourless solid in 315 mg (988 µmol, 59%).

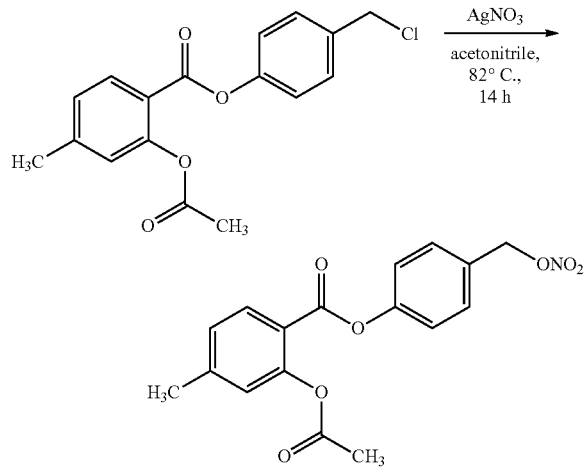

In an inert 25.0 mL three-necked round bottom flask 200 mg (627 µmol, 1.00 eq) 4-(chloromethyl)phenyl 2-acetoxy-4-methylbenzoate were dissolved in 7.00 mL dry acetonitrile. After the addition of 213 mg (1.25 µmol, 2.00 eq) silver nitrate the solution was heated in the dark to reflux for 14 h. The precipitate was filtered off and the filtrate was dried over magnesium sulfate and the solvent was removed under reduced pressure. The crude product was purified by flash chromatography on silica gel (cyclohexane/ethyl acetate=10:1) to obtain the title compound as a solid in 188 mg (544 µmol, 87%).
B4: 2Cl-5CF3-OTBS-BA

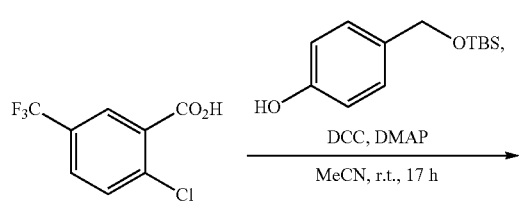

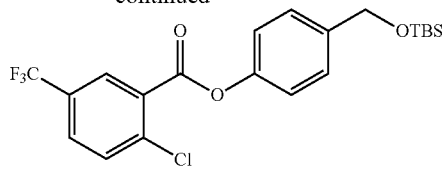

In an inert 25.0 mL Schlenk flask 561 mg (2.50 mmol, 1.00 eq) 2-chloro-5-trifluoromethylbenzoic acid were dissolved in 10.0 mL acetonitrile. 596 mg (2.50 mmol, 1.00 eq) 4-(((tert-Butyldimethylsilyl)oxy)methyl)phenol, 30.5 mg (250 µmol, 0.10 eq) 4-(dimethylamino)-pyridine and 567 mg (2.75 mmol, 1.10 eq) dicyclohexylcarbodiimide were added. After 17 hours the solvent was removed under reduced pressure and the crude product was purified by flash chromatography on silica gel (cyclohexane/ethyl acetate=20:1) to obtain the title compound as a colourless solid in 1.05 g (2.36 mmol, 94%).
B5: 2Cl-5CF3-OH-BA

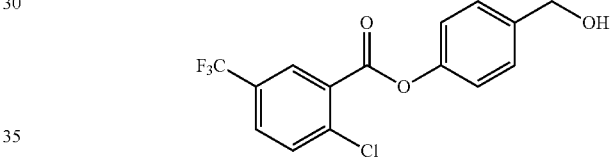

In an inert 50 mL three-necked flask 850 mg (1.91 mmol, 1.00 eq) 4-(((tert-Butyldimethylsilyl)oxy)methyl)phenyl 2-chloro-5-(trifluoromethyl)benzoate were dissolved in 2.00 mL water and 10.0 mL dimethylsulfoxide. After stirring for 19 h at 80° C. and cooling to room temperature 20.0 mL water were added. The mixture was extracted twice with 20.0 mL diethyl ether. The solvent was removed under reduced pressure and the crude product was purified by flash chromatography on silica gel (cyclohexane/ethyl acetate=1:1) to obtain the title compound as a colourless solid in 619 mg (1.87 mmol, 98%).
B6: 2Cl-5CF3-NO-BA

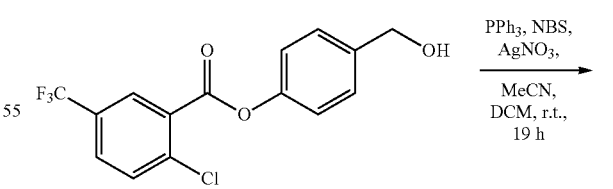

In an inert 10.0 mL Schlenk flask 300 mg (910 µmol, 1.00 eq) 4-(hydroxymethyl)phenyl 2-chloro-5-(trifluoromethyl)

benzoate and 238 mg (910 μmol, 1.00 eq) triphenylphosphine were dissolved in 1.00 mL acetonitrile and 400 μL dichloromethane. It was cooled to −45° C. and 162 mg (910 μmol, 1.00 eq) N-bromosuccinimide were added. The cooling was removed, while NBS got dissolved slowly. 5 min later 155 mg (1.37 mmol, 1.50 eq) silver nitrate were added. After 19 h stirring at room temperature the precipitate was filtered off. The solvent was removed from the filtrate under reduced pressure and the crude product was purified by flash chromatography on silica gel (cyclohexane/ethyl acetate=2:1) to obtain the title compound as a colourless solid in 267 mg (711 μmol, 78%).

B7: OTBS-BA

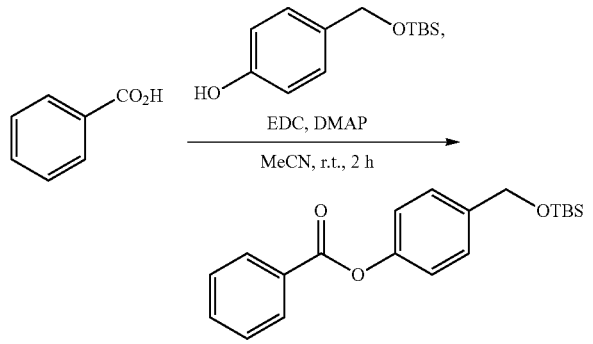

In an inert 15.0 mL Schlenk flask 500 mg (4.09 mmol, 1.00 eq) benzoic acid were dissolved in 10.0 mL acetonitrile. 975 mg (4.09 mmol, 1.00 eq) 4-(((tert-butyldimethylsilyl)oxy)methyl)phenol, 49.9 mg (409 μmol, 0.10 eq) 4-(dimethylamino)-pyridine and 862 mg (4.50 mmol, 1.10 eq) EDC were added. After 2 hours the solvent was removed under reduced pressure and the crude product was purified by flash chromatography on silica gel (cyclohexane/ethyl acetate=10:1) to obtain the title compound as a colourless solid in 1.37 g (3.90 mmol, 95%).

B7a: 5F-NO-ASA

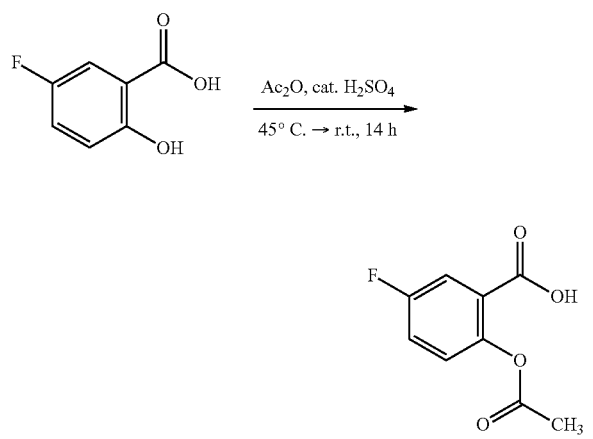

In a 250 mL round bottom flask 5.00 g (32.0 mmol, 1.00 eq) 5-fluoro-2-hydroxybenzoic acid and 6.55 g (64.0 mmol, 6.05 mL, 2.00 eq) acetic acid anhydride were mixed. To this suspension a catalytic amount (6 drops) of concentrated sulphuric acid was added at 35° C. whereupon the temperature of the mixture rose to 45° C. After 14 hours, 67.0 mL water were added. The precipitate was filtered off, washed with 250 mL water. The title compound was obtained as a colourless solid in 5.49 g (27.7 mmol, 86%).

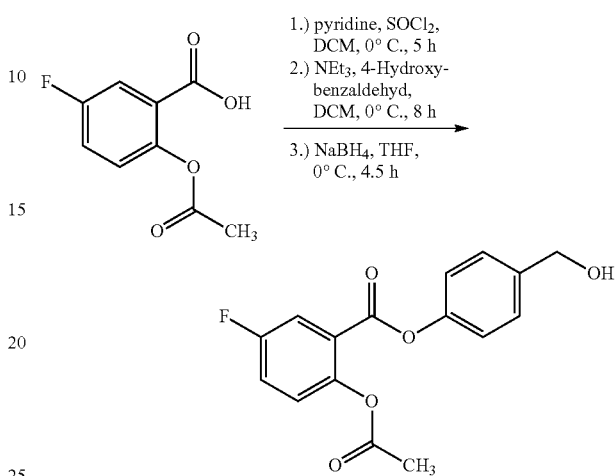

In an inert 25.0 mL three-necked round bottom flask 872 mg (4.40 mmol, 1.00 eq) 2-acetoxy-5-fluorobenzoic acid were dissolved in 11.2 mL dry DCM. After adding 872 mg (4.40 mmol, 1.00 eq) pyridine the solution was cooled to 0° C. Over a period of 15 minutes 872 mg (4.40 mmol, 1.00 eq) thionylchloride were added. Stirring was continued for additional 5 h at 0° C. and the solvent was removed afterwards. The oil was taken up with 8.44 mL dry DCM and 534 mg (5.28 mmol, 732 μL, 1.20 eq) triethylamine were added. At 0° C. 537 mg (4.40 mmol, 1.00 eq) 4-hydroxybenzaldehyde were added. The solution was stirred for additional 8 h at 0° C. The mixture was washed twice with 2×57.00 mL water and 2×7.00 mL saturated sodium hydrogen carbonate solution. After drying over magnesium sulfate, the solvent was removed under reduced pressure. The crude product was purified by flash chromatography on silica gel (cyclohexane/ethyl acetate=2:1) to obtain the intermediate as a colourless solid 700 mg (2.32 mmol, 53%). This intermediate was taken up in 8.00 mL dry THF, cooled to 0° C. and 88.6 mg (2.33 mmol, 0.53 eq) sodium borohydride were added.

After stirring for 4.5 h the solution was washed with 8.00 mL saturated solution of ammonium chloride, dried over magnesium sulfate and the solvent was removed under reduced pressure. The crude product was purified by flash chromatography on silica gel (cyclohexane/ethyl acetate=1:1) to obtain the title compound as a colourless solid in 273 mg (897 μmol, 21%).

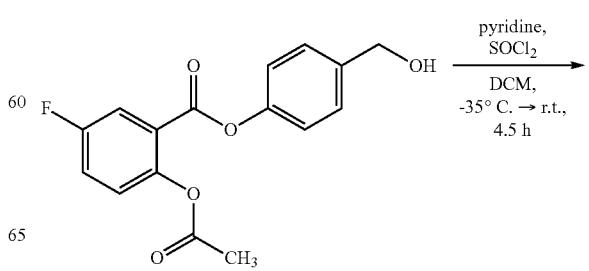

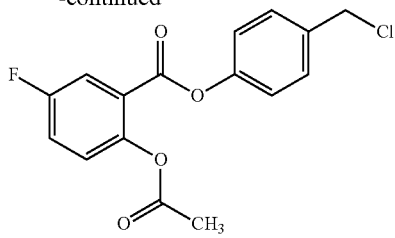

In an inert 25.0 mL three-necked round bottom flask 350 mg (1.15 mmol, 1.00 eq) 4-(hydroxymethyl)phenyl 2-acetoxy-5-fluorobenzoate were dissolved in 11.0 mL DCM, cooled to −30° C. over a period of 5 minutes, then 108 mg (1.37 mmol, 111 µL, 1.19 eq) pyridine and 203 mg (1.68 mmol, 121 µL, 1.49 eq) thionylchloride were added. Stirring at −30° C. was continued for additional 45 minutes and then at room temperature for 4.5 h. The solution was washed with 23.0 mL brine and 11.0 mL water. The organic layer was dried over magnesium sulfate and the solvent was removed under reduced pressure. The crude product was purified by flash chromatography on silica gel (cyclohexane/ethyl acetate=1:1) to obtain the title compound as a colourless solid in 156 mg (480 µmol, 42%).

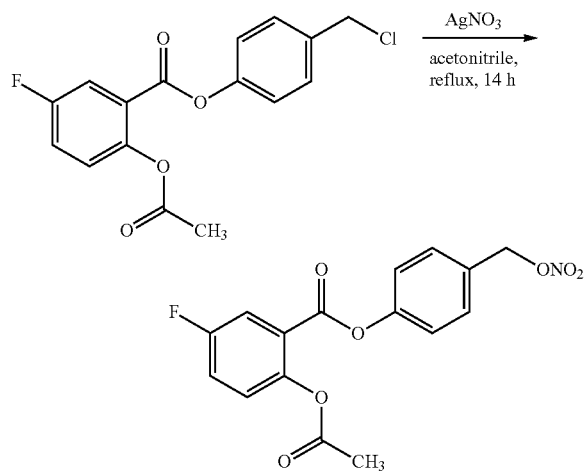

In an inert 10.0 mL three necked round bottom flask 85.0 mg (263 µmol, 1.00 eq) 4-(chloromethyl)phenyl 2-acetoxy-5-fluorobenzoate were dissolved in 3.00 mL dry acetonitrile. After the addition of 88.3 mg (526 µmol, 2.00 eq) silver nitrate, the solution was heated in the dark to reflux for 14 h. The precipitate was filtered off, the filtrate was dried over magnesium sulfate, and the solvent was removed under reduced pressure. The crude product was purified by flash chromatography on silica gel (cyclohexane/ethyl acetate=4:1) to obtain the title compound as a bright yellow solid in 81.0 mg (232 µmol, 89%).

B8: OH-BA

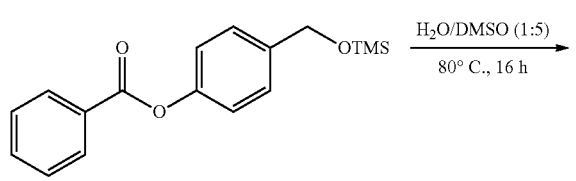

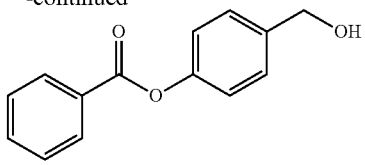

In an inert 50 mL three-necked flask 1.03 g (3.00 mmol, 1.00 eq) 4-(((tert-butyldimethylsilyl)oxy)methyl)phenyl benzoate were dissolved in 3.00 mL water and 15.0 mL dimethylsulfoxide. After stirring for 16 h at 80° C. and cooling to room temperature 20.0 mL water were added. The mixture was extracted twice with 40.0 mL diethyl ether. The solvent was removed under reduced pressure and the crude product was purified by flash chromatography on silica gel (cyclohexane/ethyl acetate=1:1) to obtain the title compound as a colourless solid in 682 mg (2.99 mmol, 100%).

B9: NO-BA

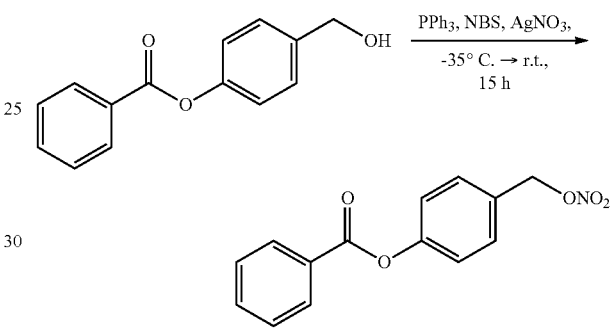

In an inert 10.0 mL Schlenk flask 342 mg (1.50 mmol, 1.00 eq) 4-(hydroxymethyl)phenyl benzoate and 393 mg (1.50 mmol, 1.00 eq) triphenylphosphine were dissolved in 1.50 mL acetonitrile and 600 µL dichloromethane. The solution was cooled to −45° C. and 267 mg (1.50 mmol, 1.00 eq) N-bromosuccinimide were added. The cooling was removed, while NBS got dissolved slowly. 5 min later 382 mg (2.25 mmol, 1.50 eq) silver nitrate were added. After 15 h stirring at room temperature the precipitate was filtered off. The filtrate was removed from the solvent under reduced pressure and the crude product was purified by flash chromatography on silica gel (cyclohexane/ethyl acetate=10:1) to obtain the title compound as a colourless solid in 355 mg (1.30 mmol, 87%).

B10: Form-BA

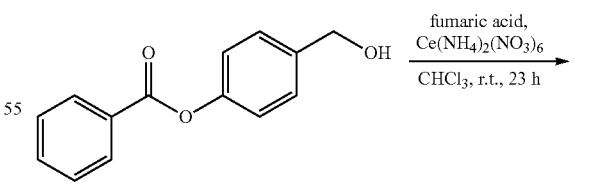

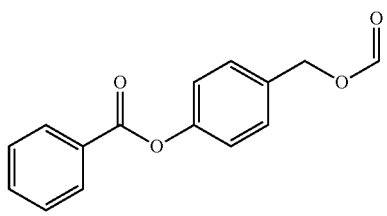

In a 10.0 mL round bottom flask 114 mg (500 µmol, 1.00 eq) 4-(hydroxymethyl)phenyl benzoate, 22.9 mg (500 µmol, 18.8 µL, 1.00 eq) fumaric acid and 27.4 mg (50.0 µmol, 0.10 eq) ceric ammonium nitrate were dissolved in 2.00 mL chloroform. The solution was stirred at room temperature for 23 h. Afterwards 10.0 mL cold water were added and the solution was extracted twice with 10.0 mL MTBE. The crude product was purified by flash chromatography on silica gel (cyclohexane/ethyl acetate=10:1) to obtain the title compound as a colourless solid in 113 mg (441 µmol, 88%).

B11: NO-OMe-BA

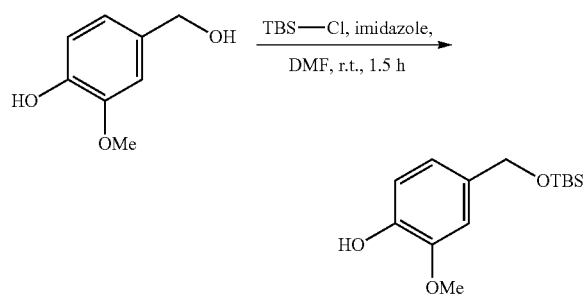

In an inert 25.0 mL three-necked flask 899 mg (13.2 mmol, 2.20 eq) imidazole and 995 mg (6.60 mmol, 1.10 eq) tert-butyl(chloro)dimethylsilane were provided. After evacuating and flooding with Argon twice, 7.00 mL dry DMF were added and stirred for 10 minutes at room temperature. Afterwards 925 mg (6.00 mmol, 1.00 eq) 4-(hydroxymethyl)-2-methoxyphenol were added. The stirring was continued for 1.5 h. The suspension was mixed with 20.0 mL brine and extracted twice with 20.0 mL ethyl acetate. The solvent was removed under reduced pressure and the crude product was purified by flash chromatography on silica gel (cyclohexane/ethyl acetate=10:1) to obtain the title compound as a colourless oil in 1.40 g (5.23 mmol, 87%).

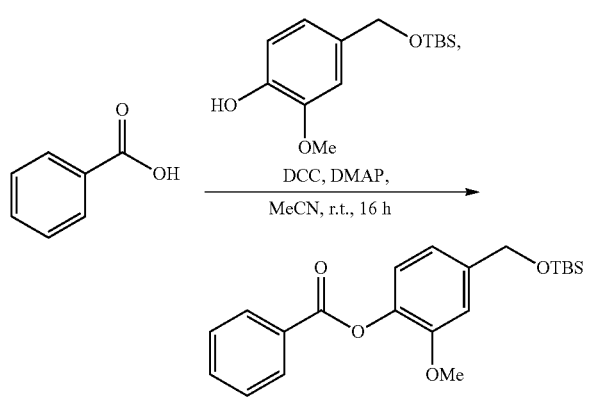

In an inert 25.0 mL Schlenk flask 183 mg (1.50 mmol, 1.00 eq) benzoic acid were dissolved in 7.0 mL acetonitrile. 403 mg (1.50 mmol, 1.00 eq) 4-((tert-butyldimethylsilyloxymethyl)-2-methoxy)-phenol, 18.0 mg (150 µmol, 0.10 eq) 4-(dimethylamino)-pyridine 340 mg (1.65 mmol, 1.10 eq) dicyclohexylcarbodiimide were added. After 16 hours the solvent was removed under reduced pressure and the crude product was purified by flash chromatography on silica gel (cyclohexane/ethyl acetate=10:1) to obtain the title compound as a colourless solid in 543 mg (1.46 mmol, 97%).

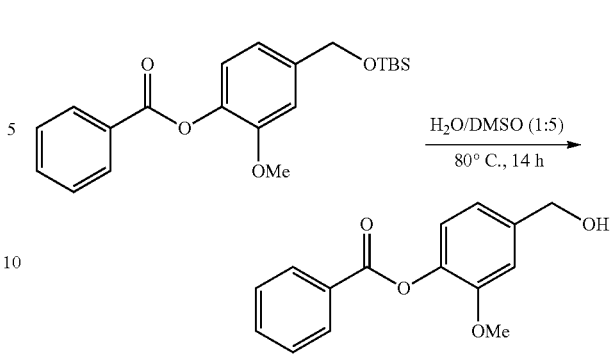

In an inert 25.0 mL Schlenk flask 500 mg (1.34 mmol, 1.00 eq) 4-(((tert-butyldimethylsilyl)oxy)methyl)-2-methoxyphenyl benzoate were dissolved in 1.50 mL water and 7.50 mL dimethylsulfoxide. After stirring for 14 h at 80° C. and cooling to room temperature 10.0 mL water were added. The mixture was extracted twice with 10.0 mL diethyl ether. The solvent was removed under reduced pressure and the crude product was purified by flash chromatography on silica gel (cyclohexane/ethyl acetate=1:1) to obtain the title compound as a colourless solid in 344 mg (1.33 mmol, 99%).

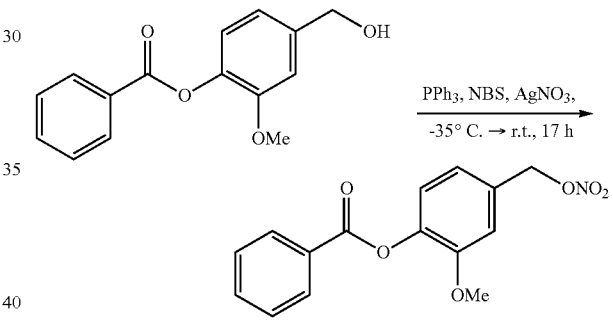

In an inert 10.0 mL Schlenk flask 280 mg (1.08 mmol, 1.00 eq) 4-(hydroxymethyl)-2-methoxyphenyl benzoate and 284 mg (1.08 mmol, 1.00 eq) triphenylphosphine were dissolved in 1.08 mL acetonitrile and 430 µL dichloromethane. The solution was cooled to −45° C. and 193 mg (1.08 mmol, 1.00 eq) N-bromosuccinimide were added. The cooling was removed, while NBS got dissolved slowly. 5 min later 280 mg (1.63 mmol, 1.50 eq) silver nitrate were added. After 17 h stirring at room temperature the precipitate was filtered off. The solvent was removed from the filtrate under reduced pressure and the crude product was purified by flash chromatography on silica gel (cyclohexane/ethyl acetate=5:1) to obtain the title compound as a colourless solid in 322 mg (1.06 mmol, 98%).

B12: Cl-BA

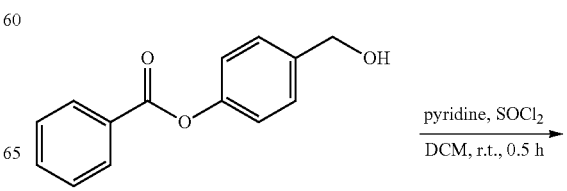

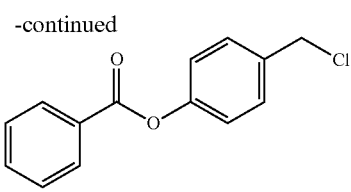

In an inert 50.0 mL Schlenk flask 3.00 g (13.1 mmol, 1.00 eq) 4-hydroxymethylphenyl) benzoate were dissolved in 10.0 mL DCM, and cooled to −30° C. Over a period of 10 minutes 321 mg (3.94 mmol, 318 µL, 1.19 eq) pyridine and 2.35 g (3.94 mmol, 1.43 mL, 1.49 eq) thionylchloride were added. After stirring at room temperature for 0.5 h, 20.0 mL DCM and 20.0 mL water were added to the solution which was then washed with 20.0 mL saturated sodiumcarbonate solution and 20.0 mL water. The organic layer was dried over magnesium sulfate and the solvent was removed under reduced pressure. The crude product was purified by flash chromatography on silica gel (cyclohexane/ethyl acetate=5:1) to obtain the title compound as a colourless solid in 2.93 g (11.9 mmol, 90%).

B13: NO-Naphthyl

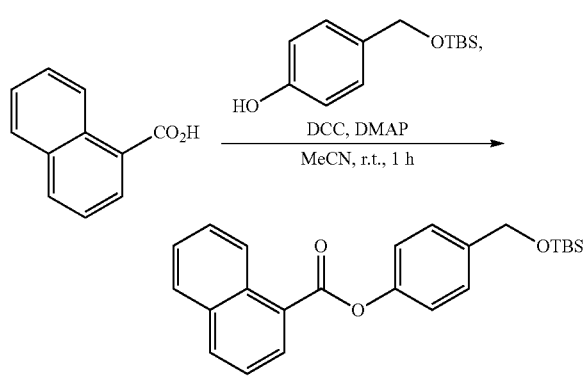

In an inert 100 mL Schlenk flask 1.03 g (6.00 mmol, 1.00 eq) 1-naphthoic acid were dissolved in 25.0 mL acetonitrile. 1.43 g (6.00 mmol, 1.00 eq) 4-(((tert-butyldimethylsilyl)oxy)methyl)phenol, 73.0 mg (600 µmol, 0.10 eq) 4-(dimethylamino)-pyridine and 1.36 g (6.60 mmol, 1.10 eq) dicyclohexylcarbodiimide were added. After 1 hour the solvent was removed under reduced pressure and the crude product was purified by flash chromatography on silica gel (cyclohexane/ethyl acetate=10:1) to obtain the title compound as a colourless solid in 2.31 g (5.60 mmol, 98%).

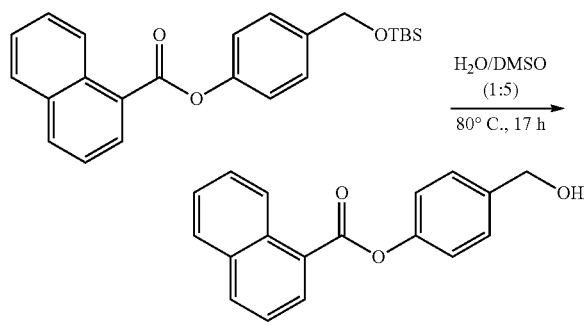

In an inert 100 mL Schlenk flask 1.65 g (4.20 mmol, 1.00 eq) 4-(((tert-butyldimethylsilyl)oxy)methyl)phenyl naphthoate were dissolved in 6.50 mL water and 32.5 mL dimethylsulfoxide. After stirring for 17 h at 80° C. and cooling to room temperature 50.0 mL water were added. The mixture was extracted twice with 50.0 mL diethyl ether. The solvent was removed under reduced pressure and the crude product was purified by flash chromatography on silica gel (cyclohexane/ethyl acetate=2:1) to obtain the title compound as a colourless solid in 1.13 g (4.05 mmol, 96%).

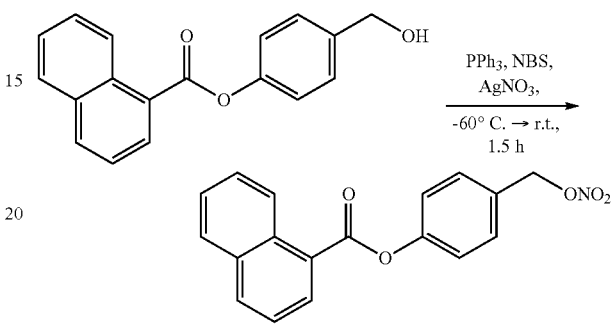

In an inert 25.0 mL Schlenk flask 900 mg (3.23 mmol, 1.00 eq) 4-(hydroxymethyl)phenyl 1-naphthoate and 847 mg (3.23 mmol, 1.00 eq) triphenylphosphine were dissolved in 3.50 mL acetonitrile and 1.40 mL dichloromethane. The solution was cooled to −60° C. and 575 mg (3.23 mmol, 1.00 eq) N-bromosuccinimide were added. The cooling was removed, while NBS got dissolved slowly. 15 min later 823 mg (4.85 mmol, 1.50 eq) silver nitrate were added. After 1.5 h stirring at room temperature the precipitate was filtered off. The solvent was removed from the filtrate under reduced pressure and the crude product was purified by flash chromatography on silica gel (cyclohexane/ethyl acetate=5:1) to obtain the title compound as a colourless solid in 987 mg (3.05 mmol, 94%).

B14: NO-cHex

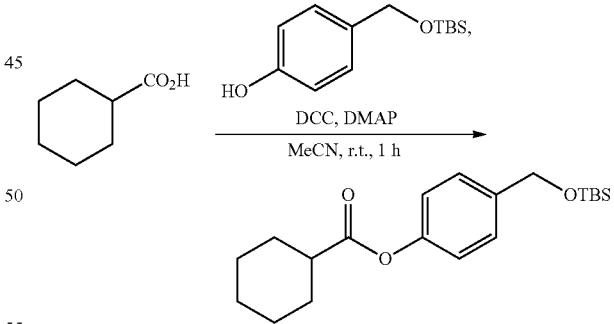

In an inert 25.0 mL Schlenk flask 269 mg (2.10 mmol, 1.00 eq) cyclohexane carboxylic acid were dissolved in 10.0 mL acetonitrile. 500 mg (2.10 mmol, 1.00 eq) 4-(((tert-butyldimethylsilyl)oxy)methyl)phenol, 26.0 mg (210 µmol, 0.10 eq) 4-(dimethylamino)-pyridine and 476 mg (2.31 mmol, 1.10 eq) dicyclohexylcarbodiimide were added. After 1 hour the solvent was removed under reduced pressure and the crude product was purified by flash chromatography on silica gel (cyclohexane/ethyl acetate=10:1) to obtain the title compound as a colourless solid in 723 mg (2.07 mmol, 99%).

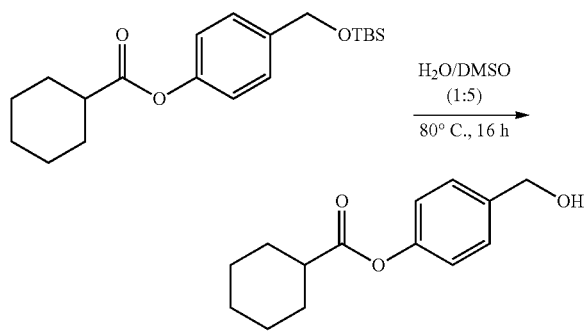

In an inert 25.0 mL Schlenk flask 500 mg (1.44 mmol, 1.00 eq) 4-(((tert-butyldimethylsilyl)oxy)methyl)phenyl cyclohexane carboxylate were dissolved in 1.50 mL water and 7.05 mL dimethylsulfoxide. After stirring for 16 h at 80° C. and cooling to room temperature 10.0 mL water were added. The mixture was extracted twice with 10.0 mL diethyl ether. The solvent was removed under reduced pressure and the crude product was purified by flash chromatography on silica gel (cyclohexane/ethyl acetate=1:1) to obtain the title compound as a colourless solid in 308 mg (1.32 mmol, 92%).

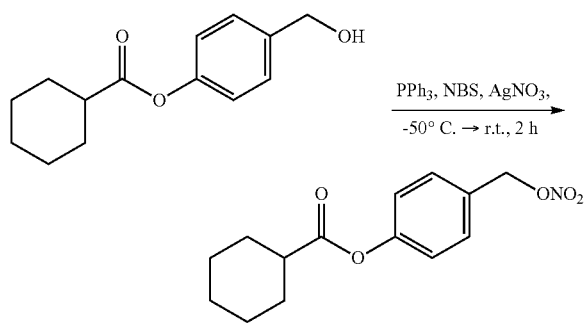

4-(Hydroxymethyl)phenyl cyclohexane carboxylate and 224 mg (854 µmol, 1.00 eq) triphenylphosphine were dissolved in 2.50 mL acetonitrile and 1.00 mL dichloromethane. The solution was cooled to −50° C. and 152 mg (854 µmol, 1.00 eq) N-bromosuccinimide were added. The cooling was removed, while NBS got dissolved slowly. 5 min later 218 mg (1.28 mmol, 1.50 eq) silver nitrate were added. After 2 h stirring at room temperature the precipitate was filtered off. The solvent was removed from the filtrate under reduced pressure and the crude product was purified by flash chromatography on silica gel (cyclohexane/ethyl acetate=10:1) to obtain the title compound as a colourless solid in 216 mg (773 µmol, 91%).

B15: NO-AA

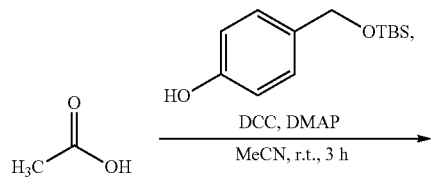

In an inert 25.0 mL Schlenk flask 120 µL (2.10 mmol, 1.00 eq) acetic acid were dissolved in 10.0 mL acetonitrile. 500 mg (2.10 mmol, 1.00 eq) 4-(((tert-butyldimethylsilyl)oxy)methyl)phenol, 26.0 mg (210 µmol, 0.10 eq) 4-(dimethylamino)-pyridine and 476 mg (2.31 mmol, 1.10 eq) dicyclohexylcarbodiimide were added. After 3 hours the solvent was removed under reduced pressure and the crude product was purified by flash chromatography on silica gel (cyclohexane/ethyl acetate=10:1) to obtain the title compound as a colourless solid in 531 mg (1.89 mmol, 90%).

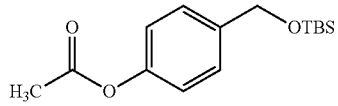
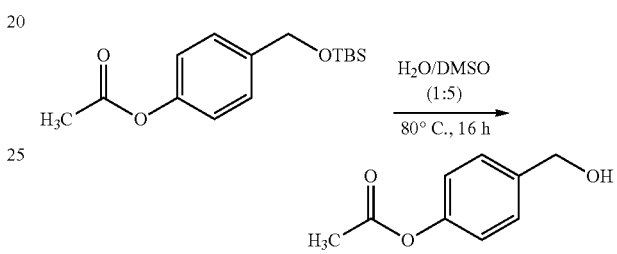

In an inert 25.0 mL Schlenk flask 400 mg (1.43 mmol, 1.00 eq) 4-(((tert-butyldimethylsilyl)oxy)methyl)phenyl acetate were dissolved in 1.50 mL water and 7.05 mL dimethylsulfoxide. After stirring for 16 h at 80° C. and cooling to room temperature 10.0 mL water were added. The mixture was extracted twice with 10.0 mL diethyl ether. The solvent was removed under reduced pressure and the crude product was purified by flash chromatography on silica gel (cyclohexane/ethyl acetate=1:1) to obtain the title compound as a colourless solid in 222 mg (1.34 mmol, 94%).

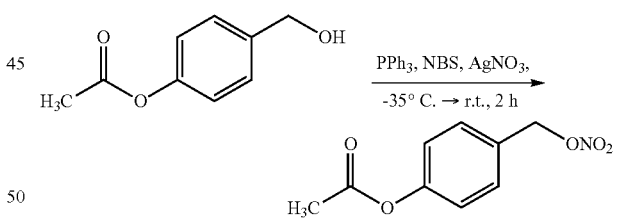

In an inert 25.0 mL Schlenk flask 100 mg (602 µmol, 1.00 eq) 4-(hydroxymethyl)phenyl acetate and 158 mg (602 µmol, 1.00 eq) triphenylphosphine were dissolved in 2.50 mL acetonitrile and 1.00 mL dichloromethane. The solution was cooled to −35° C. and 152 mg (854 µmol, 1.00 eq) N-bromosuccinimide were added. The cooling was removed, while NBS got dissolved slowly. 5 min later 218 mg (1.28 mmol, 1.50 eq) silver nitrate were added. After 2 h stirring at room temperature the precipitate was filtered off. The solvent was removed from the filtrate under reduced pressure and the crude product was purified by flash chromatography on silica gel (cyclohexane/ethyl acetate=5:1) to obtain the title compound as a colourless solid in 105 mg (497 µmol, 83%).

B16: NO-Dansyl

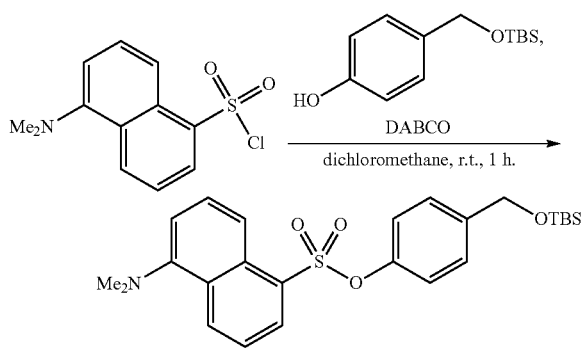

In an inert 10.0 mL Schlenk flask 150 mg (556 μmol, 1.00 eq) dansyl chloride and 133 mg (556 μmol, 1.00 eq) 4-(((tert-butyldimethylsilyl)oxy)methyl)phenol were dissolved in 2.00 mL dichloromethane. To this solution 75.0 mg (667 μmol, 1.20 eq) DABCO were added. After 1 h stirring at room temperature, the solvent was removed under reduced pressure and the crude product was purified by flash chromatography on silica gel (cyclohexane/ethyl acetate=10:1) to obtain the title compound as an oil in 239 mg (507 μmol, 91%).

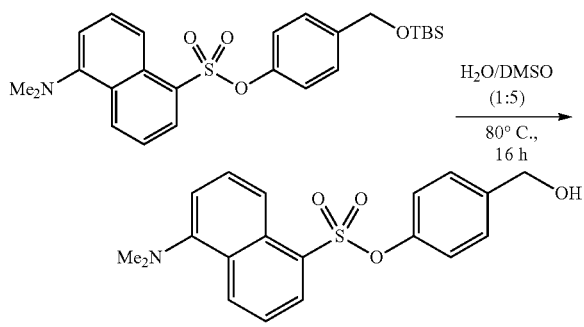

In an inert 10.0 mL Schlenk flask 200 mg (424 μmol, 1.00 eq) 4-(((tert-butyldimethylsilyl)oxy)methyl)phenyl 5-(dimethylamino)naphthalene-1-sulfonate were dissolved in 500 μL water and 2.05 mL dimethylsulfoxide. After stirring for 14 h at 80° C. and cooling to room temperature 5.00 mL water were added. The mixture was extracted twice with 5.00 mL diethyl ether. The solvent was removed under reduced pressure and the crude product was purified by flash chromatography on silica gel (cyclohexane/ethyl acetate=1:1) to obtain the title compound as a colourless solid in 135 mg (378 μmol, 89%).

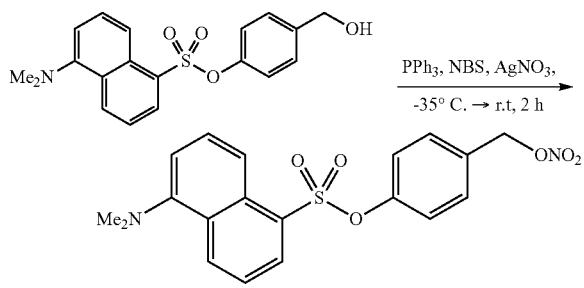

In an inert 10.0 mL Schlenk flask 100 mg (280 μmol, 1.00 eq) 4-(hydroxymethyl)phenyl 5-(dimethylamino)naphthalene-1-sulfonate and 73.0 mg (280 μmol, 1.00 eq) triphenylphosphine were dissolved in 1.00 mL acetonitrile and 400 μL dichloromethane. It was cooled to −35° C. and 50.0 mg (280 μmol, 1.00 eq) N-bromosuccinimide were added. The cooling was removed, while NBS got dissolved slowly. 5 min later 71.0 mg (420 μmol, 1.50 eq) silver nitrate were added. After 2 h stirring at room temperature the precipitate was filtered off. The solvent was removed from the filtrate under reduced pressure and the crude product was purified by flash chromatography (cyclohexane/ethyl acetate=5:1) to obtain the title compound as a yellow oil in 88.0 mg (219 μmol, 78%).

B17: NO-Homo-BA

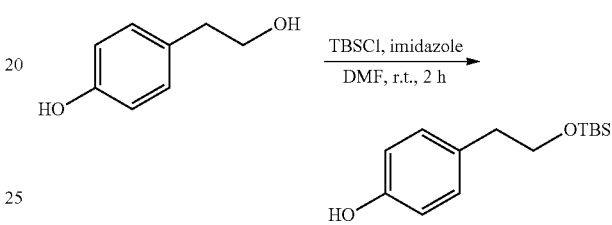

In an inert 50.0 mL Schlenk flask 2.16 g (31.7 mmol, 2.19 eq) imidazole and 2.42 g (16.1 mmol, 1.11 eq) tert-butyl (chloro)dimethylsilane were placed. After evacuating and flooding with argon twice, 15.0 mL (14.3 g, 195 mmol, 13.5 eq) dry DMF were added and stirred for 5 minutes at room temperature. Afterwards 2.00 g (14.5 mmol, 1.00 eq) 4-(2-hydroxyethyl)phenol were added. The stirring was continued for 2 h. The suspension was mixed with 70.0 mL brine and extracted twice with 50.0 mL ethyl acetate. The solvent was removed under reduced pressure and the crude product was purified by flash chromatography on silica gel (cyclohexane/ethyl acetate=5:1) to obtain the title compound as a colourless solid in 2.87 g (14.5 mmol, 79%).

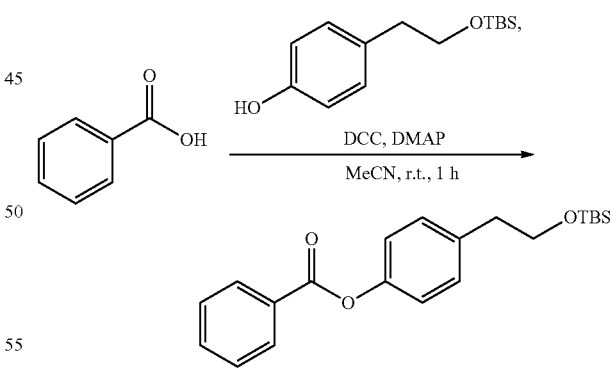

In an inert 50.0 mL Schlenk flask 512 mg (4.19 mmol, 1.00 eq) benzoic acid were dissolved in 20.0 mL acetonitrile. 1.06 g (4.19 mmol, 1.00 eq) 4-(2-((tert-butyldimethylsilyl)oxy)ethyl)phenol, 51.0 mg (419 μmol, 0.10 eq) 4-(dimethylamino)-pyridine and 952 mg (4.61 mmol, 1.10 eq) dicyclohexylcarbodiimide were added. After 1 hour, the solvent was removed under reduced pressure and the crude product was purified by flash chromatography on silica gel (cyclohexane/ethyl acetate=10:1) to obtain the title compound as a colourless solid in 1.45 g (4.11 mmol, 98%).

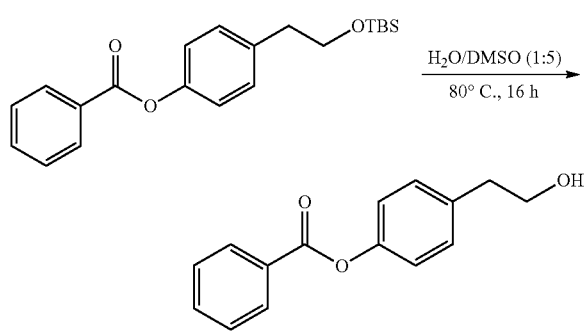

In an inert 50 mL Schlenk flask 1.00 g (2.80 mmol, 1.00 eq) 4-(2-((tert-butyldimethylsilyl)oxy)ethyl)phenyl benzoate was dissolved in 3.00 mL water and 15.0 mL dimethylsulfoxide. After stirring for 16 h at 80° C. and cooling to room temperature 20.0 mL water were added. The mixture was extracted twice with 20.0 mL diethyl ether. The solvent was removed under reduced pressure and the crude product was purified by flash chromatography on silica gel (cyclohexane/ethyl acetate=2:1) to obtain the title compound as a colourless solid in 657 mg (2.71 mmol, 97%).

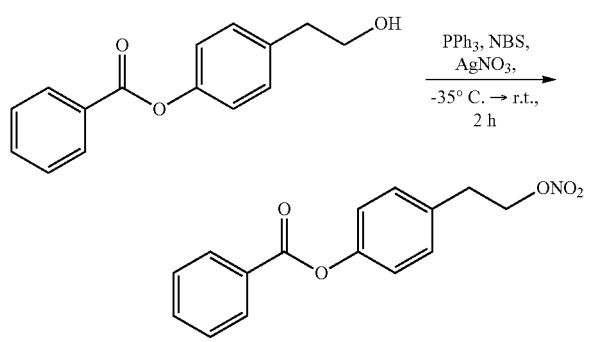

In an inert 25.0 mL Schlenk flask 450 mg (1.86 mmol, 1.00 eq) 4-(2-hydroxyethyl)phenyl benzoate and 487 mg (1.86 mmol, 1.00 eq) triphenylphosphine were dissolved in 5.00 mL acetonitrile and 2.00 mL dichloromethane. The solution was cooled to −35° C. and 331 mg (1.86 μmol, 1.00 eq) N-bromosuccinimide were added. The cooling was removed, while NBS got dissolved slowly. 5 min later 473 mg (2.79 mmol, 1.50 eq) silver nitrate were added. After 2 h stirring at room temperature the precipitate was filtered off. The filtrate was removed from the solvent under reduced pressure and the crude product was purified by flash chromatography on silica gel (cyclohexane/ethyl acetate=5:1) to obtain the title compound as a colourless solid in 446 mg (1.55 mmol, 84%).

B18: NO-2OMeBA

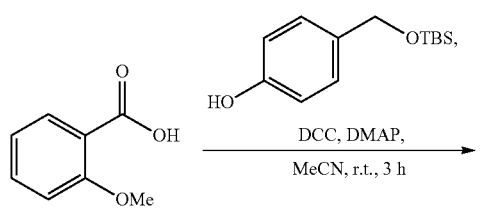

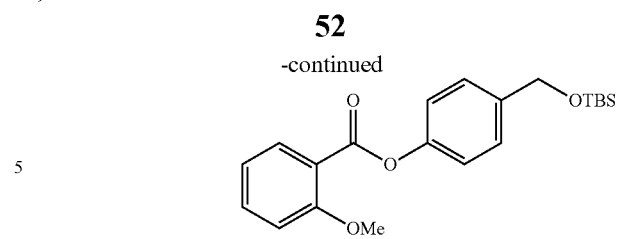

In an inert 250 mL Schlenk flask 3.00 g (19.7 mmol, 1.00 eq) 2-methoxy-benzoic acid were dissolved in 60.0 mL acetonitrile. 4.70 g (19.7 mmol, 1.00 eq) 4-(((tert-butyldimethylsilyl)oxy)methyl)phenol, 241 mg (1.97 mmol, 0.1 eq) 4-(dimethylamino)-pyridine and 4.48 g (21.7 mmol, 1.1 eq) dicyclohexylcarbodiimide were added. After 3 hours the solvent was removed under reduced pressure and the crude product was purified by flash chromatography on silica gel (cyclohexane/ethyl acetate=10:1) to obtain the title compound as a colourless solid in 6.56 g (17.6 mmol, 89%).

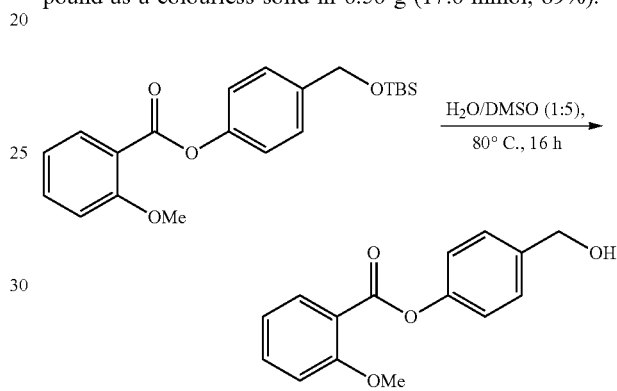

In an inert 250 mL three-necked flask 5.00 g (13.4 mmol, 1.00 eq) 2-methoxybenzoic acid-(tert-butyldimethylsilyl) oxy)-methylphenyl)-ester were dissolved in 15.00 mL water and 75.0 mL dimethylsulfoxide. After stirring for 16 h at 80° C. and cooling to room temperature 100.0 mL water were added. The mixture was extracted twice with 100.0 mL diethyl ether. The solvent was removed under reduced pressure and the crude product was purified by flash chromatography on silica gel (cyclohexane/ethyl acetate=1:1) to obtain the title compound as a colourless solid in 3.28 g (12.7 mmol, 95%).

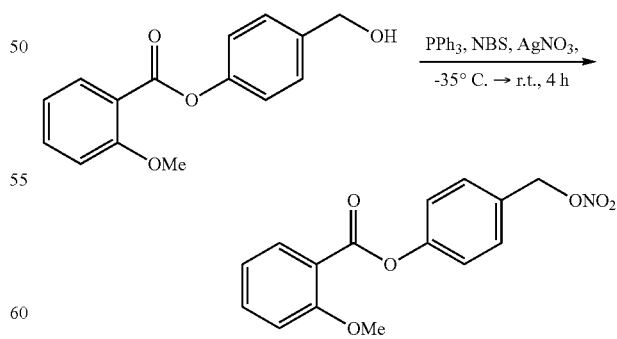

In an inert 25.0 mL Schlenk flask 1.00 g (3.87 mmol, 1.00 eq) 4-(hydroxymethyl)phenyl 2-methoxybenzoate and 1.02 g (3.87 mmol, 1.00 eq) triphenylphosphine were dissolved in 10.0 mL acetonitrile and 4.00 mL dichloromethane. The solution was cooled to −45° C. and 689 mg (3.87 mmol, 1.00 eq) N-bromosuccinimide were added. The cooling was removed, while NBS got dissolved slowly. 5 min later 987 mg (5.81 mmol, 1.50 eq) silver nitrate was added. After 4 h stirring at room temperature, the precipitate was filtered off. The solvent was removed from the filtrate under reduced pressure and the crude product was purified by flash chromatography on silica gel (cyclohexane/ethyl acetate=10:1) to obtain the title compound as a colourless solid in 889 mg (2.93 mmol, 76%).

B19: NO-4OMeBA

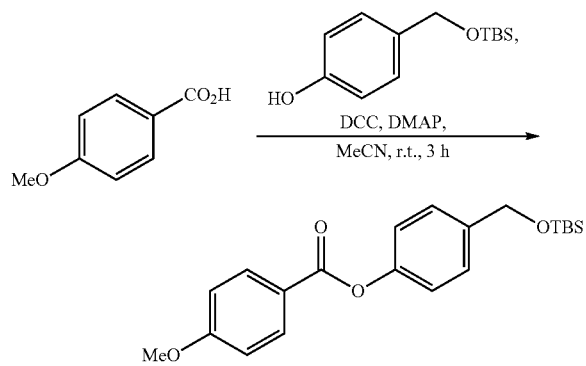

In an inert 250 mL Schlenk flask 3.00 g (19.7 mmol, 1.00 eq) 2-methoxy-benzoic acid were dissolved in 60.0 mL acetonitrile. 4.70 g (19.7 mmol, 1.00 eq) 4-(((tert-butyldimethylsilyl)oxy)methyl)phenol, 241 mg (1.97 mmol, 0.1 eq) 4-(dimethylamino)-pyridine and 4.48 g (21.7 mmol, 1.1 eq) dicyclohexylcarbodiimide were added. After 3 hours the solvent was removed under reduced pressure and the crude product was purified by flash chromatography on silica gel (cyclohexane/ethyl acetate=10:1) to obtain the title compound as a colourless solid in 6.60 g (17.7 mmol, 90%).

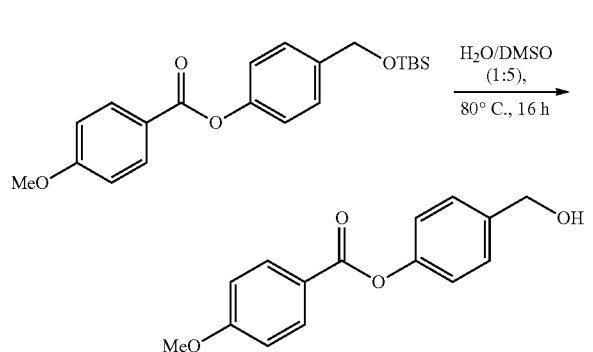

In an inert 250 mL three-necked flask 5.00 g (13.4 mmol, 1.00 eq) 4-(((tert-butyldimethylsilyl)oxy)methyl)phenyl 4-methoxybenzoate were dissolved in 15.00 mL water and 75.0 mL dimethylsulfoxide. After stirring for 16 h at 80° C. and cooling to room temperature 100.0 mL water were added. The mixture was extracted twice with 100.0 mL diethyl ether. The solvent was removed under reduced pressure and the crude product was purified by flash chromatography on silica gel (cyclohexane/ethyl acetate=1:1) to obtain the title compound as a colourless solid in 3.42 g (13.3 mmol, 99%).

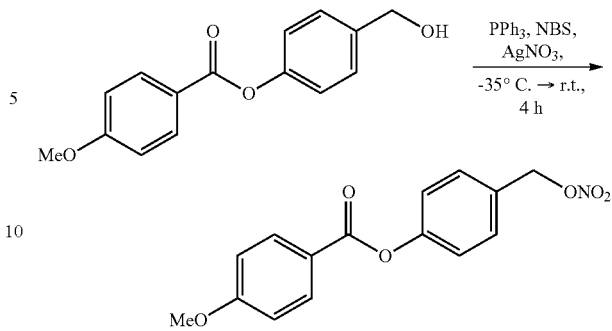

In an inert 25.0 mL Schlenk flask 3.00 g (11.6 mmol, 1.00 eq 4 (hydroxymethyl)phenyl 4-methoxybenzoate and 3.05 g (11.6 mmol, 1.00 eq) triphenylphosphine were dissolved in 10.0 mL acetonitrile and 4.00 mL dichloromethane. The solution was cooled to −45° C. and 2.06 g (11.6 mmol, 1.00 eq) N-bromosuccinimide were added. The cooling was removed, while NBS got dissolved slowly. 5 min later von 2.96 g (17.4 mmol, 1.50 eq) silver nitrate were added. After 4 h stirring at room temperature the precipitate was filtered off. The filtrate was removed from the solvent under reduced pressure and the crude product was purified by flash chromategraphy (cyclohexane/ethyl acetate=2:1) to obtain the title compound as a colourless solid in 2.45 g (8.07 mmol, 70%).

B20: NO-2Ethin-BA

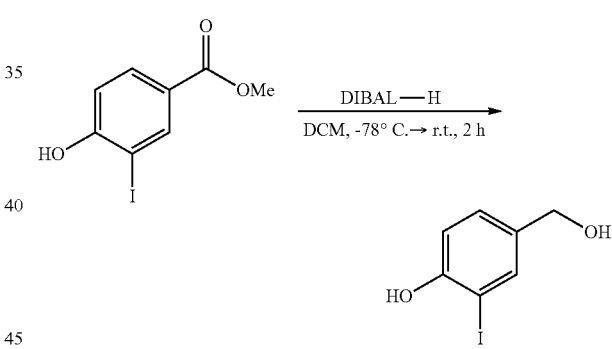

In an inert 500 mL Schlenk flask 2.00 g (7.19 mmol, 1.00 eq) methyl 4-hydroxy-3-iodobenzoate were dissolved in 200 mL dichloromethane and cooled to −78° C. Than 22.9 mL (25.2 mmol, 1.1 M, 3.50 eq) DIBAL-H were added. After 0.5 h the cooling was removed and stirring was continued for additional 2 hours. The mixture was worked up by adding 200 mL water and 30.0 mL acetic acid and extraction with 2×200 mL dichloromethane. The solvent was removed from combined organic layers under reduced pressure and the crude product was purified by flash chromatography on silica gel (cyclohexane/ethyl acetate=1:1) to obtain the title compound as a colourless solid in 1.74 g (6.96 mmol, 98%).

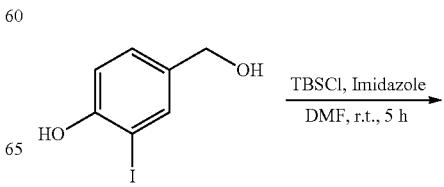

-continued

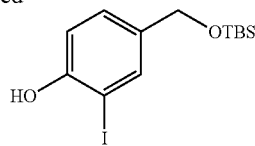

In an inert 10.0 mL Schlenk flask 408 mg (6.00 mmol, 1.50 eq) imidazole and 603 mg (4.00 mmol, 1.00 eq) tert-butyl(chloro)dimethylsilane were placed. After evacuating and flooding with argon twice, 4.0 mL dry DMF were added and stirred for 5 minutes at room temperature. Afterwards 1.00 g (4.00 mmol, 1.00 eq) 4-(hydroxymethyl)-2-iodophenol was added. The stirring was continued for 5 h. The suspension was mixed with 10 mL brine and extracted twice with 10 mL ethyl acetate. The solvent was removed under reduced pressure and the crude product was purified by flash chromatography on silica gel (cyclohexane/ethyl acetate=5:1) to obtain the title compound as a colourless oil in 213 mg (852 µmol, 21%).

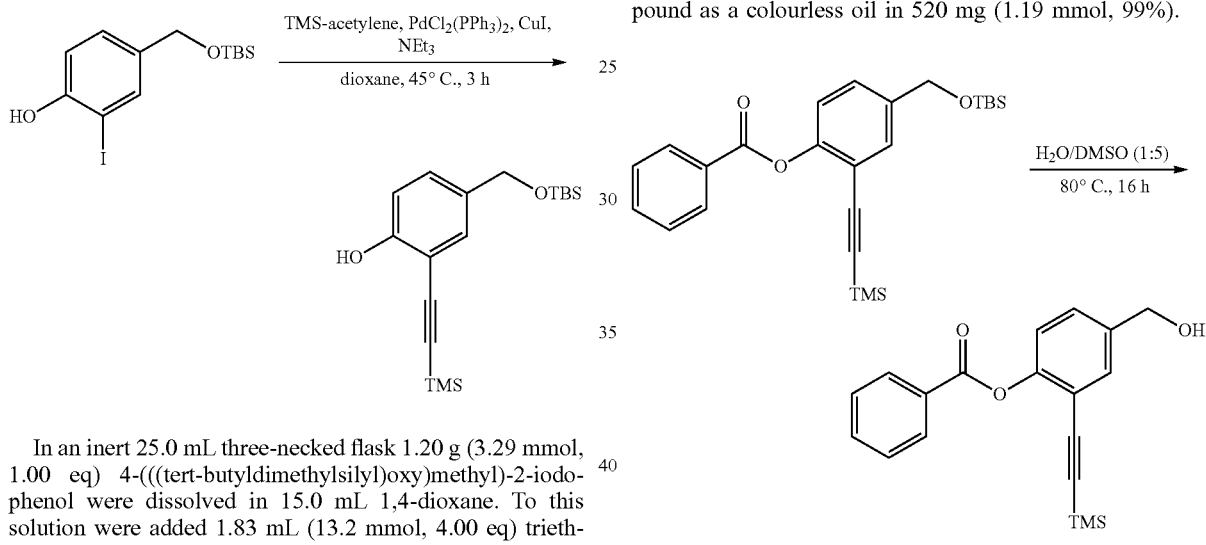

In an inert 25.0 mL three-necked flask 1.20 g (3.29 mmol, 1.00 eq) 4-(((tert-butyldimethylsilyl)oxy)methyl)-2-iodophenol were dissolved in 15.0 mL 1,4-dioxane. To this solution were added 1.83 mL (13.2 mmol, 4.00 eq) triethylamine, 599 µL (4.28 mmol, 1.30 eq) trimethylsilylacetylene, 23.0 mg (33.0 µmol, 0.01 eq) bis(triphenylphosphin)palladium(II) dichloride and 13.0 mg (66.0 µmol, 0.02 eq) copper(I) iodide. The mixture was heated to 45° C. After 3 hours 30.0 mL diethyl ether and 30.0 mL 0.1 N hydrochloric acid were added. The organic layer was washed with 30.0 mL saturated sodium hydrogen carbonate solution. The solvent was removed under reduced pressure and the crude product was purified by flash chromatography on silica gel (cyclohexane/ethyl acetate=20:1) to obtain the title compound as a yellow oil in 21.09 g (3.27 mmol, 99%).

-continued

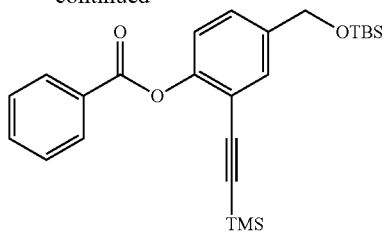

In an inert 50.0 mL three-necked flask 400 mg (1.20 mmol, 1.00 eq) benzoic acid were dissolved in 4.00 mL acetonitrile. 400 mg (1.20 mmol, 1.00 eq) 4-(((tert-Butyldimethylsilyl)oxy)methyl)-2-((trimethylsilyl)ethinyl)phenol, 15.0 mg (120 µmol, 0.10 eq) 4-(dimethylamino)-pyridine and 271 mg (1.32 mmol, 1.10 eq) dicyclohexylcarbodiimide were added. After 1 hour the solvent was removed under reduced pressure and the crude product was purified by flash chromatography on silica gel (cyclohexane/ethyl acetate=20:1) to obtain the title compound as a colourless oil in 520 mg (1.19 mmol, 99%).

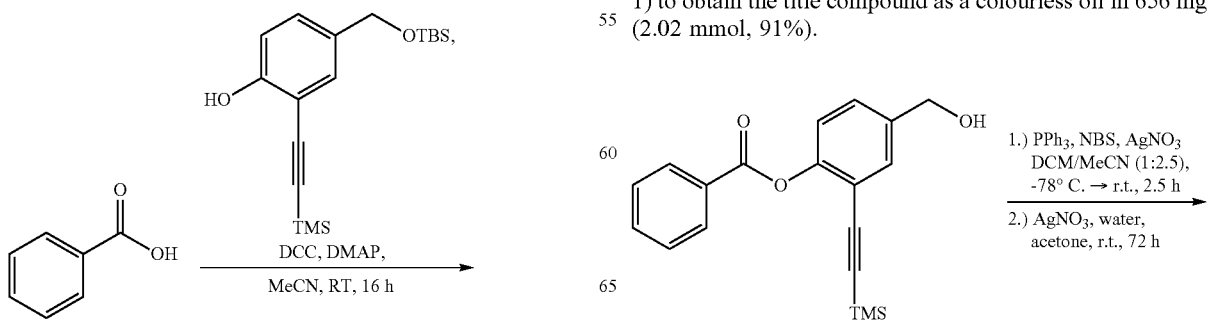

In an inert 500 mL round bottom flask 970 mg (2.21 mmol, 1.00 eq) 4-(((tert-butyldimethylsilyl)oxy)methyl)-2-((trimethylsily)ethynyl)phenyl benzoate were dissolved in 3.00 mL water and 15.0 mL dimethylsulfoxide. After stirring for 16 h at 80° C. and cooling to room temperature 20.0 mL water were added. The mixture was extracted twice with 20.0 mL diethyl ether. The solvent was removed under reduced pressure and the crude product was purified by flash chromatography on silica gel (cyclohexane/ethyl acetate=5:1) to obtain the title compound as a colourless oil in 656 mg (2.02 mmol, 91%).

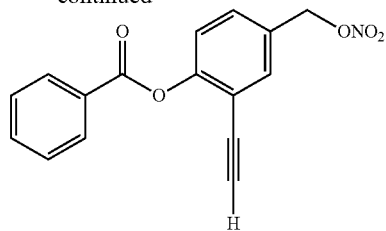

In an inert 10.0 mL Schlenk flask 50.0 mg (154 µmol, 1.00 eq) 4-(hydroxymethyl)-2-((trimethylsilyl)ethynyl)phenyl benzoate and 40.0 mg (154 µmol, 1.00 eq) triphenylphosphine were dissolved in 1.50 mL acetonitrile and 600 µL dichloromethane. The mixture was cooled to −78° C. and 27.0 mg (154 µmol, 1.00 eq) N-bromosuccinimide were added. The cooling was removed, while NBS got dissolved slowly. 5 min later 9.00 mg (231 µmol, 1.50 eq) silver nitrate were added. After 2.5 h stirring at room temperature the precipitate was filtered off. The solvent was removed from the filtrate under reduced pressure. The crude product was taken up with 293 µL water and 1.19 mL acetone. To this solution 2.76 mg (16.0 µmol, 0.1 eq) silver nitrate. After 72 h stirring at room temperature 15.0 mL brine were added. The mixture was extracted with 2×15.0 mL dichloromethane. The solvent was removed from the extract under reduced pressure and the crude product was purified by flash chromatography on silica gel (cyclohexane/ethyl acetate=5:1) to obtain the title compound as a solid in 20.0 mg (67.0 µmol, 41%) over two steps.

What is claimed is:

1. A method of treating a cancer by administering to a subject an effective amount of a compound selected from the group consisting of:

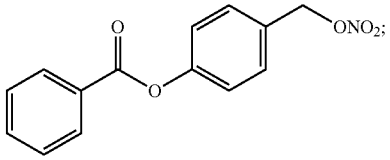

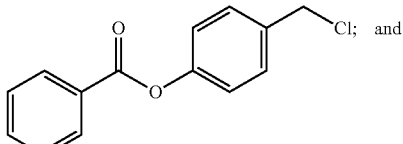

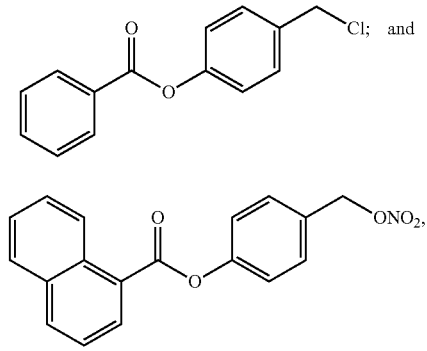

or a pharmaceutically acceptable salt thereof, wherein the cancer is selected from the group consisting of a lung cancer, a skin cancer, a colon cancer, a blood cancer, and an ovarian cancer.

2. The method according to claim 1, wherein the cancer is ovarian cancer.

3. The method according to claim 1, wherein the cancer is chronic lymphocytic leukemia.

* * * * *